United States Patent [19]
Ritter et al.

[11] Patent Number: 5,985,837
[45] Date of Patent: Nov. 16, 1999

[54] DOLASTATIN 15 DERIVATIVES

[75] Inventors: Kurt Ritter, Newton; Bernd Janssen, Marlborough; Andreas Haupt, Westborough, all of Mass.; Andreas Kling, Mannheim, Germany; Teresa Barlozzari, Wellesley, Mass.; Wilhelm Amberg, Friedrichsdorf, Germany

[73] Assignee: BASF Aktiengesellschaft, Germany

[21] Appl. No.: 09/112,249

[22] Filed: Jul. 8, 1998

[51] Int. Cl.⁶ .......................... A61K 38/04; A61K 38/08; A61K 38/07; C07K 7/04
[52] U.S. Cl. .............................. 514/18; 514/17; 530/330; 530/333; 530/338
[58] Field of Search ........................ 514/17, 18; 530/330, 530/333, 338

[56] References Cited

U.S. PATENT DOCUMENTS

| | | | |
|---|---|---|---|
| 4,816,444 | 3/1989 | Pettit et al. | 514/17 |
| 5,502,032 | 3/1996 | Haupt et al. | 514/17 |
| 5,504,191 | 4/1996 | Pettit et al. | 530/330 |
| 5,530,097 | 6/1996 | Pettit et al. | 530/330 |
| 5,554,725 | 9/1996 | Pettit | 530/330 |

FOREIGN PATENT DOCUMENTS

| | | |
|---|---|---|
| 0 398 558 | 11/1990 | European Pat. Off. |
| 0 598 129 | 5/1994 | European Pat. Off. |
| 92/02541 | 2/1992 | WIPO |
| 93/23424 | 11/1993 | WIPO |
| 96/40751 | 12/1996 | WIPO |
| 96/40752 | 12/1996 | WIPO |
| 97/17364 | 5/1997 | WIPO |

OTHER PUBLICATIONS

Pettit et al., Isolation of Dolastatin 10–15 from the Murine Mollusc *Dolabella auricularia* Tetrahedron vol. 49, No. 41, pp. 9151–9170, 1993.

Roux et al., Synthesis and In Vitro Cytotoxicity of Diasterioisomerically Modified Dolastatin 15 Analogues, Bioorganic and Medicinal Chemistry Letters, vol. 4, No. 16, pp. 1947–1950, 1944.

Pettit, G.R., et al., "The Isolation and Structure of a Remarkable Marine Animal Antineoplastic Constituent: Dolastatin 10," *J. Am. Chem. Soc.* 109:6883–6885 (1987).

Bai, R., et al., "Structure–Activity Studies with Chiral Isomers and with Segments of the Antimitotic Marine Peptide Dolastatin 10," *Biochemical Pharmacology* 40(8):1859–1864 (1990).

Pettit, G.R., et al. "Antineoplastic Agents. 220. Synthesis of Natural (−)–Dolastatin 15," *J. Am. Chem. Soc.* 113:6692–6693 (1991).

Bai, R., et al., "Dolastatin 15, a potent antimitotic depsipeptide derived from *Dolabella auricularia*. Interaction with tubulin and effects on cellular microtubules," *1–Pharmacology* Abstract 117: 103735g p. 41 (1992).

Pettit, G.R., et al., "Isolation and Structure of the Cytostatic Depsipeptide Dolastatin 13 from the Sea Hare *Dolabella auricularia*," *J. Am. Chem. Soc.* 111(13):5015–5017 (1989).

Pettit, G.R., et al., "Antineoplastic Agents 337. Synthesis of Dolastatin–10 Structural Modifications," *Anti–Cancer Drug Design* 10:529–544 (1995).

Miyazaki, K., et al., "Synthesis and Antitumor Activity of Novel Dolastatin–10 Analogs," *Chem. Pharm. Bull.* 43(10):1706–1718 (1995).

Pettit, G.R., et al., "Isolation and Structure of the Cytostatic Linear Depsipeptide Dolastatin 15," *J. Org. Chem.* 54:6005–6006 (1989).

Pettit, G.R., et al., "The Dolastatins 20. A convenient synthetic route to Dolastatin 15." *Tetrahedron* 50(42):12097–12108 (1994).

*Primary Examiner*—F. T. Moezie
*Attorney, Agent, or Firm*—Hamilton, Brook, Smith & Reynolds, P.C.

[57] ABSTRACT

Compounds of the present invention include cell growth inhibitors which are peptides of Formula I

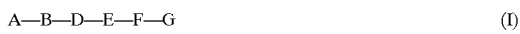

A—B—D—E—F—G    (I)

and acid salts thereof, wherein A, D, and E are α-amino acid residues, B is an α-amino acid residue or an α-hydroxy acid residue, F is an aminobenzoic acid residue or an aminocycloalkanecarboxylic acid residue, and G is a monovalent radical, such as, for example, a hydrogen atom, an amino group, an alkyl group, an alkylene alkyl ether, an alkylene alkyl thioether, an alkylene aldehyde, an alkylene amide, a β-hydroxylamino group, a hydrazido group, an alkoxy group, a thioalkoxy group, an aminoxy group, an oximato group, an alkylene aryl group, an alkylene ester, an alkylene sulfoxide or an alkylene sulfone. Another aspect of the present invention includes pharmaceutical compositions comprising a compound of Formula I and a pharmaceutically acceptable carrier. An additional embodiment of the present invention is a method for treating cancer in a mammal, such as a human, comprising administering to the mammal an effective amount of a compound of Formula I in a pharmaceutically acceptable composition.

21 Claims, No Drawings

1

DOLASTATIN 15 DERIVATIVES

BACKGROUND OF THE INVENTION

A number of short peptides with significant activity as inhibitors of cell growth have been isolated from the Indian Ocean sea hare *Dolabella auricularia* (Bai, et al., *Biochem. Pharmacology* 40: 1859–1864 (1990); Beckwith et al., *J. Natl. Cancer Inst.* 85: 483–488 (1993) and references cited therein). These include Dolastatins 1–10 (U.S. Patent No. 4,816,444, issued to Pettit et al.) and Dolastatin-15 (European Patent Application No. 398558). Dolastatin 15, for example, markedly inhibits the growth of the National Cancer Institute's P388 lymphocytic leukemia (PS system) cell line, a strong predictor of efficacy against various types of human malignancies.

The exceedingly small amounts of the various Dolastatin peptides present in *Dolabella auricularia* (about 1 mg each per 100 kg sea hare) and the consequent difficulties in purifying amounts sufficient for evaluation and use, have motivated efforts toward the synthesis of these compounds (Roux et al., *Tetrahedron* 50: 5345–5360 (1994); Shioiri et al., *Tetrahedron* 49: 1913–24 (1993); Patino et al., *Tetrahedron* 48: 4115–4122 (1992) and references cited therein). Synthetic Dolastatin 15, however, suffers from drawbacks which include poor solubility in aqueous systems and the need for expensive starting materials for its synthesis. These, in turn, have led to the synthesis and evaluation of structurally modified Dolastatin 15 derivatives (see, for example, *Bioorg. Med. Chem. Lett.* 4: 1947–50 (1994); WO 93 03054; JP-A-06234790).

However, there is a need for synthetic compounds with the biological activity of Dolastatin 15 which have useful aqueous solubility and can be produced efficiently and economically.

SUMMARY OF THE INVENTION

Compounds of the present invention include cell growth inhibitors which are peptides of Formula I

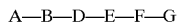 (I)

and acid salts thereof, wherein A, D, and E are α-amino acid residues, B is an α-amino acid residue, F is an aminobenzoic acid residue or an aminocycloalkanecarboxylic acid residue, and G is a monovalent radical, such as, for example, a hydrogen atom, an amino group, an alkyl group, an alkylene alkyl ether, an alkylene alkyl thioether, an alkylene aldehyde, an alkylene amide, a β-hydroxylamino group, a hydrazido group, an alkoxy group, a thioalkoxy group, an aminoxy group, an oximato group, an alkylene aryl group, an alkylene ester, an alkylene sulfoxide or an alkylene sulfone.

Another aspect of the present invention includes pharmaceutical compositions comprising a compound of Formula I and a pharmaceutically acceptable carrier.

An additional embodiment of the present invention is a method for treating cancer in a mammal, such as a human, comprising administering to the mammal an effective amount of a compound of Formula I in a pharmaceutically acceptable composition.

The present invention provides compounds with antineoplastic activity as well as increased metabolic stability relative to Dolastatin 15.

DETAILED DESCRIPTION OF THE INVENTION

The present invention relates to peptides having antineoplastic activity. It also includes pharmaceutical compositions comprising these compounds and methods for treating cancer in a mammal, including a human, by administration of these compositions to the mammal.

The invention is based on the discovery that Dolastatin 15, a peptide isolated from the sea hare *Dolabella auricularia*, is a potent inhibitor of cell growth. This compound, however, is present in trace quantities in the sea hare, and is, thus, difficult to isolate and expensive to synthesize and suffers from poor aqueous solubility. As shown herein, however, Dolastatin 15 can serve as a starting point for the development of compounds which overcome these disadvantages while retaining antineoplastic activity or exhibiting greater antineoplastic activity than the natural product. Applicants have discovered that certain structural modifications of Dolastatin 15 provide compounds with a surprisingly improved therapeutic potential for the treatment of neoplastic diseases as compared to Dolastatins-10 and -15. The Dolastatin-15 derivatives exhibit activity even in multiple drug-resistant tumor systems and an unpredicted high solubility in aqueous solvents. Furthermore, the compounds of the present invention can be conveniently synthesized, as described below in detail.

For the purposes of the present invention, the term "monovalent radical" is intended to mean an electrically neutral molecular fragment capable of forming one covalent bond with a second neutral molecular fragment. Monovalent radicals include the hydrogen atom, alkyl groups, such as methyl, ethyl and propyl groups, halogen atoms, such as fluorine, chlorine and bromine atoms, aryl groups, such as phenyl and naphthyl groups, and alkoxy groups, such as methoxy and ethoxy groups. Two monovalent radicals on adjacent sigma-bonded atoms can also together form a pi bond between the adjacent atoms. Two monovalent radicals may also be linked together, for example, by a polymethylene unit, to form a cyclic structure. For example, in the unit —N(R)R', R and R' are each a monovalent radical, and can, together with the nitrogen atom, form a heterocyclic ring. In addition, two monovalent radicals bonded to the same atom can also together form a divalent radical, such as an alkylidene group, for example, a propylidene group, or an oxygen atom.

For the purposes of the present invention, the term "residue" refers to the molecular fragment remaining after the removal of the elements of a water molecule (one oxygen atom, two hydrogen atoms) from a molecule, such as an amino acid or a hydroxy acid.

For the purposes of the present invention the term "normal alkyl" refers to an unbranched, or straight chain, alkyl group, for example, normal propyl (n-propyl, —CH$_2$CH$_2$CH$_3$).

The compounds of the present invention can be represented by Formula I,

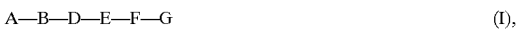 (I), wherein A, D and E are α-amino acid residues; B is an α-amino acid residue or an α-hydroxy acid residue; F is an aminobenzoic acid residue, or an aminocycloalkanecarboxylic acid residue, such as an aminocyclobutanecarboxylic acid residue, an aminocylopentanecarboxylic acid residue, or an aminocyclohexanecarboxylic acid residue; and G is a monovalent radical.

The peptides of Formula I are generally composed of L-amino acids but they can contain one or more D-amino acids. They can also be present as salts with physiologically-compatible acids, including hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The following is a description of the present invention, including a detailed description of individual components and of methods of using the claimed compounds.

Compounds of the Present Invention

Identity of A

In one embodiment, A is an amino acid derivative of Formula II$_a$,

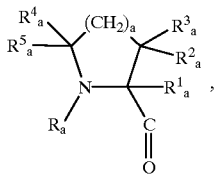

(II$_a$)

where n$_a$ is an integer, preferably 0, 1, 2, or 3. R$_a$ is a monovalent radical, such as a hydrogen atom or a C$_1$–C$_3$-alkyl group which can be normal, branched or cyclic and can be substituted by one or more, preferably 1 to about 3, fluorine atoms; suitable examples include methyl, ethyl, isopropyl, 2-fluoroethyl, 2,2,2-trifluoroethyl, 1-methyl-2-fluoroethyl, 1-fluoromethyl-2-fluoroethyl or cyclopropyl; methyl, ethyl or isopropyl are preferred;

In this embodiment, R$^1$$_a$ is a monovalent radical, such as a hydrogen atom or a methyl, ethyl, propyl or phenyl group. The phenyl group can be substituted; suitable substituents include one or more halogen atoms, with fluorine, chlorine and bromine being preferred, C$_1$–C$_4$-alkyl groups, methoxy, ethoxy, trifluoromethyl or nitro groups.

R$^2$$_a$, R$^3$$_a$, R$^4$$_a$ and R$^5$$_a$ are each, independently, a monovalent radical, such as a hydrogen atom or a methyl group. R$_a$ and R$^1$$_a$ together can also form a propylene bridge.

In another embodiment, A is an amino acid derivative of Formula III$_a$,

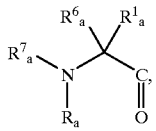

(III$_a$)

where R$_a$ has the meaning stated for Formula II$_a$, R$^1$$_a$ is a monovalent radical, for example, a hydrogen atom or a lower alkyl group, preferably a methyl, ethyl or propyl group.

In this embodiment, R$^6$$_a$ is a monovalent radical, such as a hydrogen atom, a normal or branched C$_1$–C$_8$-alkyl group, which can be substituted by one or more halogen, preferably fluorine, atoms, or a C$_3$–C$_8$-cycloalkyl or C$_3$–C$_8$-cycloalkyl-C$_1$–C$_4$-alkyl group, a C$_1$–C$_4$-oxoalkyl group such as a methoxymethyl, 1-methoxyethyl or 1,1-dimethylhydroxymethyl group, a C$_2$–C$_5$ alkenyl group, such as a vinyl or 1-methylvinyl group, or a substituted or unsubstituted phenyl group. Suitable phenyl substituents include one or more halogen atoms, preferably fluorine, chlorine or bromine atoms, and alkyl, methoxy, ethoxy, trifluoromethyl, or nitro groups. R$^7$$_a$ is a monovalent radical, preferably a methyl group or an ethyl group.

In another embodiment, A is an amino acid residue of Formula IV$_a$,

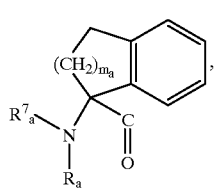

(IV$_a$)

where m$_a$ is an integer, preferably 1 or 2. R$_a$ and R$^7$$_a$ have the meanings stated for R$_a$ and R$^7$$_a$ in Formula III$_a$.

In another embodiment, A is an amino acid residue of Formula V$_a$,

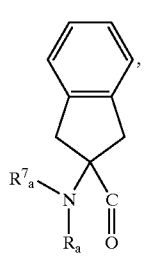

(V$_a$)

where R$_a$ and R$^7$$_a$ have the meanings stated for R$_a$ and R$^7$$_a$ in Formula III$_a$.

In a further embodiment, A is a substituted proline derivative of Formula VI$_a$,

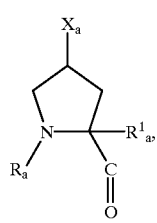

(VI$_a$)

where R$_a$ and R$^1$$_a$ have the meanings stated for R$_a$ and R$^1$$_a$ in Formula II$_a$, and X$_a$ is a monovalent radical, preferably a hydroxyl, methoxy or ethoxy group or a fluorine atom.

In another embodiment, A is a thiaprolyl derivative of Formula VII$_a$,

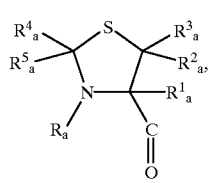

(VII$_a$)

where R$_a$, R$^1$$_a$, R$^2$$_a$, R$^3$$_a$, R$^4$$_a$ and R$^5$$_a$ have the meanings stated for these variables in Formula II$_a$.

In another embodiment, A is a 1,3-dihydroisoindole derivative of Formula VIII$_a$,

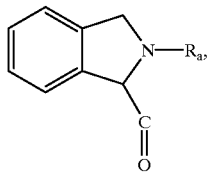

(VIII$_a$)

where R$_a$ has the meaning stated for R$_a$ in Formula II$_a$.

In another embodiment, A is a 2-azabicyclo[2.2.1]heptane-3-carboxylic acid derivative of Formula IX$_a$,

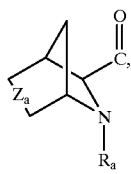

(IX$_a$)

where Z$_a$ is a single or double bond and R$_a$ has the meaning stated for this variable in Formula II$_a$. The 3-carbonyl substituent can have either the exo or endo orientation.

Identity of B

B is a valyl, isoleucyl, allo-isoleucyl, norvalyl, 2-tert-butylglycyl or 2-ethylglycyl residue. B can also be a carboxylic acid derivative of Formula II$_b$,

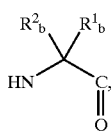

(II$_b$)

wherein R$^1_b$ and R$^2_b$ are each a monovalent radical. R$^1_b$ is, preferably, a hydrogen atom and R$^2_b$ is, for example, a cyclopropyl group, a normal or branched butyl, preferably tertiary-butyl, group, a methoxymethyl group, a 1-methoxyethyl group or a 1-methylvinyl group. Additionally, R$^1_b$ and R$^2_b$ together can be an isopropylidene group.

Identity of D

D is an N-alkylvalyl, N-alkyl-2-ethylglycyl, N-alkyl-2-tert-butylglycyl, N-alkyl-norleucyl, N-alkyl-isoleucyl, N-alkyl-allo-isoleucyl or N-alkyl-norvalyl residue, where the alkyl group is preferably methyl or ethyl.

In another embodiment, D is an α-amino carboxylic acid derivative of Formula II$_d$,

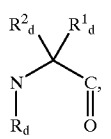

(II$_d$)

where R$_d$ has the meaning stated for R$_a$ in Formula III$_a$, R$^1_d$ is a monovalent radical, preferably a hydrogen atom, and R$^2_d$ is a monovalent radical such as a cyclopropyl group, a methoxymethyl group, a 1-methoxyethyl group or a 1-methylvinyl group. Additionally, R$^1_d$ and R$^2_d$ together can form an isopropylidene group.

Alternatively, D can be a proline derivative of Formula III$_d$,

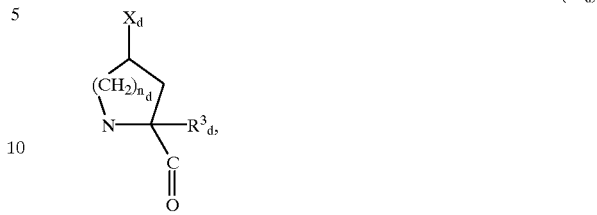

(III$_d$)

where n$_d$ is an integer, for example, 1 or 2, and R$^3_d$ has the meaning stated for R$^1_a$ in Formula III$_a$, X$_d$ is a monovalent radical, preferably a hydrogen atom, and, in the case where n$_d$ equals 1, can also be a hydroxyl, methoxy or ethoxy group or a fluorine atom.

Identity of E

E is a prolyl, thiazolidinyl-4-carbonyl, homoprolyl or hydroxyprolyl residue, or a cyclic α-amino carboxylic acid residue of Formula II$_e$,

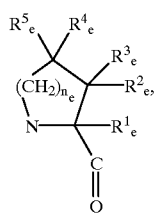

(II$_e$)

where n$_e$ is an integer, preferably 0, 1 or 2. R$^1_e$ has the meaning stated for R$^1_a$ in Formula III$_a$. R$^2_e$ and R$^3_e$ are each a monovalent radical, and can be, independently, a hydrogen atom or a methyl group. R$^4_e$ is a monovalent radical, preferably a hydrogen atom, a hydroxyl, methoxy or ethoxy group or a fluorine atom. R$^5_e$ is a monovalent radical, preferably a hydrogen atom. In the case where n$_e$ has the value 1, R$^3_e$ and R$^4_e$ together can form a double bond or R$^4_e$ and R$^5_e$ can together be a double-bonded oxygen radical. In the case where n$_e$ has the value 1 or 2, R$^1_e$ and R$^2_e$ can together form a double bond.

In another embodiment, E is a 2- or 3-amino-cyclopentanecarboxylic acid residue of Formula III$_e$,

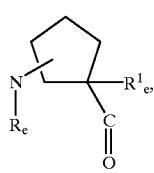

(III$_e$)

where R$_e$ is a monovalent radical, such as a methyl or ethyl group and R$^1_e$ has the meaning stated for R$^1_a$ in Formula III$_a$.

Identity of F

In one embodiment, F is an aminobenzoyl derivative of Formula II$_f$,

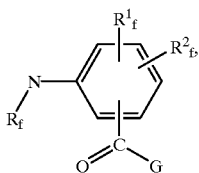

(II_f)

where $R_f$ is a hydrogen atom or an alkyl group, preferably a methyl, ethyl or propyl group. The carbonyl group can be in position 1 (ortho), 2 (meta), or 3 (para) of the phenyl ring relative to the nitrogen atom. $R^1_f$ and $R^2_f$ are each, independently, a hydrogen atom; a halogen atom, for example, a fluorine, chlorine, bromine, or iodine atom; a $C_1$–$C_4$-alkyl group; a methoxy, ethoxy, trifluoromethyl, nitro, cyano, amino or dimethylamino group. Additionally, $R^1_f$ and $R^2_f$ can together form a dioxymethylene group.

In another embodiment, F is an aminocycloalkanecarboxylic acid residue of Formula III_f,

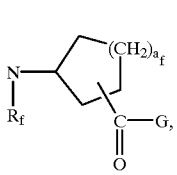

(III_f)

where $R_f$ is a monovalent radical, such as a hydrogen atom or a lower alkyl group, preferably a methyl, ethyl or propyl group. $a_f$ is an integer, for example, 0, 1 or 2. The carbonyl group is in position 2 or position 3 of the cycloalkane ring relative to the nitrogen atom at position 1. The stereogenic centers can be, independently of each other, R or S. For a five-membered ring ($a_f$=1), the combinations R1,S2 and S1,R2 would be referred to as cis-pentacin derivatives, while the combinations R1,R2 and S1,S2 are trans-pentacin derivatives.

Identity of G

In one embodiment, G is an amino or substituted amino group of Formula II_g,

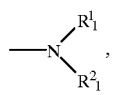

(II_g)

where $R^1_l$ is a monovalent radical, such as a hydrogen atom, a normal or branched, saturated or unsaturated $C_1$–$C_{18}$-alkoxy group, a substituted or unsubstituted aryloxy group, a substituted or unsubstituted aryl-$C_1$–$C_6$-alkoxy group, or a substituted or unsubstituted aryloxy-$C_1$–$C_6$-alkoxy or heteroaryl-$C_1$–$C_6$-alkoxy group. The aryl group is preferably a phenyl or naphthyl group. The heteroaryl group is a 5- or 6-membered, preferably nitrogen-, oxygen- or sulfur-containing, ring system, such as, for example, imidazolyl, isoxazolyl, isothiazolyl, thiazolyl, oxazolyl, pyrazolyl, thiophenyl, furanyl, pyrrolyl, 1,2,4- or 1,2,3-triazolyl, pyrazinyl, indolyl, benzofuranyl, benzothiophenyl, isoindolyl, indazolyl, quinolinyl, pyridazinyl, pyrimidinyl, benzimidazolyl, benzopyranyl, benzothiazolyl, oxadiazolyl, thiadiazolyl or pyridinyl group. Suitable aryl or heteroaryl substituents include one or more halogen atoms, preferably fluorine, bromine or chlorine; $C_1$–$C_4$-alkyl groups; methoxy, ethoxy or trifluoromethyl groups, a dioxymethylene group or a nitro group.

$R^2_l$ is a monovalent radical, such as a hydrogen atom, a normal or branched, saturated or unsaturated $C_1$–$C_{18}$-alkyl group, a $C_3$–$C_{10}$-cycloalkyl group, a substituted or unsubstituted aryl group, where aryl is preferably phenyl or naphthyl. Suitable aryl substituents include one or more halogen, preferably fluorine, chlorine or bromine, atoms, $C_1$–$C_4$-alkyl groups, methoxy, ethoxy or trifluoromethyl groups, a dioxymethylene group, nitro or cyano groups, a $C_1$–$C_7$-alkoxycarbonyl group, a $C_1$–$C_7$-alkylsulfonyl group, an amino or $C_1$–$C_7$-dialkylamino group, where the alkyl groups can, together with the nitrogen atom, also form a 5- or 6-membered heterocycle, or an unsubstituted or substituted heteroaryl group. The heteroaryl group can be a 5- or 6-membered, preferably nitrogen-, oxygen- or sulfur-containing, ring system which can be fused to a benzene ring, such as, for example, imidazolyl, pyrrolyl, thiophenyl, furanyl, thiazolyl, oxazolyl, pyrazolyl, 1,2,4- or 1,2,3-triazolyl, oxadiazolyl, thiadiazolyl, isoxazolyl, isothiazolyl, pyrazinyl, pyridazinyl, pyrimidinyl, pyridinyl, benzofuranyl, benzothiophenyl, benzimidazolyl, benzothiazolyl, benzopyranyl, indolyl, isoindolyl, indazolyl or quinolinyl group, with preferred substituents being $C_1$–$C_6$-alkyl groups, or hydroxyl or phenyl groups.

$R^2_l$ can additionally be of Formula II_l,

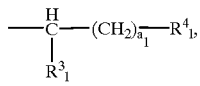

(II_l)

wherein $a_l$ is an integer, preferably 0, 1, 2, 3, 4, or 5. $R^3_l$ is a monovalent radical, such as a lower alkyl group, for example, a methyl, ethyl, propyl or isopropyl group. $R^4_l$ is a saturated or partially unsaturated carbocyclic group containing from 3 to about 10 carbon atoms, or a substituted or unsubstituted aryl or heteroaryl group, where the preferred aryl and heteroaryl groups and suitable substituents are as stated for $R^2_l$ in Formula II_g.

$R^2_l$ can also be a monovalent radical of Formula III_l,

(III_l).

wherein $W_l$ is an oxygen or sulfur atom or an N—$R^6_l$ group. $R^5_l$ is a monovalent radical, such as a hydrogen atom, a $C_1$–$C_4$-alkyl or $C_3$–$C_7$-cycloalkyl group or a substituted or unsubstituted aryl or arylmethyl group, with aryl and its preferred substituents having the meaning stated for $R^2_l$ from Formula II_g. $R^6_l$ is a monovalent radical, preferably a hydrogen atom, a $C_1$–$C_4$-alkyl group or a $C_3$–$C_7$-cycloalkyl group, a $C_1$–$C_{18}$-alkanoyl group, a benzoyl group or a substituted or unsubstituted aryl or arylmethyl group, with aryl and its preferred substituents having the meaning stated for $R^2_l$ in Formula II_g.

$R^2_l$ can alternately be a substituent of Formula IV_l,

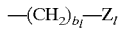

(IV_l), where $b_l$ is an integer, preferably 2, 3 or 4. $Z_l$ is a monovalent radical, such as a formyl, aminocarbonyl or hydrazinocarbonyl group, or a cyclic or acyclic acetal or thioacetal group.

$R^2_l$ can also be a substituent of Formula $V_l$,

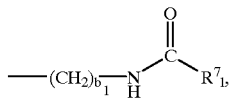
(V$_l$)

in which $b_l$ is an integer, preferably 2, 3 or 4. $R^7_l$ is a monovalent radical, such as a glycol oligomer of the formula

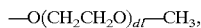

where $d_l$ is an integer, preferably in the range from about 2 to about 4 or from about 40 to about 90.

$R^2_l$ can further be a carbohydrate of Formula $VI_l$,

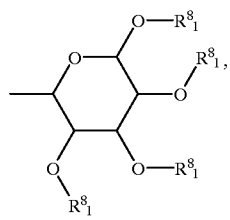
(VI$_l$)

where $R^8_l$ is a monovalent radical, such as a hydrogen atom, a $C_1$–$C_4$-alkanoyl or alkyl group, a benzoyl group or a benzyl group.

In another embodiment, G is an β-hydroxy amine of Formula $III_g$,

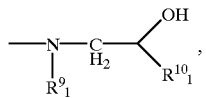
(III$_g$)

where $R^9_l$ is a monovalent radical such as a hydrogen atom, a $C_1$–$C_6$-alkyl group or a substituted or unsubstituted aryl group, with aryl and its preferred substituents having the meaning stated for $R^2_l$ in Formula $II_g$. $R^{10}_l$ is a monovalent radical, preferably a hydrogen atom, alkyl, for example, methyl, or a phenyl group.

Another subclass of compounds of this invention includes peptides of Formula I wherein G is a hydrazido group of Formula $IV_g$,

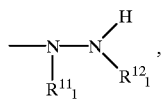
(IV$_g$)

where $R^{11}_l$ and $R^{12}_l$ are each, independently, a monovalent radical such as a hydrogen atom, a normal or branched $C_1$–$C_8$-alkyl group, a $C_3$–$C_8$-cycloalkyl group, a $C_3$–$C_8$-cycloalkyl-$C_1$–$C_4$-alkyl group or a substituted or unsubstituted aryl, heteroaryl, aryl-$C_1$–$C_4$-alkyl or heteroaryl-$C_1$–$C_4$-alkyl group, where aryl, heteroaryl and their preferred substituents can be selected from among the options listed for $R^2_l$ in Formula $II_g$. $R^{11}_l$ and $R^{12}_l$ can also together form a propylene or butylene bridge.

Another subclass of compounds of this invention includes peptides of Formula I wherein G is a monovalent radical of the formula —O—$R^{13}_l$ or —S—$R^{13}_l$, where $R^{13}_l$ is a monovalent radical, such as a $C_3$–$C_{10}$-cycloalkyl group, a normal or branched $C_2$–$C_{16}$-alkenylmethyl group or a $C_1$—$C_{16}$-alkyl group which can be substituted by from 1 to about 5 halogen, preferably fluorine, atoms.

$R^{13}_l$ can also be the radical —(CH$_2$)$_{e_l}$—$R^{14}_l$ where $e_l$ is an integer, preferably 1, 2 or 3. $R^{14}_l$ is a monovalent radical, preferably a saturated or partially unsaturated $C_3$–$C_{10}$-carbocycle.

$R^{13}_l$ can further be the radical

where $f_l$ is an integer, preferably 1, 2, 3 or 4.

$R^{13}_l$ can also be the radical

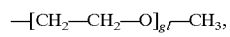

where $g_l$ is an integer, preferably from about 2 to about 4, or from about 40 to about 90.

$R^{13}_l$ can also be the radical

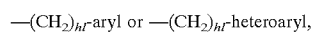

where aryl and heteroaryl can also be substituted and, along with their preferred substituents, can be selected from the group listed for $R^2_l$ in Formula $II_g$. $h_l$ is an integer, preferably 0, 1, 2 or 3.

$R^{13}_l$ can further be the radical

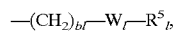

where $b_l$, $W_l$ and $R^5_l$ are each selected from among the options described for Formula $III_l$.

Another subclass of compounds of this invention includes peptides of Formula I in which G is an aminoxy group of the formula

where $R^{15}_l$ and $R^{16}_l$ are each a monovalent radical, and can independently be a hydrogen atom, a normal or branched $C_1$–$C_8$-alkyl group, which can be substituted by halogen, preferably fluorine, atoms, a $C_3$–$C_8$-cycloalkyl group, a $C_3$–$C_8$-cycloalkyl-$C_1$–$C_4$-alkyl group, a substituted or unsubstituted aryl or heteroaryl group or a substituted or unsubstituted aryl-$C_1$–$C_4$-alkyl group. Aryl and heteroaryl groups and the preferred substituents thereof can be selected from the options listed for $R^2_l$ in Formula $II_g$. Additionally, $R^{15}_l$ and $R^{16}_l$ can together form a 5-, 6- or 7-membered heterocycle.

Another subclass of compounds of this invention includes peptides of Formula I wherein G is an oximato group of the formula

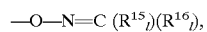

where $R^{15}_l$ and $R^{16}_l$ are selected from among the options listed above and, additionally, can together form a cyclic system comprising, preferably, from about 3 to about 7 ring atoms. This cyclic system can additionally be fused to one or more aromatic rings. Particularly preferred cyclic systems are shown below.

(a) 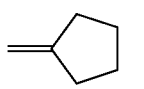

(b) 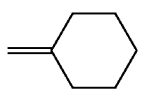

(c) 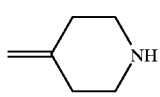

(d) 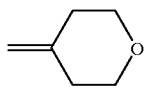

(e) 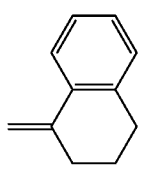

(f) 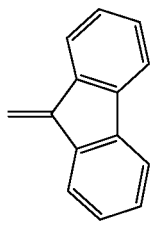

(g) 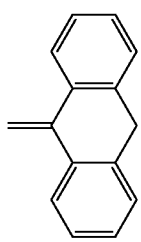

(h) 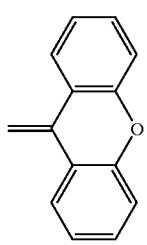

(i) 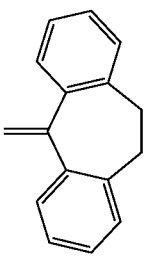

(j) 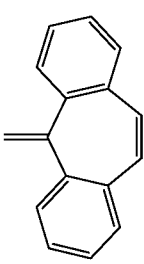

(k) 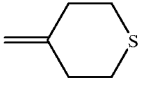

(l) 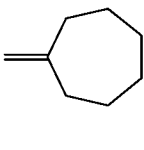

A further subclass of compounds of this invention includes peptides of Formula I wherein G is a hydrogen atom, a normal or branched $C_1$–$C_8$-alkyl group, which can be substituted by up to six halogen, preferably fluorine, atoms, a $C_3$–$C_8$-cycloalkyl group or a $C_3$–$C_8$-cycloalkyl-$C_1$–$C_4$-alkyl group.

G can also be an arylalkyl, heteroarylalkyl, aryl or heteroaryl group of Formula $V_g$, $$-(CH_2)_{a_g}-R^{17}{}_l \qquad (V_g)$$

where $a_g$ is an integer, such as 0, 1 or 2. $R^{17}{}_l$ is a substituted or unsubstituted aryl or heteroaryl group. Preferred aryl groups include phenyl and naphthyl groups. Suitable aryl substituents include halogen, preferably fluorine, bromine or chlorine, atoms, $C_1$–$C_4$-alkyl groups, methoxy, ethoxy or trifluoromethyl groups, a dioxymethylene group, a nitro or cyano group, a $C_1$–$C_7$-alkoxycarbonyl group, a $C_1$–$C_7$-alkylsulfonyl group, an amino group or a $C_1$–$C_6$-dialkylamino group, where the alkyl groups can, together with the nitrogen atom, also form a 5- or 6-membered heterocycle. $R^{17}{}_l$ can also be a 5- or 6-membered, preferably nitrogen-, oxygen- or sulfur-containing, ring system which can be fused to a benzene ring. Suitable heteroaryl groups include imidazolyl, pyrrolyl, thiophenyl, furanyl, thiazolyl, oxazolyl, pyrazolyl, 1,2,4- or 1,2,3-triazolyl, oxadiazolyl, thiadiazolyl, isoxazolyl, isothiazolyl, pyrazinyl, pyridazinyl, pyrimidinyl, pyridinyl, benzofuranyl, benzothiophenyl, benzimidazolyl, benzothiazolyl, benzopyranyl, indolyl, isoindolyl, indazolyl and quinolinyl groups. Preferred heteroaryl substituents are $C_1$–$C_6$-alkyl groups, a hydroxyl group or a phenyl group.

Another subclass of compounds of this invention includes compounds of Formula I wherein G is a monovalent radical of Formula $VI_g$,

 (VI$_g$)

where $b_g$ is an integer, preferably 0, 1, 2 or 3, and $c_g$ is an integer, preferably 0 or 1. $b_g$ and $c_g$ are not both simultaneously 0. $R^{18}{}_l$ is a monovalent radical, such as a hydrogen atom, a straight-chain or branched $C_1$–$C_8$-alkyl group which can be substituted by halogen, preferably fluorine, atoms, especially a $CF_2$-moiety, a $C_3$–$C_8$-cycloalkyl group, a $C_3$–$C_8$-cycloalkyl-$C_1$–$C_4$-alkyl group, a substituted or unsubstituted aryl, preferably phenyl or naphthyl, group. Suitable aryl substituents are halogen, preferably fluorine, bromine or chlorine, atoms, $C_1$–$C_4$-alkoxy, trifluoromethyl, nitro or cyano groups, a dioxymethylene moiety, a $C_1$–$C_7$-alkoxycarbonyl moiety, a $C_1$–$C_7$-alkylsulfonyl moiety, an amino group or a $C_1$–$C_6$-dialkylamino group, where the alkyl groups can, together with the nitrogen atom, also form a 5- or 6-membered heterocycle.

G can also be a monovalent radical of Formula $VII_g$

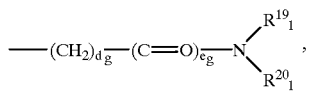 (VII$_g$)

where $d_g$ is an integer, preferably 0, 1, 2 or 3, and $e_g$ is an integer such as 0 or 1. d and e cannot both simultaneously take the value 0. $R^{19}{}_l$ and $R^{20}{}_l$ are each, independently, a monovalent radical, such as a hydrogen atom, a straight-chain or branched $C_1$–$C_8$-alkyl group, which can further be substituted by halogen, preferably fluorine, atoms, especially a $CF_2$-moiety, a $C_3$–$C_8$-cycloalkyl group, a $C_3$–$C_8$-cycloalkyl-$C_1$–$C_4$-alkyl group, a substituted or unsubstituted aryl, preferably phenyl or naphthyl group. Suitable aryl substituents include one or more halogen, preferably fluorine, bromine or chlorine, atoms, $C_1$–$C_4$-alkoxy, trifluoromethyl, nitro or cyano groups, a dioxymethylene moiety, a $C_1$–$C_7$-alkoxycarbonyl moiety, a $C_1$–$C_7$-alkylsulfonyl group, an amino group or a $C_1$–$C_6$-dialkylamino group, where the alkyl groups can, together with the nitrogen atom, also form a 5- or 6-membered heterocycle. $N(R^{19}{}_l)R^{20}{}_l$ can additionally form a ring system of the formula $N(CH_2)_{fg}$, where $f_g$ is an integer selected from among 4, 5 or 6.

Another subclass of compounds of this invention includes peptides of Formula I, wherein G is a monovalent radical of Formula $VIII_g$,

 (VIII$_g$)

where $g_g$ is an integer, for example, 1 or 2, and $h_g$ is 1 or 2. $R^{21}{}_l$ is a monovalent radical, preferably a methyl group, a trifluoromethyl group, an ethyl group or a phenyl group.

G can also be an alkyl- or arylcarbonylalkyl group of Formula $IX_g$,

 (IX$_g$)

where $R^{22}{}_l$ is a monovalent radical, such as a hydrogen atom, a straight-chain or branched $C_1$–$C_8$-alkyl group which can be substituted by up to six halogen, preferably fluorine, atoms, especially a $CF_2$-moiety, a $C_3$–$C_8$-cycloalkyl group, a $C_3$–$C_8$-cycloalkyl-$C_1$–$C_4$-alkyl group, a substituted or unsubstituted aryl, preferably phenyl or naphthyl, group. Suitable aryl substituents are halogen, preferably fluorine, bromine or chlorine, atoms, $C_1$–$C_4$-alkoxy, trifluoromethyl, nitro or cyano groups, a dioxymethylene moiety, a $C_1$–$C_7$-alkoxycarbonyl moiety, a $C_1$–$C_7$-alkylsulfonyl moiety, an amino group or a $C_1$–$C_6$-dialkylamino group, where the alkyl groups can, together with the nitrogen atom, also form a 5- or 6-membered heterocycle.

Synthetic Methods

The compounds of the present invention can be prepared by known methods of peptide synthesis. Thus, the peptides can be assembled sequentially from individual amino acids or by linking suitable small peptide fragments. In sequential assemblage, the peptide chain is extended stepwise, starting at the C-terminus, by one amino acid per step. In fragment coupling, fragments of different lengths can be linked together, and the fragments in turn can be obtained by sequential assembly from amino acids or by fragment coupling of still shorter peptides.

In both sequential assemblage and fragment coupling it is necessary to link the units by forming an amide linkage, which can be accomplished via a variety of enzymatic and chemical methods. Chemical methods for forming the amide linkage are described in detail in standard references on peptide chemistry, including Müller, *Methoden der organischen Chemie* Vol. XV/2, pages 1–364, Thieme Verlag, Stuttgart, Germany (1974); Stewart and Young, *Solid Phase Peptide Synthesis*, pages 31–34 and 71–82, Pierce Chemical Company, Rockford, Ill. (1984); Bodanszky et al., *Peptide Synthesis*, pages 85–128, John Wiley & Sons, New York, (1976). Preferred methods include the azide method, the symmetric and mixed anhydride method, the use of in situ generated or preformed active esters, the use of urethane protected N-carboxy anhydrides of amino acids and the formation of the amide linkage using coupling reagents, such as carboxylic acid activators, especially dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl) carbodiimide hydrochloride (EDCI), n-propane-phosphonic anhydride (PPA), N,N-bis(2-oxo-oxazolidinyl)imidophosphoryl chloride (BOP-Cl), bromo-tris-pyrrolidinophosphonium hexafluorophosphate (PyBrop), diphenyl-phosphoryl azide (DPPA), Castro's reagent (BOP, PyBop), O-benzotriazolyl-N,N,N', N'-tetramethyluronium salts (HBTU), diethylphosphoryl cyanide (DEPCN), 2,5-diphenyl-2,3-dihydro-3-oxo-4-hydroxy-thiophene dioxide (Steglich's reagent; HOTDO), and 1,1'-carbonyldiimidazole (CDI). The coupling reagents can be employed alone or in combination with additives such as N,N-dimethyl-4-aminopyridine (DMAP), N-hydroxybenzotriazole (HOBt), N-hydroxybenzotriazine (HOOBt), N-hydroxysuccinimide (HOSu) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques are preferred for chemical peptide synthesis: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, *Methoden der organischen Chemie* Vol. XV/1, pp 20–906, Thieme Verlag, Stuttgart (1974). The units employed for assembling the peptide chain can be reacted in solution, in suspension or by a method similar to that described by Merrifield (*J. Am. Chem. Soc.* 85: 2149 (1963)). Particularly preferred methods are those in which peptides are assembled sequentially or by fragment coupling using the Z, Boc or Fmoc protective group technique, with one of the reactants in the said Merrifield technique being bonded to an insoluble polymeric support (also called resin hereinafter). This typically entails assembling the peptide sequentially on the polymeric support using the Boc or Fmoc protective group technique, with the growing peptide chain covalently bonded at the C terminus to the insoluble resin particles. This procedure allows the removal of reagents and byproducts by filtration, eliminating the need to recrystallize intermediates.

The protected amino acids can be linked to any suitable polymer, which must be insoluble in the solvents used and have a stable physical form which permits filtration. The polymer must contain a functional group to which the first protected amino acid can be covalently attached. A wide variety of polymers are suitable for this purpose, including cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl resin (Pam-resin), p-benzyloxy-benzyl-alcohol-resin, benzhydryl-amine-resin (BHA-resin), 4-(hydroxymethyl)-benzoyl-oxymethyl-resin, the resin of Breipohl et al. (*Tetrahedron Letters* 28 (1987) 565; supplied by BACHEM), 4-(2,4-dimethoxyphenylaminomethyl) phenoxy resin (supplied by Novabiochem) or o-chlorotrityl-resin (supplied by Biohellas).

Solvents suitable for peptide synthesis include any solvent which is inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of these solvents.

Peptide synthesis on the polymeric support can be carried out in a suitable inert organic solvent in which the amino acid derivatives starting materials are soluble. However, preferred solvents additionally have resin-swelling properties and include DMF, DCM, NMP, acetonitrile, DMSO, and mixtures of these solvents. Following synthesis, the peptide is removed from the polymeric support. The conditions under which this cleavage is accomplished for various resin types are disclosed in the literature. The cleavage reactions most commonly used are acid- or palladium-catalyzed, the former being conducted in, for example, liquid anhydrous hydrogen fluoride, anhydrous trifluoromethanesulfonic acid, dilute or concentrated trifluoroacetic acid, and acetic acid/dichloromethane/trifluoroethanol mixtures. The latter can be carried out in THF or THF-DCM-mixtures in the presence of a weak base such as morpholine. Certain protecting groups are also cleaved off under these conditions.

Partial deprotection of the peptide may also be necessary prior to certain derivatization reactions. For example, peptides dialkylated at the N-terminus can be prepared either by coupling the appropriate N,N-di-alkylamino acid to the peptide in solution or on the polymeric support or by reductive alkylation of the resin-bound peptide in DMF/1% acetic acid with NaCNBH$_3$ and the appropriate aldehyde.

The two schemes which follow present a more detailed description of the synthesis of the compounds of the present invention.

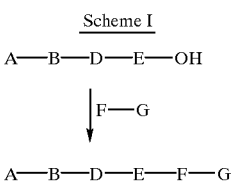

The tetrapeptide A-B-D-E-OH is coupled with an amino-derivative F-G to give the final compound A-B-D-E-F-G using the methods for peptide coupling as described above.

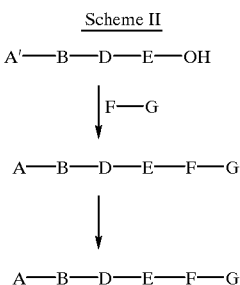

Here, the N-terminal protected tetrapeptide A'-B-D-E-OH is coupled with an amino-derivative F-G to give an intermediate compound A'-B-D-E-F-G using the methods for peptide coupling as described above. Then, the N-protecting group is removed by conventional methods as described above. The groups $R_A$ and $R^7_A$ can then be attached to the amino terminus via reductive alkylation as described above.

Building blocks of use in the synthesis of the claimed compounds (described in scheme I and II as F-G) can be prepared by the following general methods:

a) Synthesis of amino-phenyl-ketones

The following schemes describe synthetic routes to aminophenyl-ketones which are not commercially available.

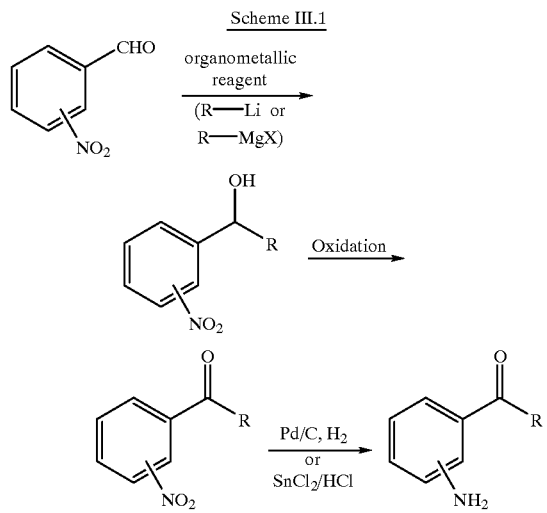

In scheme III.1, the synthesis starts with a nitrobenzaldehyde. Addition of organometallic compounds such as lithium or Grignard reagents led to the corresponding alcohols (Fürstner et al. *Tetrahedron* 52: 7329–7344 (1996); F ürstner et al., *Tetrahedron* 51, 773–786 (1995)). These alcohols can be oxidised to the ketones with known oxidation agents, such as chromium(VI) compounds (for example, pyridinium dichromate in dichloromethane, as described by Fürstner et al., supra) or the Dess Martin reagent. The nitrophenyl ketones are then reduced to the corresponding amino-phenyl-ketones either by hydrogenation in presence of a palladium catalyst, such as palladium on carbon, or by metal salts in presence of acids such as the combination of tin(II)chloride and hydrochloric acid (Nunn et al., *J. Chem. Soc.* 1952: 583–588).

2-Amino-phenyl ketones can be obtained by reaction of the corresponding 2-fluorophenyl-ketone with sodium azide in a polar solvent, such as N,N-dimethylformamide, and subsequent reduction of the intermediate benzisoxazole (see scheme III.3). For example, the synthesis of 2-aminophenyl-(4-pyridazinyl)-ketone has been described by N. Haider et al. (*Arch. Pharm.* 325: 119–122 (1992)).

b) synthesis of amino-benzamides

The following schemes describe synthetic routes to aminobenzamides which are not commercially available.

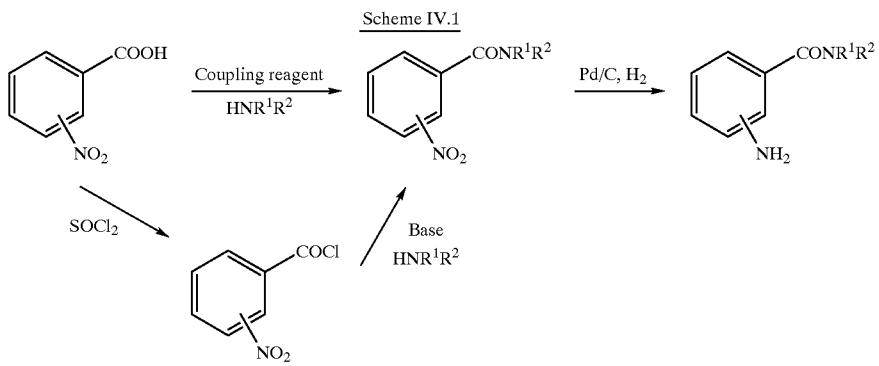

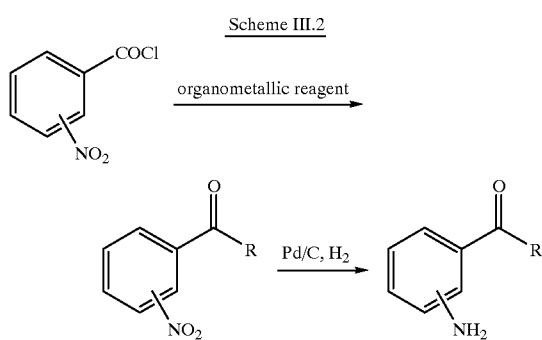

In scheme IV.1, the steps are described starting from nitrobenzoic acids or substituted nitrobenzoic acids. These acids are coupled with primary or secondary amines (HNR$^1$R$^2$) by using coupling reagents. Preferred method is the use of coupling reagents such as carboxylic acid activators, especially dicyclohexylcarbodiimide (DCC), diisopropyl-carbodiimide (DIC), 1-ethoxycarbonyl-2-ethoxy-1,2-dihydroquinoline (EEDQ), pivaloylchloride, 1-ethyl-3-(3-dimethylaminopropyl)carbodiimide hydrochloride (EDCI), n-propane-phosphonic anhydride (PPA), N,N-bis(2-oxo-3 oxazolidinyl)-imidophosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), diethylphosphoryl cyanide (DEPCN), 2,5-diphenyl 2,3-dihydro-3-oxo-4-hydroxythiophene dioxide (Steglich's reagent; HOTDO) and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxybenzotriazine (HOOBt), azabenzotriazole, N-hydroxysuccinimide (HOSU) or 2-hydroxypyridine.

In place of the acids, the corresponding nitro-benzoyl chloride can be used. These are either commercially available or could be synthesized from the corresponding acids with thionyl chloride. The amines react with the nitrobenzoylchlorides in the presence of a base such as pyridine, which can also be used as the solvent (N. S. Cho et al., *J. Heterocycl. Chem.* 33, 1201–1206 (1996)). The nitrobenzamides are then reduced to the corresponding aminobenzamides by reducing agents such as metal salts in presence of hydrochloride acids or by metal-catalysed hydrogenation using palladium on a solid such as palladium on charcoal as catalyst. This route is described in Example 1.

Another method involves transforming the amine to the trifluoroacetamide by treatment with trifluoroacetic anhy- A more direct route (see scheme III.2) is the reaction of nitrobenzoyl chlorides with an organometallic reagent such as a lithium or Grignard reagent (Fürstner et al., *Tetrahedron* 51, 773–786 (1995)).

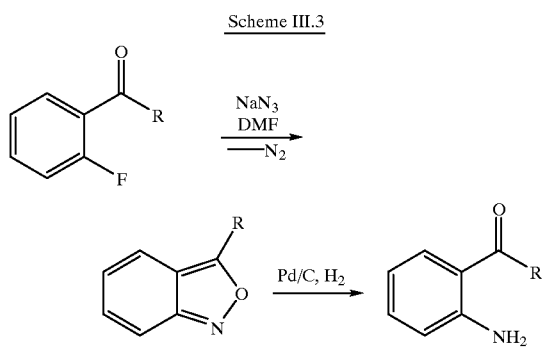

dride. The amide is deprotonated with a base such as sodium hydride or potassium t-butanolate and then treated with the corresponding alkyl halide such as methyl iodide, ethyl iodide or isopropyl iodide. The trifluoroacetamide is easily cleaved in basic alcoholic solution such as potassium carbonate in methanol.

Scheme IV.2

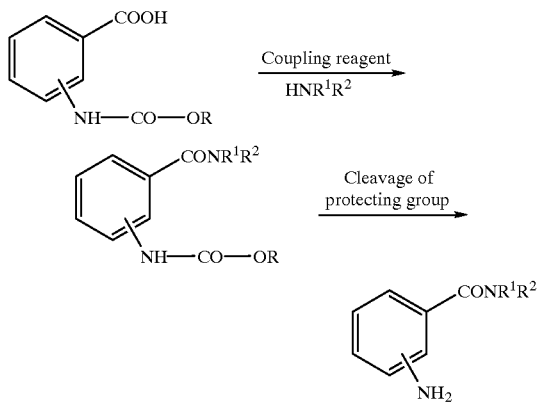

In scheme IV.2. the starting materials for the synthesis of amino-benzamides are the N-protected aminobenzoic acids. Different protecting groups for the nitrogen are compatible such as the above mentioned Z-, Boc- or Fmoc-protecting groups. The N-protected amino-benzoic acids are coupled with amines as described above for the nitro-benzoic acids using the above mentioned coupling conditions. This route exemplified in Example 2.

Scheme IV.3

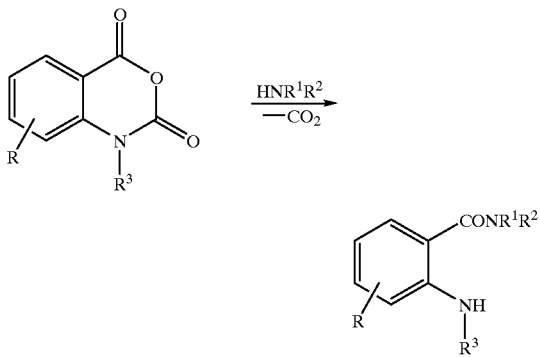

A route for the preparation of 2-aminobenzamides is described in scheme IV.3. Opening of isatoic anhydride (substituted or unsubstituted at the nitrogen) by amines with evolution of carbon dioxide led to the corresponding 2-amino-benzamides, as described by Clark et al., *J. Org. Chem.* 9: 55–64 (1944).

c) Amino-cyclopentane- or aminocyclohexane-carboxamides

Different routes have been described to the synthesis of cis-2-amino-cyclopentylcarboxylic acid (cispentacin) in racemic form or as pure enantiomer. Using an intramolecular nitrone-olefin cycloaddition cis-2-(t-butoxycarbonylamino) cyclopentane-1-carboxylic acid could be prepared in a few synthetic steps (Konosu et al., *Chem. Pharm. Bull.* 41: 1012 (1993)). Another route to enantiomerically pure cis-(1R, 2S)-2-amino-cyclopentylcarboxylic acid is the addition of chiral lithium (S)-(-methylbenzyl)benzylamide to t-butyl-1-cyclopentene-1-carboxylate with subsequent removal of the benzyl groups by hydogenation and removal of the t-butyl group by acid treatment (Davies et al., *Synlett* 1993, p. 461). The corresponding trans-epimer could be obtained by isomerisation with a base such as potassium t-butoxide. By using the lithium (R)-(-methylbenzyl)benzylamide in the Michael addition (is, 2R)-2-amino-cyclopentylcarboxylic acid and (1S, 2S)-2-amino-cyclopentylcarboxylic acid can be obtained. This method is also applicable to the synthesis of cis-and trans-aminocyclohexane-1-carboxylic acid.

Resolution of racemic Boc-protected cis-2-aminocyclopentane carboxylic acid (Bernath et al., *Acta Chim.* 74: 479 (1972); Nativ et al., *Isr. J. Chem.* 10: 55 (1972)) can be achieved with (+)- and (−)-ephedrine in high enantiomeric excess (Nöteberg et al., *Tetrahedron* 53: 7975 (1997)). In this paper also the synthesis of the trans-enantiomers of Boc-protected trans-2-aminocyclopentane carboxylic methyl ester was described, starting with either trans-(3R, 4R) -bis(methoxycarbonyl)cyclopentanone or trans(3S, 4S) -bis(methoxycarbonyl)-cyclopentanone.

Amides of Boc-protected 2-aminocyclopentylcarboxylic acid can be obtained by coupling the acid with the corresponding amine using the standard procedures as described above for the coupling of nitrobenzoic acid with amines or as described in D. Nöteberg et al., *Tetrahedron* 53: 7975 (1997). Deprotection of the amine function can be achieved by using Lewis acids, for example, a mineral acid such as hydrochloric acid in ether or dioxane or an organic acid, such as trifluoroacetic acid in methylene chloride.

Methods of Use of the Claimed Compounds

In another embodiment, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrial tumors) or hematological malignancies (e.g., leukemias, lymphomas) in a mammal, for example, a human, by administering to the mammal a therapeutically effective amount of a compound or a combination of compounds of Formula I. The agent may be administered alone or in a pharmaceutical composition comprising the agent and an acceptable carrier or diluent. Administration may be by any of the means which are conventional for pharmaceutical, preferably oncological, agents, including oral and parenteral means such as subcutaneously, intravenously, intramuscularly and intraperitoneally, nasally or rectally. The compounds may be administered alone or in the form of pharmaceutical compositions containing a compound of Formula I together with a pharmaceutically accepted carrier appropriate for the desired route of administration. Such pharmaceutical compositions may be combination products, i.e., they may also contain other therapeutically active ingredients.

The dosage to be administered to the mammal, such as a human, will contain a therapeutically effective amount of a compound described herein. As used herein, "therapeutically effective amount" is an amount sufficient to inhibit (partially or totally) formation of a tumor or a hematological malignancy or to reverse development of a solid tumor or other malignancy or prevent or reduce its further progression. For a particular condition or method of treatment, the dosage is determined empirically, using known methods, and will depend upon factors such as the biological activity of the particular compound employed; the means of administration; the age, health and body weight of the recipient; the nature and extent of the symptoms; the frequency of treatment; the administration of other therapies; and the effect desired. A typical daily dose will be from about 5 to about 250 milligrams per kilogram of body weight by oral administration and from about 1 to about 100 milligrams per kilogram of body weight by parenteral administration.

The compounds of the present invention can be administered in conventional solid or liquid pharmaceutical administration forms, for example, uncoated or (film-) coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/ or propellant gases (cf. H. Sücker et al.: *Pharmazeutische Technologie*, Thieme-Verlag, Stuttgart, 1978). The administration forms obtained in this way typically contain from about 1 to about 90% by weight of the active substance.

The following examples are intended to illustrate the invention but are not to be considered limitations of the invention.

EXAMPLES

The proteinogenous amino acids are abbreviated in the examples using the known three-letter code. Other abbreviations employed are: TFA=trifluoroacetic acid, Ac=acetic acid, DCM=dichloromethane, DMSO=dimethylsulfoxide, Bu=butyl, Et=ethyl, Me=methyl, Bn=benzyl. In the compounds listed, all proteinogenous amino acids are L-amino acids unless otherwise noted.

General Materials and Methods

The compounds of the present invention are synthesized by classical solution synthesis using standard Z- and Boc-methodology as discussed above or by standard methods of solid-phase synthesis on a model 431A synthesizer supplied by APPLIED BIOSYSTEMS. This apparatus uses different synthetic cycles for the Boc and Fmoc protective group techniques, as described below.

| Synthetic cycle for the Boc protecting group technique | |
|---|---|
| 1. 30% trifluoroacetic acid in DCM | 1 × 3 min |
| 2. 50% trifluoroacetic acid in DCM | 1 × 1 min |
| 3. DCM washing | 5 × 1 min |
| 4. 5% diisopropylethylamine in DCM | 1 × 1 min |
| 5. 5% diisopropylethylamine in NMP | 1 × 1 min |
| 6. NMP washing | 5 × 1 min |
| 7. Addition of preactivated protected amino acid (activation with 1 equivalent of DCC and 1 equivalent of HOBt in NMP/DCM); Peptide coupling (1st part) | 1 × 30 min |
| 8. Addition of DMSO to the reaction mixture until it contains 20% DMSO by volume | |
| 9. Peptide coupling (2nd part) | 1 × 16 min |
| 10. Addition of 3.8 equivalents of diisopropylethylamine to the reaction mixture | |
| 11. Peptide coupling (3rd part) | 1 × 7 min |
| 12. DCM washing | 3 × 1 min |
| 13. if conversion is incomplete, repetition of coupling (back to step 5) | |
| 14. 10% acetic anhydride, 5% diisopropylethylamine in DCM | 1 × 2 min |
| 15. 10% acetic anhydride in DCM | 1 × 4 min |
| 16. DCM washing | 4 × 1 min |
| 17. back to step 1. | |

BOP-Cl and PyBrop were used as reagents for coupling an amino acid to an N-methylamino acid. The reaction times were correspondingly increased. In solution synthesis, the use of either Boc-protected amino acid NCAs (N-tert-butyloxycarbonyl-amino acid-N-carboxy-anhydrides) or Z-protected amino acid NCAs (N-benzyloxycarbonyl-amino acid-N-carboxy-anhydrides) respectively is most preferable for this type of coupling.

| Synthetic cycle for the Fmoc protective group technique | |
|---|---|
| 1. DMF washing | 1 × 1 min |
| 2. 20% piperidine in DMF | 1 × 4 min |
| 3. 20% piperidine in DMF | 1 × 16 min |
| 4. DMF washing | 5 × 1 min |
| 5. Addition of the preactivated protected amino acid (activation by 1 equivalent of TBTU and 1.5 equivalent of DIPEA in DMF); Peptide coupling | 1 × 61 min |
| 6. DMF washing | 3 × 1 min |
| 7. If conversion is incomplete, repetition of coupling (back to 5.) | |
| 8. 10% acetic anhydride in DMF | 1 × 8 min |
| 9. DMF washing | 3 × 1 min |
| 10. back to 2. | |

BOP-Cl and PyBrop were used as reagents for coupling an amino acid to an N-methylamino acid. The reaction times were correspondingly increased. Reductive alkylation of the N terminus The peptide-resin prepared as described above was deprotected at the N terminus and then reacted with a 3-fold molar excess of aldehyde or ketone in DMF/1% acetic acid with addition of 3 equivalents of NaCNBH$_3$. After reaction was complete (negative Kaiser test), the resin was washed several times with water, isopropanol, DMF and dichloromethane.

Workup of the Peptide-Resins

The peptide-resin obtained via the Boc protecting group technique was dried under reduced pressure and transferred into a reaction vessel of a TEFLON HF apparatus (supplied by PENINSULA). A scavenger, usually anisole (1 mL/g of resin), was then added and additionally, in the case of tryptophan-containing peptides, a thiol (0.5 mL/g of resin), preferably ethanedithiol, to remove the indolic formyl group. This was followed by condensing in hydrogen fluoride (10 mL/g of resin) in a bath of liquid $N_2$. The mixture was allowed to warm to 0° C. and stirred at this temperature for 45 min. The hydrogen fluoride was then stripped off under reduced pressure, and the residue was washed with ethyl acetate to remove any remaining scavenger. The peptide was extracted with 30% acetic acid and filtered, and the filtrate was lyophilized.

The peptide-resin formed by the Fmoc protecting group method was dried under reduced pressure and then subjected to one of the following cleavage procedures, depending upon the amino-acid composition (Wade, Tregear, Howard Florey Fmoc Workshop Manual, Melbourne 1985). The suspension of the peptide-resin in the suitable TFA mixture was stirred at room temperature for the stated time and then the resin was filtered off and washed with TFA and DCM. The filtrate and the washings were concentrated, and the peptide was precipitated by addition of diethyl ether. After cooling in an ice bath, the precipitate was filtered off, taken up in 30% acetic acid and lyophilized.

When an o-chlorotrityl-resin (supplied by Biohellas) was used, the suspension of the peptide-resin in an acetic acid/ trifluoroethanol/dichloromethane mixture (1:1:3) was stirred at room temperature for 1 h. The suspension was then filtered with suction and the peptide-resin was thoroughly washed with the cleavage solution. The combined filtrates were concentrated in vacuo and treated with water. The precipitated solid was removed by filtration or centrifugation, washed with diethyl ether and dried under reduced pressure.

Purification and Characterization of the Peptides

Purification was carried out by gel chromatography (SEPHADEX G-10, G-15/10% HOAc, SEPHADEX LH20/MeOH) with or without subsequent medium pressure chromatography (stationary phase: HD-SIL C-18, 20–45 m, 100 Å; mobile phase: gradient with A=0.1% TFA/MeOH, B=0.1% TFA/H$_2$O). The purity of the resulting products was determined by analytical HPLC (stationary phase: 100 2.1 mm VYDAC C-18, 5 1, 300 Å; mobile phase: CH$_3$CN/H$_2$O gradient, buffered with 0.1% TFA, 40%C).

The polypeptides were characterized by amino-acid analysis and fast atom bombardment mass spectroscopy.

Example 1

Synthesis of (2)-(Me$_2$Val-Val-MeVal-Pro-NH)-C$_6$H$_4$-CON(CH$_3$)$_2$ (Compound I-78)

Me$_2$Val-Val-MeVal-Pro-OH and Z-Val-Val-MeVal-Pro-OH were prepared by the method disclosed in patent applications DE 4415998 and DE 19527575, the contents of which are incorporated herein by reference.

a) Synthesis of N,N-dimethyl-2-nitrobenzamide

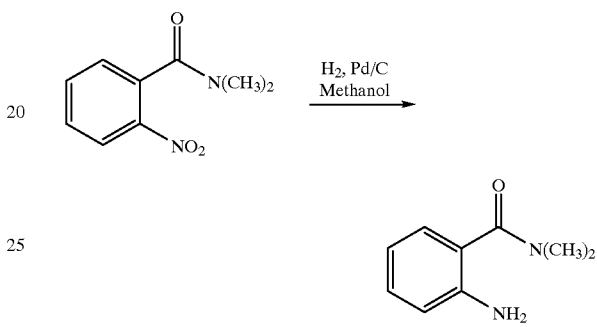

To a solution of 2.0 g 2-nitrobenzoic acid and 0.98 g dimethylammonium chloride in dichloromethane at 0° C. were added 2.29 g 1-ethyl-3-(3-dimethylaminopropyl) carbodiimide hydrochloride, 1.62 g N-hydroxy-benzotriazol and 6.05 g N-methyl-morpholine. The resulting mixture was stirred at room temperature overnight. The reaction mixture was then washed sequentially, with saturated sodium hydrogen carbonate, a 5% aqueous solution of citric acid and brine. The organic phase was dried over sodium sulfate. After filteration the solvent was removed in vacuo yielding N,N-dimethyl-2-nitrobenzamide (2.13 g).

$^1$H-NMR (DMSO, 270 MHz) d 2.7 (s, 3 H), 3.0 (s, 3 H), 7.5 (d, 1 H), 7.7 (dd, 1 H), 7.85 (dd, 1 H)., 8.15 (d, 1 H) ppm b) Synthesis of N,N-dimethyl-2-aminobenzamide

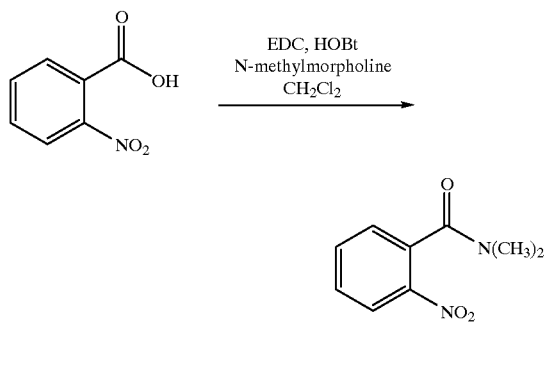

Palladium on charcoal (0.54 g, 10% Pd by weight) was added to a solution of 2.1 g N,N-dimethyl-2-nitrobenzamide in 150 mL methanol. The resulting suspension was hydrogenated at room temperature at atmospheric pressure for three hours. After filtration of the catalyst, the solvent was removed in vacuo affording N,N-dimethyl-2-aminobenzamide (1.8 g).

$^1$H-NMR (DMSO, 270 MHz) d=2.9 (s, 6 H), 5.1 (s, 2 H), 6.5 (dd, 1 H) , 6.65 (d, 1 H) , 7.95 (d, 1 H) , 7.0 (dd, 1 H) ppm c) Synthesis of (2)-(Z-Val-Val-MeVal-Pro-NH) -C$_6$H$_4$-CON(CH$_3$)$_2$

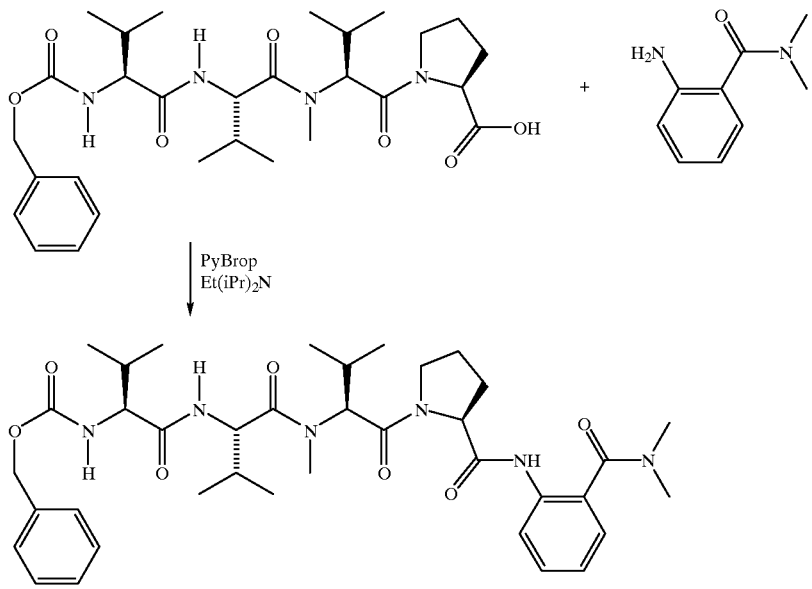

To a solution of 2.0 g Z-Val-Val-MeVal-Pro-OH and 0.53 g N,N-dimethyl-2-amino-benzamide in dichloromethane was added 1.66 g bromo-tris-pyrrolidinophosphonium hexafluorophosphate (PyBrop) and 0.77 g N-ethyldiisopropylamine at 0° C. The mixture was stirred at room temperature overnight, and then washed sequentially with saturated sodium hydrogen carbonate, a 5% aqueous solution of citric acid, and brine. The organic phase was dried over sodium sulfate. After filtration, the solvent was removed in vacuo. The residue was purified by silica gel chromatography (1:3 dichloromethane:ethyl acetate) to provide (2)-(Z-Val-Val-MeVal-Pro-NH)-C$_6$H$_4$-CON(CH$_3$)$_2$ (1.8 g). FAB-MS 707.0 (M+H+d)

d) Synthesis of 2-(Me$_2$Val-Val-MeVal-Pro-NH)-C$_6$H$_4$-CON(CH$_3$)$_2$

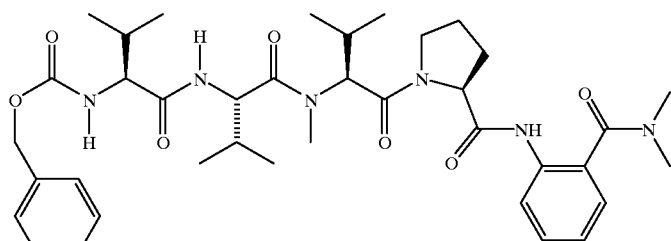

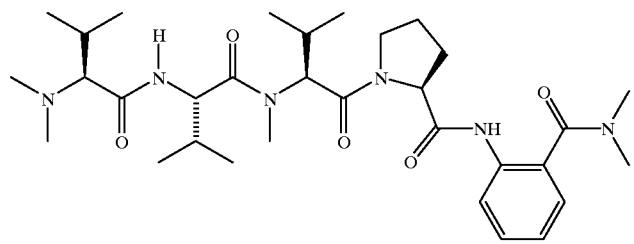

Palladium on charcoal (58 mg, 10% Pd by weight) was added to a solution of 1.8 g 2-(Z-Val-Val-MeVal-Pro-NH)-C$_6$H$_4$-CON(CH$_3$)$_2$ in 150 mL methanol. The resulting suspension was hydrogenated at room temperature at atmospheric pressure for three hours, then 1.5 mL of an aqueous formaldehyde solution (37% formaldehyde by weight) and 341 mg of palladium on charcoal were added. The mixture was hydrogenated at room temperature at atmospheric pressure overnight. After filtration over celite the solvent was removed in vacuo to give 1.30 g 2-(Me$_2$Val-Val-MeVal-Pro-NH)-C$_6$H$_4$ -CON(CH$_3$)$_2$. FAB-MS: 601.0 (M+H$^+$)

$^1$H-NMR (DMSO, 270 MHz) d=0.7 (s, 6 H), 0.8–1.0 (m, 12 H), 1.75 (m, 1 H), 1.8–2.2 (m, 6 H), 2.2 (s, 6 H), 2.6 (d, 1 H), 2.8 (s, 3 H), 2.9 (s, 3 H), 3.05 (s, 3 H), 3.55, 3.7 (m, 2 H), 4.4 (m, 1 H), 4.5 (m, 1 H), 5.0 (d, 1 H), 7.2 (dd, 1 H), 7.25 (d, 1 H), 7.4, dd, 1 H), 7.6 (dd, 1 H), 8.0 (d, 1 H), 9.6 (s, 1H)

Example 2
Synthesis of (2)-(Me$_2$Val-Val-MeVal-Pro-NH)-C$_6$H$_4$-CON(CH$_3$) (OCH$_3$) (Compound I-60)

a) Synthesis of N,O-dimethyl-(2-N-tert. butoxycarbonyl-amino)benzohydroxylamide

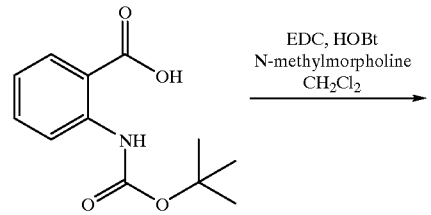

-continued

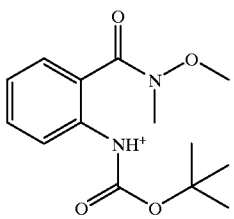

To a solution of 1.5 g 2-N-t-butoxy-carbonyl anthranilic acid and 0.68 g N,O-dimethylhydroxylamine hydrochloride in dichloromethane at 0° C., 1.33 g 1-ethyl-3-(3-dimethylaminopropyl) carbodiimide hydrochloride, 0.94 g N-hydroxybenzotriazol and 3.20 g N-methylmorpholine were added. The mixture was stirred at room temperature overnight. The reaction mixture was washed sequentially with saturated aqueous sodium hydrogen carbonate, a 5% aqueous solution of citric acid and brine. The organic phase was dried over sodium sulfate. After filtration the solvent was removed in vacuo. Flash chromatography (silica gel, heptane:ethyl acetate 10:1) afforded N,O-dimethyl-(2-N-tert. Butoxycarbonyl-amino) benzohydroxylamide (1.18 g).

$^1$H-NMR (CDCl$_3$, 270 MHz) d=1.5 (s, 9 H), 3.4 (s, 3 H), 3.6 (s, 3 H), 7.0 (dd, 1 H), 7.2–7.4 (m, 2 H), 8.1 (d, 1 H), 8.4 (s, 1 H)

b) Synthesis of N,O-dimethyl-(2-amino) benzohydroxylamide hydrochloride.

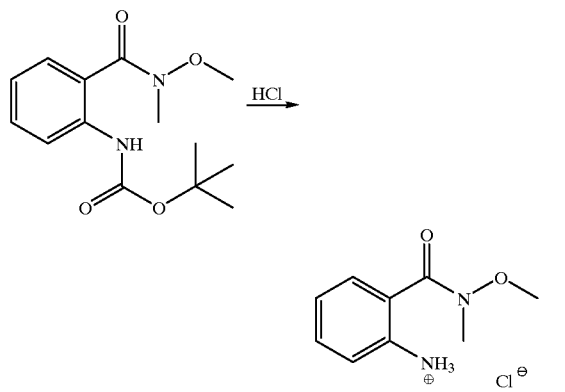

To a solution of 0.5 g N,O-dimethyl-(2-N-tert. butoxycarbonyl-amino)benzohydroxylamide in 15 mL dichloromethane at 0° C. was added 17 mL of a hydrogen chloride solution in ether and the resulting solution was stirred for 2 hours. The solvent was evaporated to give 0.41 g N,O-dimethyl-(2-amino)benzohydroxylamide hydrochloride.

$^1$H-NMR (CDCl$_3$, 270 MHz) d=3.4 (s, 3 H), 3.6 (s, 3 H), 7.3 (dd, 1 H), 7.5(dd, 2 H), 7.6 (d, 1 H), 7.9 (d, 1 H)

c) Synthesis of (2)-(Me$_2$Val-Val-MeVal-Pro-NH)-C$_6$H$_4$-CON(CH$_3$) (OCH$_3$)

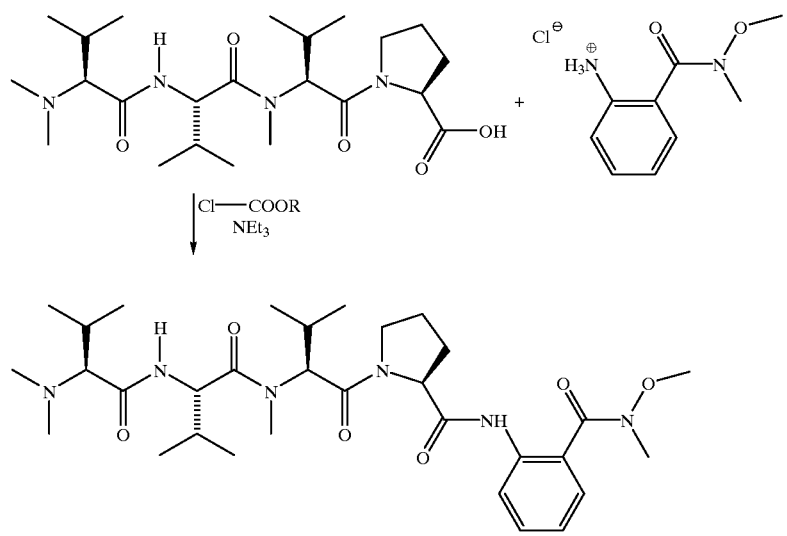

To a solution of 0.892 g Me$_2$Val-Val-MeVal-Pro-OH and 0.234 g triethylamine in 10 mL dichloromethane at 0° C. was added 0.218 g formate. After stirring the resulting mixture for two hours, 0.41 g N,O-dimethyl-(2-amino) benzohydroxylamide hydrochloride and 0.234 g triethylamine were added and the mixture was stirred overnight at room temperature. The reaction mixture was washed sequentially with saturated sodium hydrogen carbonate solution and brine. The organic phase was dried over sodium sulfate. After filtration the solvent was removed in vacuo. The residue was purified by chromatography (silica gel treated with 1% triethylamine, solvent: dichloromethane/3% isopropanol) to provide 0.28 g (2)-(Me$_2$Val-Val-MeVal-Pro-NH)-C$_6$H$_4$-CON(CH$_3$) (OCH$_3$). FAB-MS: 617.5 (M+H$^+$)

$^1$H-NMR (DMSO, 270 MHz) d=0.7 (s, 6 H), 0.8–1.0 (m, 12 H), 1.7 (m, 1 H), 1.8–2.2 (m, 6 H), 2.2 (s, 6 H), 2.6 (d, 1 H), 3.0 (s, 3 H), 3.2 (s, 3 H), 3.5 (s, 3 H), 3.5, 3.7 (m, 2 H), 4.4 (m, 1 H), 4.5 (m, 1 H), 5.0 (d, 1 H), 7.2 (dd, 1 H), 7.3–7.5 (m, 2 H), 7.6 (dd, 1 H), 8.0 (d, 1 H), 9.65 (s, 1H)

Example 3

Synthesis of Me$_2$Val-Val-MeVal-Pro-[cis-2-aminocyclopentanecarboxylic acid]-NHBn (Compound VII-2)

d) Synthesis of racemic cyclopentane-cis-1,2-dicarboxylic acid anhydride

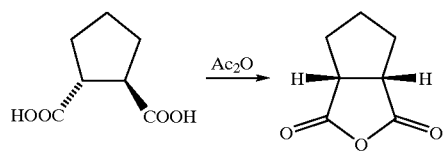

8.4 g (44.3 mmol) of commercially available cyclopentane-trans-1,2-dicarboxylic acid was refluxed for 20 h in 75 ml of acetic acid anhydride, then evaporated and the obtained residue distilled in a "Kugelrohr-apparatus" at 1.0 mbar. The fraction boiling at 1650 was collected, yielding 5.8 g of the product as an oil.

$^{13}$C-NMR (400 MHz; DMSO-d$_6$) d (ppm): 25.3 (C-4), 30.6 (C-3,5), 45.7 (C-1,2), 175.6 (C-6,7).

b) Synthesis of racemic cis-2-carbamoylcyclopentanecarboxylic acid

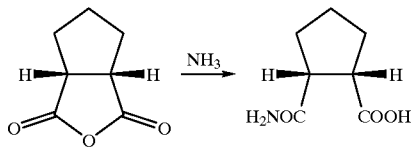

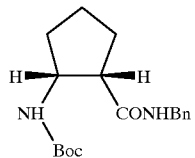

1.1 g (7.85 mmol) of cyclopentane-cis-1,2-dicarboxylic acid anhydride were added to 8 ml of an aqueous NH$_3$-solution and stirred until dissolution of the educt. The excess of ammonia was then evaporated, the remaining solution cooled to 0° C. and acidified with conc. HCl. The resulting precipitate was filtered off, washed with cold water and dried, yielding 0.7 g of cis-2-carbamoylcyclopentanecarboxylic acid with a melting point of 132–133° C. (lit.: 126–128° C.).

c) Synthesis of racemic cis-2-aminocyclopentanecarboxylic acid

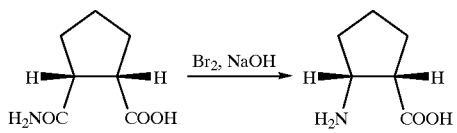

Under stirring at 0° C. 0.41 g (2.6 mmol) of Br$_2$ were added to an aqueous solution (1.8 mL) of 0.48 g (12 mmol) NaOH. The mixture was cooled again and then 0.34 g (2.16 mmol) of cis-2-carbamoylcyclopentanecarboxylic acid added. After stirring for about 10 minutes again 0.35 g (8.65 mmol) NaOH—dissolved in 1.35 ml of water were added, and then the whole mixture warmed to 75° C. for about 5 minutes. The mixture then was cooled again, neutralized by addition of conc. HCl, acidified with acetic acid and evaporated to dryness. The residue obtained was extracted five times with refluxing ethanol, and the combined ethanol-fractions evaporated again yielding 1.1 g of a white solid.

Purification was achieved by filtration of this residue over a column with Dowex 50 ion exchange resin. Therefore the column was washed with a solution of the solid in water, and then the product eluted by treatment with solid was dissolved in water and the column, absorbed on by washing the column with aqueous diluted NH$_3$. After evaporation of the water the remaining crude product was recrystallized from acetone yielding 0.14 g of pure cis-2-aminocyclopentanecarboxylic acid with a melting point of 200–202° C.

d) Synthesis of racemic cis-2-t-butyloxycarbonylaminocyclopentanecarboxylic acid benzylamide

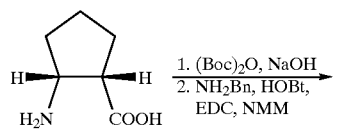

To a solution of 1.5 g (11.6 mmol) of cis-2-aminocyclopentanecarboxylic acid in a mixture of acetonitrile/water 3:1 were added 3.3 g (15.1 mmol) of di$^t$butyldicarbonate, 0.5 g (12.2 mmol) of NaOH dissolved in 12 ml of H$_2$O and 0.1 g (0.82 mmol) of DMAP. The mixture was stirred at ambient temperature for about 3 days, then diluted with water, extracted with ethylacetate. The combined organic phases were washed with a saturated aqueous NaCl-solution, dried over MgSO$_4$ and evaporated to dryness leaving 1.3 g of the Boc-protected compound as an oil. A solution of the crude product and 0.65 g (6.1 mmol) benzylamine in a mixture of THF/DMF 10:1 was cooled to −10° C., then were added subsequently 0.9 g (5.86 mmol) of HOET, 1.12 g (5.86 mmol) of EDC×HCl and 3 ml of NMM. The mixture was stirred for 2 h at −10° C., for 3 h at 0° C. and was then allowed to warm up to room temperature. After evaporation to dryness the remaining residue was dissolved in ethylacetate, washed with aqueous solutions of 5% citric acid, NaHCO$_3$ and NaCl and dried over MgSO$_4$. Evaporation yielded 1.3 g of cis-2-t-butyloxycarbonylaminocyclopentanecarboxylic acid benzylamide as an oil. HPLC (gradient 2): R$_t$ 10.5 min. (Column: Machery & Nagel Nucleosil C18 PPN, 100×2.1, 5m/100A, acetonitrile/H$_2$O+0.1% TFA; flow: 0.2 ml/min; temp. 40° C.).

$^1$H-NMR (270 MHz; DMSO-d$_6$) d (ppm): 1.35 (s, 9H), 1.35–1.95 (m, 6H), 2.82 (m, 1H), 4.03 (m, 1H), 4.25 (m, 2H), 6.35 (d, NH), 7.1–7.35 (m, 5H), 8.3 (m, 1H).

e) Synthesis of racemic cis-2-aminocyclopentanecarboxylic acid benzylamide hydrochloride

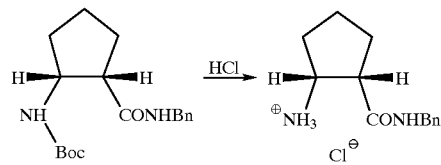

To a solution of 0.7 g (2.2 mmol) of of cis-2-tert.butyloxycarbonylaminocyclo-pentanecarboxylic acid benzylamide in 30 ml CH$_2$Cl$_2$ were added 25 ml of saturated HCl in diethylether; the mixture was then stirred for 2 h at ambient temperature. Evaporation to dryness and coevaporation with toluene yielded 0.6 g of the deprotected amine as hydrochloride salt.

f) Synthesis of Me$_2$Val-Val-MeVal-Pro-[cis-2-aminocyclopentanecarboxylic acid]-NHBn (Compound VII-2)

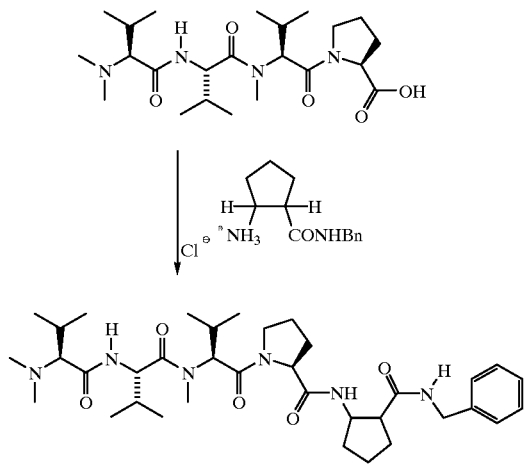

To a solution of 0.86 g (1.9 mmol) of the tetrapeptide Me$_2$Val-Val-MeVal-Pro-OH and 0.56 g (2.2 mmol) aminocyclo-pentanecarboxylic acid benzylamide hydrochloride in 30 ml of THF/DMF 5:1 were added subsequently at −10° C. 0.29 g (1.9 mmol) of HOBT; 0.37 g (1.9 mmol) of EDC×HCl and 1.2 ml of NMM The mixture was stirred for another at −10° C., then for 1–2 h at 0° C. and then allowed to warm up to ambient temperature. After evaporation the remaining residue was diluted with ethyl acetate, washed with an aqueous solution of NaCl, dried over MgSO$_4$ and evaporated again. The remaining crude product (1.2 g) was purified by flash cromatography on silica gel (CH$_2$Cl$_2$/CH$_3$OH) yielding 0.37 g of Me$_2$Val-Val-MeVal-Pro-[cis-2-aminocyclopentanecarboxylic acid]-NHBn. FAB-MS: 655 (M+H$^+$). The following compounds can be prepared as outlined in Schemes I–III and according to the above examples.

TABLE 1

A is Me$_2$Val, B is Val, D is MeVal, E is Pro, F is of Formula II$_F$ and the group —C(=O)—G is in position 2 relative to the nitrogen atom. G is of Formula II$_g$ or, III$_g$ or IV$_g$.

| No. | R$_F$ | R$^1_F$ | R$^2_F$ | —C(=O)—G |
|---|---|---|---|---|
| I-1 | H | H | H | —NH—CH$_3$ |
| I-2 | H | H | H | —NH—CH$_2$—C$_6$H$_5$ |
| I-3 | H | H | H | —NH-isoC$_3$H$_7$ |
| I-4 | H | H | H | —NH—C$_6$H$_5$ |
| I-5 | H | H | H | 1,3-Thiazol-2-yl-amide |
| I-6 | H | 4-OCH$_3$ | 5-OCH$_3$ | —NH—CH$_3$ |
| I-7 | H | 3-cycloC$_5$H$_9$ | H | —NH—CH$_3$ |
| I-8 | H | H | H | —NH—C$_2$H$_5$ |
| I-9 | H | H | H | —NH-nC$_3$H$_7$ |
| I-10 | H | H | H | —NH-nC$_4$H$_9$ |
| I-11 | H | H | H | —NH-tertC$_4$H$_9$ |
| I-12 | H | H | H | —NH-cycloC$_3$H$_5$ |
| I-13 | H | H | H | —NH-cycloC$_4$H$_7$ |
| I-14 | H | H | H | —NH-cycloC$_5$H$_9$ |
| I-15 | H | H | H | —NH-cycloC$_6$H$_{11}$ |
| I-16 | H | H | H | —NH-cycloC$_7$H$_{12}$ |
| I-17 | H | H | H | —NH—CH$_2$—O—CH$_3$ |
| I-18 | H | H | H | —NH—CH$_2$—CH$_2$—O—CH$_3$ |
| I-19 | H | H | H | —NH-1-adamantyl |
| I-20 | H | H | H | —NH-(4-HO—C$_6$H$_4$) |
| I-21 | H | H | H | —NH-(2-CF$_3$—C$_6$H$_4$) |
| I-22 | H | H | H | —NH-(3-CF$_3$—C$_6$H$_4$) |
| I-23 | H | H | H | —NH-(4-CF$_3$—C$_6$H$_4$) |
| I-24 | H | H | H | —NH-(2-OCH$_3$—C$_6$H$_4$) |
| I-25 | H | H | H | —NH-(3-OCH$_3$—C$_6$H$_4$) |
| I-26 | H | H | H | —NH-(4-OCH$_3$—C$_6$H$_4$) |

TABLE 1-continued

A is Me$_2$Val, B is Val, D is MeVal, E is Pro, F is of Formula II$_F$ and the group —C(=O)—G is in position 2 relative to the nitrogen atom. G is of Formula II$_g$ or, III$_g$ or IV$_g$.

| No. | R$_F$ | R$^1_F$ | R$^2_F$ | —C(=O)—G |
|---|---|---|---|---|
| I-27 | H | H | H | —NH-(2-SCH$_3$—C$_6$H$_4$) |
| I-28 | H | H | H | —NH-(3-SCH$_3$—C$_6$H$_4$) |
| I-29 | H | H | H | —NH-(4-SCH$_3$—C$_6$H$_4$) |
| I-30 | H | H | H | —NH-(2-N(CH$_3$)$_2$-C$_6$H$_4$) |
| I-31 | H | H | H | —NH-(3-N(CH$_3$)$_2$-C$_6$H$_4$) |
| I-32 | H | H | H | —NH-(4-N(CH$_3$)$_2$-C$_6$H$_4$) |
| I-33 | H | H | H | —NH-(4-CN—C$_6$H$_4$) |
| I-34 | H | H | H | —NH-(4-Cl—C$_6$H$_4$) |
| I-35 | H | H | H | —NH-(4-Br—C$_6$H$_4$] |
| I-36 | H | H | H | —NH-(4-F—C$_6$H$_4$] |
| I-37 | H | H | H | —NH-(4-CH$_3$—C$_6$H$_4$) |
| I-38 | H | H | H | —NH-(2-NO$_2$—C$_6$H$_4$) |
| I-39 | H | H | H | —NH-(3-NO$_2$—C$_6$H$_4$) |
| I-40 | H | H | H | —NH-(4-NO$_2$—C$_6$H$_4$] |
| I-41 | H | H | H | —NH-(2,4-OCH$_3$—C$_6$H$_3$) |
| I-42 | H | H | H | —NH-(3,4-OCH$_3$—C$_6$H$_3$) |
| I-43 | H | H | H | —NH-(3,4,5-OCH$_3$—C$_6$H$_2$) |
| I-44 | H | H | H | —NH-(3,4-CH$_2$OCH$_2$—C$_6$H$_3$) |
| I-45 | H | H | H | —NH-(2,3-CH$_2$OCH$_2$—C$_6$H$_3$) |
| I-46 | H | H | H | —NH-2-pyridinyl |
| I-47 | H | H | H | —NH-2-furanyl |
| I-48 | H | H | H | —NH-2-thienyl |
| I-49 | H | H | H | —NH-3-pyridinyl |
| I-50 | H | H | H | —NH-3-furanyl |
| I-51 | H | H | H | —NH-3-thienyl |
| I-52 | H | H | H | —NH-4-pyridinyl |
| I-53 | H | H | H | —NH-2-oxazolyl |
| I-54 | H | H | H | —NH-3-isoxazolyl |
| I-55 | H | H | H | —NH-4-isoxazolyl |
| I-56 | H | H | H | —NH-5-isoxazloyl |
| I-57 | H | H | H | —NH-2R—(but-2-yl) |
| I-58 | H | H | H | —NH-2S—(but-2-yl) |
| I-59 | H | H | H | —NH—O—CH$_3$ |
| I-60 | H | H | H | —N(CH$_3$)(OCH$_3$) |
| I-61 | H | H | H | —N(—(CH$_2$)$_3$—O—) |
| I-62 | H | H | H | —NH—O—CH$_2$—C$_6$H$_5$ |
| I-63 | H | H | H | —N(CH$_3$)(O—CH$_2$—C$_6$H$_5$) |
| I-64 | H | H | H | —N(—(CH$_2$)$_2$—CH(C$_6$H$_5$)—O—) |
| I-65 | H | H | H | —NH—O—C$_2$H$_5$ |
| I-66 | H | H | H | —N(C$_2$H$_5$)(OC$_2$H$_5$) |
| I-67 | H | H | H | —N(CH$_3$)(OC$_2$H$_5$) |
| I-68 | H | H | H | —NH—O-isoC$_3$H$_7$ |
| I-69 | H | H | H | —N(CH$_3$)(O-isoC$_3$H$_7$) |
| I-70 | H | H | H | —NH—O-nC$_3$H$_7$ |
| I-71 | H | H | H | —N(CH$_3$)(O-nC$_3$H$_7$) |
| I-72 | H | H | H | —NH—O-nC$_4$H$_9$ |

TABLE 1-continued

A is Me₂Val, B is Val, D is MeVal, E is Pro, F is of Formula II_F and the group —C(=O)—G is in position 2 relative to the nitrogen atom. G is of Formula II_g or, III_g or IV_g.

| No. | R_F | R¹_F | R²_F | —C(=O)—G |
|---|---|---|---|---|
| I-73 | H | H | H | —N(CH₃)(O-nC₄H₉) |
| I-74 | H | H | H | —NH—O-tertC₄H₉ |
| I-75 | H | H | H | —N(CH₃)(O-tertC₄H₉) |
| I-76 | H | H | H | —NH—O—C₆H₅ |
| I-77 | H | H | H | —N(CH₃)(O—C₆H₅) |
| I-78 | H | H | H | —N(CH₃)₂ |
| I-79 | H | H | H | —N(CH₂—C₆H₅)₂ |
| I-80 | H | H | H | —N(C₂H₅)₂ |
| I-81 | H | H | H | —N(isoC₃H₇)₂ |
| I-82 | H | H | H | —N(nC₃H₇)₂ |
| I-83 | H | H | H | —N(nC₄H₉)₂ |
| I-84 | H | H | H | —N(C₆H₅)₂ |
| I-85 | H | H | H | —NH—CH₂—CH₂—OH |
| I-86 | H | H | H | —NH—(CH₂)₃—OH |
| I-87 | H | H | H | —NH(—(CH₂)₂CH(C₆H₅)OH) |
| I-88 | H | H | H | —NH—(CH₂)₄—OH |
| I-89 | H | H | H | —NH(—CH(CH₃)—CH₂—OH) |
| I-90 | H | H | H | —NH(—CH₂—CH(CH₃)—OH) |
| I-91 | H | H | H | —NH(CH(CH₃)(CH₂)₂OH) |
| I-92 | H | H | H | —NH(—(CH₂)₂CH(CH₃)OH) |
| I-93 | H | 4-CH₃ | H | —NH—CH₃ |
| I-94 | H | 4-CH₃ | H | —NH—CH₂—C₆H₅ |
| I-95 | H | 4-CH₃ | H | —NH-isoC₃H₇ |
| I-96 | H | 4-CH₃ | H | —NH—C₆H₅ |
| I-97 | H | 4-CH₃ | H | —NH—C₂H₅ |
| I-98 | H | 4-CH₃ | H | —NH-nC₃H₇ |
| I-99 | H | 4-CH₃ | H | —NH-nC₄H₉ |
| I-100 | H | 4-CH₃ | H | —NH-tertC₄H₉ |
| I-101 | H | 4-CH₃ | H | —NH-cycloC₃H₅ |
| I-102 | H | 4-CH₃ | H | —NH-cycloC₄H₇ |
| I-103 | H | 4-CH₃ | H | —NH-cycloC₅H₉ |
| I-104 | H | 4-CH₃ | H | —NH-cycloC₆H₁₁ |
| I-105 | H | 4-CH₃ | H | —NH-1-adamantyl |
| I-106 | H | 4-CH₃ | H | —NH-2R—(but-2-yl) |
| I-107 | H | 4-CH₃ | H | —NH-2S—(but-2-yl) |
| I-108 | H | 4-CH₃ | H | —NH—O—CH₃ |
| I-109 | H | 4-CH₃ | H | —N(CH₃)(OCH₃) |
| I-110 | H | 4-CH₃ | H | —N(—(CH₂)₃—O—) |
| I-111 | H | 4-CH₃ | H | —N(CH₃)₂ |
| I-112 | H | 4-CH₃ | H | —N(CH₂—C₆H₅)₂ |
| I-113 | H | 4-CH₃ | H | —N(C₂H₅)₂ |
| I-114 | H | 4-CH₃ | H | —N(isoC₃H₇)₂ |
| I-115 | H | 4-CH₃ | H | —N(nC₃H₇)₂ |
| I-116 | H | 4-CH₃ | H | —N(nC₄H₉)₂ |
| I-117 | H | 4-CH₃ | H | —N(C₆H₅)₂ |
| I-118 | H | 5-CH₃ | H | —NH—CH₃ |
| I-119 | H | 5-CH₃ | H | —NH—CH₂—C₆H₅ |
| I-120 | H | 5-CH₃ | H | —NH-isoC₃H₇ |
| I-121 | H | 5-CH₃ | H | —NH—C₆H₅ |
| I-122 | H | 5-CH₃ | H | —NH—C₂H₅ |
| I-123 | H | 5-CH₃ | H | —NH-nC₃H₇ |
| I-124 | H | 5-CH₃ | H | —NH-nC₄H₉ |
| I-125 | H | 5-CH₃ | H | —NH-tertC₄H₉ |
| I-126 | H | 5-CH₃ | H | —NH-cycloC₃H₅ |
| I-127 | H | 5-CH₃ | H | —NH-cycloC₄H₇ |
| I-128 | H | 5-CH₃ | H | —NH-cycloC₅H₉ |
| I-129 | H | 5-CH₃ | H | —NH-cycloC₆H₁₁ |
| I-130 | H | 5-CH₃ | H | —NH-1-adamantyl |
| I-131 | H | 5-CH₃ | H | —NH-2R—(but-2-yl) |
| I-132 | H | 5-CH₃ | H | —NH-2S—(but-2-yl) |
| I-133 | H | 5-CH₃ | H | —NH—O—CH₃ |
| I-134 | H | 5-CH₃ | H | —N(CH₃)(OCH₃) |
| I-135 | H | 5-CH₃ | H | —N(—(CH₂)₃—O—) |
| I-136 | H | 5-CH₃ | H | —N(CH₃)₂ |
| I-137 | H | 5-CH₃ | H | —N(CH₂—C₆H₅)₂ |
| I-138 | H | 5-CH₃ | H | —N(C₂H₅)₂ |
| I-139 | H | 5-CH₃ | H | —N(isoC₃H₇)₂ |
| I-140 | H | 5-CH₃ | H | —N(nC₃H₇)₂ |
| I-141 | H | 5-CH₃ | H | —N(nC₄H₉)₂ |
| I-142 | H | 5-CH₃ | H | —N(C₆H₅)₂ |
| I-143 | CH₃ | H | H | —NH—CH₃ |
| I-144 | CH₃ | H | H | —NH—CH₂—C₆H₅ |
| I-145 | CH₃ | H | H | —NH-isoC₃H₇ |
| I-146 | CH₃ | H | H | —NH—C₆H₅ |
| I-147 | CH₃ | H | H | —NH—C₂H₅ |
| I-148 | CH₃ | H | H | —NH-nC₃H₇ |
| I-149 | CH₃ | H | H | —NH-nC₄H₉ |
| I-150 | CH₃ | H | H | —NH-tertC₄H₉ |
| I-151 | CH₃ | H | H | —NH-cycloC₃H₅ |
| I-152 | CH₃ | H | H | —NH-cycloC₄H₇ |
| I-153 | CH₃ | H | H | —NH-cycloC₅H₉ |
| I-154 | CH₃ | H | H | —NH-cycloC₆H₁₁ |
| I-155 | CH₃ | H | H | —NH-1-adamantyl |
| I-156 | CH₃ | H | H | —NH-2R—(but-2-yl) |
| I-157 | CH₃ | H | H | —NH-2S—(but-2-yl) |
| I-158 | CH₃ | H | H | —NH—O—CH₃ |
| I-159 | CH₃ | H | H | —N(CH₃)(OCH₃) |
| I-160 | CH₃ | H | H | —N(—(CH₂)₃—O—) |
| I-161 | CH₃ | H | H | —N(CH₃)₂ |
| I-162 | CH₃ | H | H | —N(CH₂—C₆H₅)₂ |
| I-163 | CH₃ | H | H | —N(C₂H₅)₂ |
| I-164 | CH₃ | H | H | —N(isoC₃H₇)₂ |
| I-165 | CH₃ | H | H | —N(nC₃H₇)₂ |
| I-166 | CH₃ | H | H | —N(nC₄H₉)₂ |
| I-167 | CH₃ | H | H | —N(C₆H₅)₂ |
| I-168 | H | 4-OCH₃ | H | —NH—CH₃ |
| I-169 | H | 4-OCH₃ | H | —NH—CH₂—C₆H₅ |
| I-170 | H | 4-OCH₃ | H | —NH-isoC₃H₇ |
| I-171 | H | 4-OCH₃ | H | —NH—C₆H₅ |
| I-172 | H | 4-OCH₃ | H | —NH—C₂H₅ |
| I-173 | H | 4-OCH₃ | H | —NH-nC₃H₇ |
| I-174 | H | 4-OCH₃ | H | —NH-nC₄H₉ |
| I-175 | H | 4-OCH₃ | H | —NH-tertC₄H₉ |
| I-176 | H | 4-OCH₃ | H | —NH-cycloC₃H₅ |
| I-177 | H | 4-OCH₃ | H | —NH-cycloC₄H₇ |
| I-178 | H | 4-OCH₃ | H | —NH-cycloC₅H₉ |
| I-179 | H | 4-OCH₃ | H | —NH-cycloC₆H₁₁ |
| I-180 | H | 4-OCH₃ | H | —NH-1-adamantyl |
| I-181 | H | 4-OCH₃ | H | —NH-2R—(but-2-yl) |
| I-182 | H | 4-OCH₃ | H | —NH-2S—(but-2-yl) |
| I-183 | H | 4-OCH₃ | H | —NH—O—CH₃ |
| I-184 | H | 4-OCH₃ | H | —N(CH₃)(OCH₃) |
| I-185 | H | 4-OCH₃ | H | —N(—(CH₂)₃—O—) |
| I-186 | H | 4-OCH₃ | H | —N(CH₃)₂ |
| I-187 | H | 4-OCH₃ | H | —N(CH₂—C₆H₅)₂ |
| I-188 | H | 4-OCH₃ | H | —N(C₂H₅)₂ |
| I-189 | H | 4-OCH₃ | H | —N(isoC₃H₇)₂ |
| I-190 | H | 4-OCH₃ | H | —N(nC₃H₇)₂ |
| I-191 | H | 4-OCH₃ | H | —N(nC₄H₉)₂ |
| I-192 | H | 4-CH₃ | H | —N(C₆H₅)₂ |
| I-193 | H | 5-OCH₃ | H | —NH—CH₃ |
| I-194 | H | 5-OCH₃ | H | —NH—CH₂—C₆H₅ |
| I-195 | H | 5-OCH₃ | H | —NH-isoC₃H₇ |
| I-196 | H | 5-OCH₃ | H | —NH—C₆H₅ |
| I-197 | H | 5-OCH₃ | H | —NH—C₂H₅ |
| I-198 | H | 5-OCH₃ | H | —NH-nC₃H₇ |
| I-199 | H | 5-OCH₃ | H | —NH-nC₄H₉ |
| I-200 | H | 5-OCH₃ | H | —NH-tertC₄H₉ |
| I-201 | H | 5-OCH₃ | H | —NH-cycloC₃H₅ |
| I-202 | H | 5-OCH₃ | H | —NH-cycloC₄H₇ |
| I-203 | H | 5-OCH₃ | H | —NH-cycloC₅H₉ |
| I-204 | H | 5-OCH₃ | H | —NH-cycloC₆H₁₁ |
| I-205 | H | 5-OCH₃ | H | —NH-1-adamantyl |
| I-206 | H | 5-OCH₃ | H | —NH-2R—(but-2-yl) |
| I-207 | H | 5-OCH₃ | H | —NH-2S—(but-2-yl) |
| I-208 | H | 5-OCH₃ | H | —NH—O—CH₃ |
| I-209 | H | 5-OCH₃ | H | —N(CH₃)(OCH₃) |
| I-210 | H | 5-OCH₃ | H | —N(—(CH₂)₃—O—) |
| I-211 | H | 5-OCH₃ | H | —N(CH₃)₂ |
| I-212 | H | 5-OCH₃ | H | —N(CH₂—C₆H₅)₂ |
| I-213 | H | 5-OCH₃ | H | —N(C₂H₅)₂ |
| I-214 | H | 5-OCH₃ | H | —N(isoC₃H₇)₂ |
| I-215 | H | 5-OCH₃ | H | —N(nC₃H₇)₂ |
| I-216 | H | 5-OCH₃ | H | —N(nC₄H₉)₂ |
| I-217 | H | 5-OCH₃ | H | —N(C₆H₅)₂ |

TABLE 2

A is Me$_2$Val, B is Val, D is MeVal, E is Pro and F is of Formula II$_f$, the group —C(O)—G is in position 3 relative to the nitrogen atom and G is of Formula II$_g$, III$_g$ or IV$_g$.

| No. | R$_F$ | R$^1$F | R$^2$F | —G |
|---|---|---|---|---|
| II-1 | H | H | H | —NH—CH$_3$ |
| II-2 | H | H | H | —NH—CH$_2$—C$_6$H$_5$ |
| II-3 | H | H | H | —NH-isoC$_3$H$_7$ |
| II-4 | H | H | H | —NH—C$_6$H$_5$ |
| II-5 | H | H | H | 1,3-Thiazol-2-yl-amide |
| II-6 | H | 4-OCH$_3$ | 5-OCH$_3$ | —NH—CH$_3$ |
| II-7 | H | 4-cyclo-C$_5$H$_9$ | H | —NH—CH$_3$ |
| II-8 | H | H | H | —NH—C$_2$H$_5$ |
| II-9 | H | H | H | —NH-nC$_3$H$_7$ |
| II-10 | H | H | H | —NH-nC$_4$H$_9$ |
| II-11 | H | H | H | —NH-tertC$_4$H$_9$ |
| II-12 | H | H | H | —NH-cycloC$_3$H$_5$ |
| II-13 | H | H | H | —NH-cycloC$_4$H$_7$ |
| II-14 | H | H | H | —NH-cycloC$_5$H$_9$ |
| II-15 | H | H | H | —NH-cycloC$_6$H$_{11}$ |
| II-16 | H | H | H | —NH-cycloC$_7$H$_{12}$ |
| II-17 | H | H | H | —NH—CH$_2$—O—CH$_3$ |
| II-18 | H | H | H | —NH—CH$_2$—CH$_2$—O—CH$_3$ |
| II-19 | H | H | H | —NH-1-adamantyl |
| II-20 | H | H | H | —NH—(4-HO—C$_6$H$_5$) |
| II-21 | H | H | H | —NH—(2-CF$_3$—C$_6$H$_4$) |
| II-22 | H | H | H | —NH—(3-CF$_3$—C$_6$H$_4$) |
| II-23 | H | H | H | —NH—(4-CF$_3$—C$_6$H$_4$) |
| II-24 | H | H | H | —NH—(2-OCH$_3$—C$_6$H$_4$) |
| II-25 | H | H | H | —NH—(3-OCH$_3$—C$_6$H$_4$) |
| II-26 | H | H | H | —NH—(4-OCH$_3$—C$_6$H$_4$) |
| II-27 | H | H | H | —NH—(2-SCH$_3$—C$_6$H$_4$) |
| II-28 | H | H | H | —NH—(3-SCH$_3$—C$_6$H$_4$) |
| II-29 | H | H | H | —NH—(4-SCH$_3$—C$_6$H$_4$) |
| II-30 | H | H | H | —NH—(2-N(CH$_3$)$_2$—C$_6$H$_4$) |
| II-31 | H | H | H | —NH—(3-N(CH$_3$)$_2$—C$_6$H$_4$) |
| II-32 | H | H | H | —NH—(4-N(CH$_3$)$_2$—C$_6$H$_4$) |
| II-33 | H | H | H | —NH—(4-CN—C$_6$H$_4$) |
| II-34 | H | H | H | —NH—(4-Cl—C$_6$H$_4$) |
| II-35 | H | H | H | —NH—(4-Br—C$_6$H$_4$] |
| II-36 | H | H | H | —NH—(4-F—C$_6$H$_4$] |
| II-37 | H | H | H | —NH—(4-CH$_3$—C$_6$H$_4$) |
| II-38 | H | H | H | —NH—(2-NO$_2$—C$_6$H$_4$) |
| II-39 | H | H | H | —NH—(3-NO$_2$—C$_6$H$_4$) |
| II-40 | H | H | H | —NH—(4-NO$_2$—C$_6$H$_4$] |
| II-41 | H | H | H | —NH—(2,4-OCH$_3$—C$_6$H$_3$) |
| II-42 | H | H | H | —NH—(3,4-OCH$_3$—C$_6$H$_3$) |
| II-43 | H | H | H | —NH—(3,4,5-OCH$_3$—C$_6$H$_2$) |
| II-44 | H | H | H | —NH—(3,4-CH$_2$OCH$_2$—C$_6$H$_3$) |
| II-45 | H | H | H | —NH—(2,3-CH$_2$OCH$_2$—C$_6$H$_3$) |
| II-46 | H | H | H | —NH-2-pyridinyl |
| II-47 | H | H | H | —NH-2-furanyl |
| II-48 | H | H | H | —NH-2-thienyl |
| II-49 | H | H | H | —NH-3-pyridinyl |
| II-50 | H | H | H | —NH-3-furanyl |
| II-51 | H | H | H | —NH-3-thienyl |
| II-52 | H | H | H | —NH-4-pyridinyl |
| II-53 | H | H | H | —NH-2-oxazolyl |
| II-54 | H | H | H | —NH-3-isoxazolyl |
| II-55 | H | H | H | —NH-4-isoxazolyl |
| II-56 | H | H | H | —NH-5-isoxazoyl |
| II-57 | H | H | H | —NH-2R—(but-2-yl) |
| II-58 | H | H | H | —NH-2S—(but-2-yl) |
| II-59 | H | H | H | —NH—O—CH$_3$ |
| II-60 | H | H | H | —N(CH$_3$)(OCH$_3$) |
| II-61 | H | H | H | —N(—(CH$_2$)$_3$—O—) |
| II-62 | H | H | H | —NH—O—CH$_2$—C$_6$H$_5$ |
| II-63 | H | H | H | —N(CH$_3$)(O—CH$_2$—C$_6$H$_5$) |
| II-64 | H | H | H | —N(—(CH$_2$)$_2$—CH(C$_6$H$_5$)—O—) |
| II-65 | H | H | H | —NH—O—C$_2$H$_5$ |
| II-66 | H | H | H | —N(C$_2$H$_5$)(OC$_2$H$_5$) |
| II-67 | H | H | H | —N(CH$_3$)(OC$_2$H$_5$) |
| II-68 | H | H | H | —NH—O-isoC$_3$H$_7$ |
| II-69 | H | H | H | —N(CH$_3$)(O-isoC$_3$H$_7$) |
| II-70 | H | H | H | —NH—O-nC$_3$H$_7$ |
| II-71 | H | H | H | —N(CH$_3$)(O-nC$_3$H$_7$) |
| II-72 | H | H | H | —NH—O-nC$_4$H$_9$ |
| II-73 | H | H | H | —N(CH$_3$)(O-nC$_4$H$_9$) |

TABLE 2-continued

A is Me$_2$Val, B is Val, D is MeVal, E is Pro and F is of Formula II$_f$, the group —C(O)—G is in position 3 relative to the nitrogen atom and G is of Formula II$_g$, III$_g$ or IV$_g$.

| No. | R$_F$ | R$^1$F | R$^2$F | —G |
|---|---|---|---|---|
| II-74 | H | H | H | —NH—O-tertC$_4$H$_9$ |
| II-75 | H | H | H | —N(CH$_3$)(O-tertC$_4$H$_9$) |
| II-76 | H | H | H | —NH—O—C$_6$H$_5$ |
| II-77 | H | H | H | —N(CH$_3$)(O—C$_6$H$_5$) |
| II-78 | H | H | H | —N(CH$_3$)$_2$ |
| II-79 | H | H | H | —N(CH$_2$—C$_6$H$_5$)$_2$ |
| II-80 | H | H | H | —N(C$_2$H$_5$)$_2$ |
| II-81 | H | H | H | —N(isoC$_3$H$_7$)$_2$ |
| II-82 | H | H | H | —N(nC$_3$H$_7$)$_2$ |
| II-83 | H | H | H | —N(nC$_4$H$_9$)$_2$ |
| II-84 | H | H | H | —N(C$_6$H$_5$)$_2$ |
| II-85 | H | H | H | —NH—CH$_2$—CH$_2$—OH |
| II-86 | H | H | H | —NH—(CH$_2$)$_3$—OH |
| II-87 | H | H | H | —NH(—(CH$_2$)$_2$—CH(C$_6$H$_5$)—OH) |
| II-88 | H | H | H | —NH—(CH$_2$)$_4$—OH |
| II-89 | H | H | H | —NH(—CH(CH$_3$)—CH$_2$—OH) |
| II-90 | H | H | H | —NH(—CH$_2$—CH(CH$_3$)—OH) |
| II-91 | H | H | H | —NH(—CH(CH$_3$)—(CH$_2$)$_2$—OH) |
| II-92 | H | H | H | —NH(—(CH$_2$)$_2$—CH(CH$_3$)—OH) |
| II-93 | H | 4-CH$_3$ | H | —NH—CH$_3$ |
| II-94 | H | 4-CH$_3$ | H | —NH—CH$_2$—C$_6$H$_5$ |
| II-95 | H | 4-CH$_3$ | H | —NH-isoC$_3$H$_7$ |
| II-96 | H | 4-CH$_3$ | H | —NH—C$_6$H$_5$ |
| II-97 | H | 4-CH$_3$ | H | —NH—C$_2$H$_5$ |
| II-98 | H | 4-CH$_3$ | H | —NH-nC$_3$H$_7$ |
| II-99 | H | 4-CH$_3$ | H | —NH-nC$_4$H$_9$ |
| II-100 | H | 4-CH$_3$ | H | —NH-tertC$_4$H$_9$ |
| II-101 | H | 4-CH$_3$ | H | —NH-cycloC$_3$H$_5$ |
| II-102 | H | 4-CH$_3$ | H | —NH-cycloC$_4$H$_7$ |
| II-103 | H | 4-CH$_3$ | H | —NH-cycloC$_5$H$_9$ |
| II-104 | H | 4-CH$_3$ | H | —NH-cycloC$_6$H$_{11}$ |
| II-105 | H | 4-CH$_3$ | H | —NH-1-adamantyl |
| II-106 | H | 4-CH$_3$ | H | —NH-2R—(but-2-yl) |
| II-107 | H | 4-CH$_3$ | H | —NH-2S—(but-2-yl) |
| II-108 | H | 4-CH$_3$ | H | —NH—O—CH$_3$ |
| II-109 | H | 4-CH$_3$ | H | —N(CH$_3$)(OCH$_3$) |
| II-110 | H | 4-CH$_3$ | H | —N(—(CH$_2$)$_3$—O—) |
| II-111 | H | 4-CH$_3$ | H | —N(CH$_3$)$_2$ |
| II-112 | H | 4-CH$_3$ | H | —N(CH$_2$—C$_6$H$_5$)$_2$ |
| II-113 | H | 4-CH$_3$ | H | —N(C$_2$H$_5$)$_2$ |
| II-114 | H | 4-CH$_3$ | H | —N(isoC$_3$H$_7$)$_2$ |
| II-115 | H | 4-CH$_3$ | H | —N(nC$_3$H$_7$)$_2$ |
| II-116 | H | 4-CH$_3$ | H | —N(nC$_4$H$_9$)$_2$ |
| II-117 | H | 4-CH$_3$ | H | —N(C$_6$H$_5$)$_2$ |
| II-118 | H | 5-CH$_3$ | H | —NH—CH$_3$ |
| II-119 | H | 5-CH$_3$ | H | —NH—CH$_2$—C$_6$H$_5$ |
| II-120 | H | 5-CH$_3$ | H | —NH-isoC$_3$H$_7$ |
| II-121 | H | 5-CH$_3$ | H | —NH—C$_6$H$_5$ |
| II-122 | H | 5-CH$_3$ | H | —NH—C$_2$H$_5$ |
| II-123 | H | 5-CH$_3$ | H | —NH-nC$_3$H$_7$ |
| II-124 | H | 5-CH$_3$ | H | —NH-nC$_4$H$_9$ |
| II-125 | H | 5-CH$_3$ | H | —NH-tertC$_4$H$_9$ |
| II-126 | H | 5-CH$_3$ | H | —NH-cycloC$_3$H$_5$ |
| II-127 | H | 5-CH$_3$ | H | —NH-cycloC$_4$H$_7$ |
| II-128 | H | 5-CH$_3$ | H | —NH-cycloC$_5$H$_9$ |
| II-129 | H | 5-CH$_3$ | H | —NH-cycloC$_6$H$_{11}$ |
| II-130 | H | 5-CH$_3$ | H | —NH-1-adamantyl |
| II-131 | H | 5-CH$_3$ | H | —NH-2R—(but-2-yl) |
| II-132 | H | 5-CH$_3$ | H | —NH-2S—(but-2-yl) |
| II-133 | H | 5-CH$_3$ | H | —NH—O—CH$_3$ |
| II-134 | H | 5-CH$_3$ | H | —N(CH$_3$)(OCH$_3$) |
| II-135 | H | 5-CH$_3$ | H | —N(—(CH$_2$)$_3$—O—) |
| II-136 | H | 5-CH$_3$ | H | —N(CH$_3$)$_2$ |
| II-137 | H | 5-CH$_3$ | H | —N(CH$_2$—C$_6$H$_5$)$_2$ |
| II-138 | H | 5-CH$_3$ | H | —N(C$_2$H$_5$)$_2$ |
| II-139 | H | 5-CH$_3$ | H | —N(isoC$_3$H$_7$)$_2$ |
| II-140 | H | 5-CH$_3$ | H | —N(nC$_3$H$_7$)$_2$ |
| II-141 | H | 5-CH$_3$ | H | —N(nC$_4$H$_9$)$_2$ |
| II-142 | H | 5-CH$_3$ | H | —N(C$_6$H$_5$)$_2$ |
| II-143 | CH$_3$ | H | H | —NH—CH$_3$ |
| II-144 | CH$_3$ | H | H | —NH—CH$_2$—C$_6$H$_5$ |
| II-145 | CH$_3$ | H | H | —NH-isoC$_3$H$_7$ |
| II-146 | CH$_3$ | H | H | —NH—C$_6$H$_5$ |

TABLE 2-continued

A is Me₂Val, B is Val, D is MeVal, E is Pro and F is of Formula II_f, the group —C(O)—G is in position 3 relative to the nitrogen atom and G is of Formula II_g, III_g or IV_g.

| No. | $R_F$ | $R^1F$ | $R^2F$ | —G |
|---|---|---|---|---|
| II-147 | $CH_3$ | H | H | —NH—$C_2H_5$ |
| II-148 | $CH_3$ | H | H | —NH-$nC_3H_7$ |
| II-149 | $CH_3$ | H | H | —NH-$nC_4H_9$ |
| II-150 | $CH_3$ | H | H | —NH-tert$C_4H_9$ |
| II-151 | $CH_3$ | H | H | —NH-cyclo$C_3H_5$ |
| II-152 | $CH_3$ | H | H | —NH-cyclo$C_4H_7$ |
| II-153 | $CH_3$ | H | H | —NH-cyclo$C_5H_9$ |
| II-154 | $CH_3$ | H | H | —NH-cyclo$C_6H_{11}$ |
| II-155 | $CH_3$ | H | H | —NH-1-adamantyl |
| II-156 | $CH_3$ | H | H | —NH-2R—(but-2-yl) |
| II-157 | $CH_3$ | H | H | —NH-2S—(but-2-yl) |
| II-158 | $CH_3$ | H | H | —NH—O—$CH_3$ |
| II-159 | $CH_3$ | H | H | —N($CH_3$)(O$CH_3$) |
| II-160 | $CH_3$ | H | H | —N(—($CH_2$)$_3$—O—) |
| II-161 | $CH_3$ | H | H | —N($CH_3$)$_2$ |
| II-162 | $CH_3$ | H | H | —N($CH_2$—$C_6H_5$)$_2$ |
| II-163 | $CH_3$ | H | H | —N($C_2H_5$)$_2$ |
| II-164 | $CH_3$ | H | H | —N(iso$C_3H_7$)$_2$ |
| II-165 | $CH_3$ | H | H | —N($nC_3H_7$)$_2$ |
| II-166 | $CH_3$ | H | H | —N($nC_4H_9$)$_2$ |
| II-167 | $CH_3$ | H | H | —N($C_6H_5$)$_2$ |
| II-168 | H | 4-O$CH_3$ | H | —NH—$CH_3$ |
| II-169 | H | 4-O$CH_3$ | H | —NH—$CH_2$—$C_6H_5$ |
| II-170 | H | 4-O$CH_3$ | H | —NH-iso$C_3H_7$ |
| II-171 | H | 4-O$CH_3$ | H | —NH—$C_6H_5$ |
| II-172 | H | 4-O$CH_3$ | H | —NH—$C_2H_5$ |
| II-173 | H | 4-O$CH_3$ | H | —NH-$nC_3H_7$ |
| II-174 | H | 4-O$CH_3$ | H | —NH-$nC_4H_9$ |
| II-175 | H | 4-O$CH_3$ | H | —NH-tert$C_4H_9$ |
| II-176 | H | 4-O$CH_3$ | H | —NH-cyclo$C_3H_5$ |
| II-177 | H | 4-O$CH_3$ | H | —NH-cyclo$C_4H_7$ |
| II-178 | H | 4-O$CH_3$ | H | —NH-cyclo$C_5H_9$ |
| II-179 | H | 4-O$CH_3$ | H | —NH-cyclo$C_6H_{11}$ |
| II-180 | H | 4-O$CH_3$ | H | —NH-1-adamantyl |
| II-181 | H | 4-O$CH_3$ | H | —NH-2R—(but-2-yl) |
| II-182 | H | 4-O$CH_3$ | H | —NH-2S—(but-2-yl) |
| II-183 | H | 4-O$CH_3$ | H | —NH—O—$CH_3$ |
| II-184 | H | 4-O$CH_3$ | H | —N($CH_3$)(O$CH_3$) |
| II-185 | H | 4-O$CH_3$ | H | —N(—($CH_2$)$_3$—O—) |
| II-186 | H | 4-O$CH_3$ | H | —N($CH_3$)$_2$ |
| II-187 | H | 4-O$CH_3$ | H | —N($CH_2$—$C_6H_5$)$_2$ |
| II-188 | H | 4-O$CH_3$ | H | —N($C_2H_5$)$_2$ |
| II-189 | H | 4-O$CH_3$ | H | —N(iso$C_3H_7$)$_2$ |
| II-190 | H | 4-O$CH_3$ | H | —N($nC_3H_7$)$_2$ |
| II-191 | H | 4-O$CH_3$ | H | —N($nC_4H_9$)$_2$ |
| II-192 | H | 4-O$CH_3$ | H | —N($C_6H_5$)$_2$ |
| II-193 | H | 5-O$CH_3$ | H | —NH—$CH_3$ |
| II-194 | H | 5-O$CH_3$ | H | —NH—$CH_2$—$C_6H_5$ |
| II-195 | H | 5-O$CH_3$ | H | —NH-iso$C_3H_7$ |
| II-196 | H | 5-O$CH_3$ | H | —NH—$C_6H_5$ |
| II-197 | H | 5-O$CH_3$ | H | —NH—$C_2H_5$ |
| II-198 | H | 5-O$CH_3$ | H | —NH-$nC_3H_7$ |
| II-199 | H | 5-O$CH_3$ | H | —NH-$nC_4H_9$ |
| II-200 | H | 5-O$CH_3$ | H | —NH-tert$C_4H_9$ |
| II-201 | H | 5-O$CH_3$ | H | —NH-cyclo$C_3H_5$ |
| II-202 | H | 5-O$CH_3$ | H | —NH-cyclo$C_4H_7$ |
| II-203 | H | 5-O$CH_3$ | H | —NH-cyclo$C_5H_9$ |
| II-204 | H | 5-O$CH_3$ | H | —NH-cyclo$C_6H_{11}$ |
| II-205 | H | 5-O$CH_3$ | H | —NH-1-adamantyl |
| II-206 | H | 5-O$CH_3$ | H | —NH-2R—(but-2-yl) |
| II-207 | H | 5-O$CH_3$ | H | —NH-2S—(but-2-yl) |
| II-208 | H | 5-O$CH_3$ | H | —NH—O—$CH_3$ |
| II-209 | H | 5-O$CH_3$ | H | —N($CH_3$)(O$CH_3$) |
| II-210 | H | 5-O$CH_3$ | H | —N(—($CH_2$)$_3$—O—) |
| II-211 | H | 5-O$CH_3$ | H | —N($CH_3$)$_2$ |
| II-212 | H | 5-O$CH_3$ | H | —N($CH_2$—$C_6H_5$)$_2$ |
| II-213 | H | 5-O$CH_3$ | H | —N($C_2H_5$)$_2$ |
| II-214 | H | 5-O$CH_3$ | H | —N(iso$C_3H_7$)$_2$ |
| II-215 | H | 5-O$CH_3$ | H | —N($nC_3H_7$)$_2$ |
| II-216 | H | 5-O$CH_3$ | H | —N($nC_4H_9$)$_2$ |
| II-217 | H | 5-O$CH_3$ | H | —N($C_6H_5$)$_2$ |

TABLE 3

A is Me₂Val, B is Val, D is MeVal, E is Pro, F is of Formula II_f, the substituent —(C=O)—G is in position 4 relative to the nitrogen. G is of Formula II_g, III_g or IV_g.

| No. | $R_F$ | $R^1F$ | $R^2F$ | —G |
|---|---|---|---|---|
| III-1 | H | H | H | —NH—CH₃ |
| III-2 | H | H | H | —NH—CH₂—C₆H₅ |
| III-3 | H | H | H | —NH-isoC₃H₇ |
| III-4 | H | H | H | —NH—C₆H₅ |
| III-5 | H | H | H | 1,3-Thiazol-2-yl-amide |
| III-6 | H | 3-OCH₃ | 5-OCH₃ | —NH—CH₃ |
| III-7 | H | 3-cyclo-C₅H₉ | H | —NH—CH₃ |
| III-8 | H | H | H | —NH—C₂H₅ |
| III-9 | H | H | H | —NH-nC₃H₇ |
| III-10 | H | H | H | —NH-nC₄H₉ |
| III-11 | H | H | H | —NH-tertC₄H₉ |
| III-12 | H | H | H | —NH-cycloC₃H₅ |
| III-13 | H | H | H | —NH-cycloC₄H₇ |
| III-14 | H | H | H | —NH-cycloC₅H₉ |
| III-15 | H | H | H | —NH-cycloC₆H₁₁ |
| III-16 | H | H | H | —NH-cycloC₇H₁₂ |
| III-17 | H | H | H | —NH—CH₂—O—CH₃ |
| III-18 | H | H | H | —NH—CH₂—CH₂—O—CH₃ |
| III-19 | H | H | H | —NH-1-adamantyl |
| III-20 | H | H | H | —NH—(4-HO—C₆H₅) |
| III-21 | H | H | H | —NH—(2-CF₃—C₆H₄) |
| III-22 | H | H | H | —NH—(3-CF₃—C₆H₄) |
| III-23 | H | H | H | —NH—(4-CF₃—C₆H₄) |
| III-24 | H | H | H | —NH—(2-OCH₃—C₆H₄) |
| III-25 | H | H | H | —NH—(3-OCH₃—C₆H₄) |
| III-26 | H | H | H | —NH—(4-OCH₃—C₆H₄) |
| III-27 | H | H | H | —NH—(2-SCH₃—C₆H₄) |
| III-28 | H | H | H | —NH—(3-SCH₃—C₆H₄) |
| III-29 | H | H | H | —NH—(4-SCH₃—C₆H₄) |
| III-30 | H | H | H | —NH—(2-N(CH₃)₂—C₆H₄) |
| III-31 | H | H | H | —NH—(3-N(CH₃)₂—C₆H₄) |
| III-32 | H | H | H | —NH—(4-N(CH₃)₂—C₆H₄) |
| III-33 | H | H | H | —NH—(4-CN—C₆H₄) |
| III-34 | H | H | H | —NH—(4-Cl—C₆H₄) |
| III-35 | H | H | H | —NH—(4-Br—C₆H₄] |
| III-36 | H | H | H | —NH—(4-F—C₆H₄] |
| III-37 | H | H | H | —NH—(4-CH₃—C₆H₄) |
| III-38 | H | H | H | —NH—(2-NO₂—C₆H₄) |
| III-39 | H | H | H | —NH—(3-NO₂—C₆H₄) |
| III-40 | H | H | H | —NH—(4-NO₂—C₆H₄] |
| III-41 | H | H | H | —NH—(2,4-OCH₃—C₆H₃) |
| III-42 | H | H | H | —NH—(3,4-OCH₃—C₆H₃) |
| III-43 | H | H | H | —NH—(3,4,5-OCH₃—C₆H₂) |
| III-44 | H | H | H | —NH—(3,4-CH₂OCH₂—C₆H₃) |
| III-45 | H | H | H | —NH—(2,3-CH₂OCH₂—C₆H₃) |
| III-46 | H | H | H | —NH-2-pyridinyl |
| III-47 | H | H | H | —NH-2-furanyl |
| III-48 | H | H | H | —NH-2-thienyl |
| III-49 | H | H | H | —NH-3-pyridinyl |
| III-50 | H | H | H | —NH-3-furanyl |
| III-51 | H | H | H | —NH-3-thienyl |
| III-52 | H | H | H | —NH-4-pyridinyl |
| III-53 | H | H | H | —NH-2-oxazolyl |
| III-54 | H | H | H | —NH-3-isoxazolyl |
| III-55 | H | H | H | —NH-4-isoxazolyl |
| III-56 | H | H | H | —NH-5-isoxazolyl |
| III-57 | H | H | H | —NH-2R—(but-2-yl) |
| III-58 | H | H | H | —NH-2S—(but-2-yl) |
| III-59 | H | H | H | —NH—O—CH₃ |
| III-60 | H | H | H | —N(CH₃)(OCH₃) |
| III-61 | H | H | H | —N(—(CH₂)₃—O—) |
| III-62 | H | H | H | —NH—O—CH₂—C₆H₅ |
| III-63 | H | H | H | —N(CH₃)(O—CH₂—C₆H₅) |
| III-64 | H | H | H | —N(—(CH₂)₂—CH(C₆H₅)—O—) |
| III-65 | H | H | H | —NH—O—C₂H₅ |
| III-66 | H | H | H | —N(C₂H₅)(OC₂H₅) |
| III-67 | H | H | H | —N(CH₃)(OC₂H₅) |
| III-68 | H | H | H | —NH—O-isoC₃H₇ |
| III-69 | H | H | H | —N(CH₃)(O-isoC₃H₇) |
| III-70 | H | H | H | —NH—O-nC₃H₇ |
| III-71 | H | H | H | —N(CH₃)(O-nC₃H₇) |
| III-72 | H | H | H | —NH—O-nC₄H₉ |
| III-73 | H | H | H | —N(CH₃)(O-nC₄H₉) |

TABLE 3-continued

A is Me$_2$Val, B is Val, D is MeVal, E is Pro, F is of
Formula II$_F$, the substituent —(C=O)—G is in position 4
relative to the nitrogen. G is of Formula II$_g$, III$_g$ or IV$_g$.

| No. | R$_F$ | R$^1$F | R$^2$F | —G |
|---|---|---|---|---|
| III-74 | H | H | H | —NH—O-tertC$_4$H$_9$ |
| III-75 | H | H | H | —N(CH$_3$)(O-tertC$_4$H$_9$) |
| III-76 | H | H | H | —NH—O—C$_6$H$_5$ |
| III-77 | H | H | H | —N(CH$_3$)(O—C$_6$H$_5$) |
| III-78 | H | H | H | —N(CH$_3$)$_2$ |
| III-79 | H | H | H | —N(CH$_2$—C$_6$H$_5$)$_2$ |
| III-80 | H | H | H | —N(C$_2$H$_5$)$_2$ |
| III-81 | H | H | H | —N(isoC$_3$H$_7$)$_2$ |
| III-82 | H | H | H | —N(nC$_3$H$_7$)$_2$ |
| III-83 | H | H | H | —N(nC$_4$H$_9$)$_2$ |
| III-84 | H | H | H | —N(C$_6$H$_5$)$_2$ |
| III-85 | H | H | H | —NH—CH$_2$—CH$_2$—OH |
| III-86 | H | H | H | —NH—(CH$_2$)$_3$—OH |
| III-87 | H | H | H | —NH(—(CH$_2$)$_2$—CH(C$_6$H$_5$)—OH) |
| III-88 | H | H | H | —NH—(CH$_2$)$_4$—OH |
| III-89 | H | H | H | —NH(—CH(CH$_3$)—CH$_2$—OH) |
| III-90 | H | H | H | —NH(—CH$_2$—CH(CH$_3$)—OH) |
| III-91 | H | H | H | —NH(—CH(CH$_3$)—(CH$_2$)$_2$—OH) |
| III-92 | H | H | H | —NH(—(CH$_2$)$_2$—CH(CH$_3$)—OH) |
| III-93 | H | 2-CH$_3$ | H | —NH—CH$_3$ |
| III-94 | H | 2-CH$_3$ | H | —NH—CH$_2$—C$_6$H$_5$ |
| III-95 | H | 2-CH$_3$ | H | —NH-isoC$_3$H$_7$ |
| III-96 | H | 2-CH$_3$ | H | —NH—C$_6$H$_5$ |
| III-97 | H | 2-CH$_3$ | H | —NH—C$_2$H$_5$ |
| III-98 | H | 2-CH$_3$ | H | —NH-nC$_3$H$_7$ |
| III-99 | H | 2-CH$_3$ | H | —NH-nC$_4$H$_9$ |
| III-100 | H | 2-CH$_3$ | H | —NH-tertC$_4$H$_9$ |
| III-101 | H | 2-CH$_3$ | H | —NH-cycloC$_3$H$_5$ |
| III-102 | H | 2-CH$_3$ | H | —NH-cycloC$_4$H$_7$ |
| III-103 | H | 2-CH$_3$ | H | —NH-cycloC$_5$H$_9$ |
| III-104 | H | 2-CH$_3$ | H | —NH-cycloC$_6$H$_{11}$ |
| III-105 | H | 2-CH$_3$ | H | —NH-1-adamantyl |
| III-106 | H | 2-CH$_3$ | H | —NH-2R—(but-2-yl) |
| III-107 | H | 2-CH$_3$ | H | —NH-2S—(but-2-yl) |
| III-108 | H | 2-CH$_3$ | H | —NH—O—CH$_3$ |
| III-109 | H | 2-CH$_2$ | H | —N(CH$_3$)(OCH$_3$) |
| III-110 | H | 2-CH$_3$ | H | —N(—(CH$_2$)$_3$—O—) |
| III-111 | H | 2-CH$_3$ | H | —N(CH$_3$)$_2$ |
| III-112 | H | 2-CH$_3$ | H | —N(CH$_2$—C$_6$H$_5$)$_2$ |
| III-113 | H | 2-CH$_3$ | H | —N(C$_2$H$_5$)$_2$ |
| III-114 | H | 2-CH$_3$ | H | —N(isoC$_3$H$_7$)$_2$ |
| III-115 | H | 2-CH$_3$ | H | —N(nC$_3$H$_7$)$_2$ |
| III-116 | H | 2-CH$_3$ | H | —N(nC$_4$H$_9$)$_2$ |
| III-117 | H | 2-CH$_3$ | H | —N(C$_6$H$_5$)$_2$ |
| III-118 | H | 3-CH$_3$ | H | —NH—CH$_3$ |
| III-119 | H | 3-CH$_3$ | H | —NH—CH$_2$—C$_6$H$_5$ |
| III-120 | H | 3-CH$_3$ | H | —NH-isoC$_3$H$_7$ |
| III-121 | H | 3-CH$_3$ | H | —NH—C$_6$H$_5$ |
| III-122 | H | 3-CH$_3$ | H | —NH—C$_2$H$_5$ |
| III-123 | H | 3-CH$_3$ | H | —NH-nC$_3$H$_7$ |
| III-124 | H | 3-CH$_3$ | H | —NH-nC$_4$H$_9$ |
| III-125 | H | 3-CH$_3$ | H | —NH-tertC$_4$H$_9$ |
| III-126 | H | 3-CH$_3$ | H | —NH-cycloC$_3$H$_5$ |
| III-127 | H | 3-CH$_3$ | H | —NH-cycloC$_4$H$_7$ |
| III-128 | H | 3-CH$_3$ | H | —NH-cycloC$_5$H$_9$ |
| III-129 | H | 3-CH$_3$ | H | —NH-cycloC$_6$H$_{11}$ |
| III-130 | H | 3-CH$_3$ | H | —NH-1-adamantyl |
| III-131 | H | 3-CH$_3$ | H | —NH-2R—(but-2-yl) |
| III-132 | H | 3-CH$_3$ | H | —NH-2S—(but-2-yl) |
| III-133 | H | 3-CH$_3$ | H | —NH—O—CH$_3$ |
| III-134 | H | 3-CH$_3$ | H | —N(CH$_3$)(OCH$_3$) |
| III-135 | H | 3-CH$_3$ | H | —N(—(CH$_2$)$_3$—O—) |
| III-136 | H | 3-CH$_3$ | H | —N(CH$_3$)$_2$ |
| III-137 | H | 3-CH$_3$ | H | —N(CH$_2$—C$_6$H$_5$)$_2$ |
| III-138 | H | 3-CH$_3$ | H | —N(C$_2$H$_5$)$_2$ |
| III-139 | H | 3-CH$_3$ | H | —N(isoC$_3$H$_7$)$_2$ |
| III-140 | H | 3-CH$_3$ | H | —N(nC$_3$H$_7$)$_2$ |
| III-141 | H | 3-CH$_3$ | H | —N(nC$_4$H$_9$)$_2$ |
| III-142 | H | 3-CH$_3$ | H | —N(C$_6$H$_5$)$_2$ |
| III-143 | CH$_3$ | H | H | —NH—CH$_3$ |
| III-144 | CH$_3$ | H | H | —NH—CH$_2$—C$_6$H$_5$ |
| III-145 | CH$_3$ | H | H | —NH-isoC$_3$H$_7$ |
| III-146 | CH$_3$ | H | H | —NH—C$_6$H$_5$ |

TABLE 3-continued

A is Me₂Val, B is Val, D is MeVal, E is Pro, F is of
Formula II_F, the substituent —(C═O)—G is in position 4
relative to the nitrogen. G is of Formula II_g, III_g or IV_g.

| No. | R_F | R¹F | R²F | —G |
|---|---|---|---|---|
| III-147 | CH₃ | H | H | —NH—C₂H₅ |
| III-148 | CH₃ | H | H | —NH-nC₃H₇ |
| III-149 | CH₃ | H | H | —NH-nC₄H₉ |
| III-150 | CH₃ | H | H | —NH-tertC₄H₉ |
| III-151 | CH₃ | H | H | —NH-cycloC₃H₅ |
| III-152 | CH₃ | H | H | —NH-cycloC₄H₇ |
| III-153 | CH₃ | H | H | —NH-cycloC₅H₉ |
| III-154 | CH₃ | H | H | —NH-cycloC₆H₁₁ |
| III-155 | CH₃ | H | H | —NH-1-adamantyl |
| III-156 | CH₃ | H | H | —NH-2R—(but-2-yl) |
| III-157 | CH₃ | H | H | —NH-2S—(but-2-yl) |
| III-158 | CH₃ | H | H | —NH—O—CH₃ |
| III-159 | CH₃ | H | H | —N(CH₃)(OCH₃) |
| III-160 | CH₃ | H | H | —N(—(CH₂)₃—O—) |
| III-161 | CH₃ | H | H | —N(CH₃)₂ |
| III-162 | CH₃ | H | H | —N(CH₂—C₆H₅)₂ |
| III-163 | CH₃ | H | H | —N(C₂H₅)₂ |
| III-164 | CH₃ | H | H | —N(isoC₃H₇)₂ |
| III-165 | CH₃ | H | H | —N(nC₃H₇)₂ |
| III-166 | CH₃ | H | H | —N(nC₄H₉)₂ |
| III-167 | CH₃ | H | H | —N(C₆H₅)₂ |
| III-168 | H | 2-OCH₃ | H | —NH—CH₃ |
| III-169 | H | 2-OCH₃ | H | —NH—CH₂—C₆H₅ |
| III-170 | H | 2-OCH₃ | H | —NH-isoC₃H₇ |
| III-171 | H | 2-OCH₃ | H | —NH—C₆H₅ |
| III-172 | H | 2-OCH₃ | H | —NH—C₂H₅ |
| III-173 | H | 2-OCH₃ | H | —NH-nC₃H₇ |
| III-174 | H | 2-OCH₃ | H | —NH-nC₄H₉ |
| III-175 | H | 2-OCH₃ | H | —NH-tertC₄H₉ |
| III-176 | H | 2-OCH₃ | H | —NH-cycloC₃H₅ |
| III-177 | H | 2-OCH₃ | H | —NH-cycloC₄H₇ |
| III-178 | H | 2-OCH₃ | H | —NH-cycloC₅H₉ |
| III-179 | H | 2-OCH₃ | H | —NH-cycloC₆H₁₁ |
| III-180 | H | 2-OCH₃ | H | —NH-1-adamantyl |
| III-181 | H | 2-OCH₃ | H | —NH-2R—(but-2-yl) |
| III-182 | H | 2-OCH₃ | H | —NH-2S—(but-2-yl) |
| III-183 | H | 2-OCH₃ | H | —NH—O—CH₃ |
| III-184 | H | 2-OCH₃ | H | —N(CH₃)(OCH₃) |
| III-185 | H | 2-OCH₃ | H | —N(—(CH₂)₃—O—) |
| III-186 | H | 2-OCH₃ | H | —N(CH₃)₂ |
| III-187 | H | 2-OCH₃ | H | —N(CH₂—C₆H₅)₂ |
| III-188 | H | 2-OCH₃ | H | —N(C₂H₅)₂ |
| III-189 | H | 2-OCH₃ | H | —N(isoC₃H₇)₂ |
| III-190 | H | 2-OCH₃ | H | —N(nC₃H₇)₂ |
| III-191 | H | 2-OCH₃ | H | —N(nC₄H₉)₂ |
| III-192 | H | 2-OCH₃ | H | —N(C₆H₅)₂ |
| III-193 | H | 3-OCH₃ | H | —NH—CH₃ |
| III-194 | H | 3-OCH₃ | H | —NH—CH₂—C₆H₅ |
| III-195 | H | 3-OCH₃ | H | —NH-isoC₃H₇ |
| III-196 | H | 3-OCH₃ | H | —NH—C₆H₅ |
| III-197 | H | 3-OCH₃ | H | —NH—C₂H₅ |
| III-198 | H | 3-OCH₃ | H | —NH-nC₃H₇ |
| III-199 | H | 3-OCH₃ | H | —NH-nC₄H₉ |
| III-200 | H | 3-OCH₃ | H | —NH-tertC₄H₉ |
| III-201 | H | 3-OCH₃ | H | —NH-cycloC₃H₅ |
| III-202 | H | 3-OCH₃ | H | —NH-cycloC₄H₇ |
| III-203 | H | 3-OCH₃ | H | —NH-cycloC₅H₉ |
| III-204 | H | 3-OCH₃ | H | —NH-cycloC₆H₁₁ |
| III-205 | H | 3-OCH₃ | H | —NH-1-adamantyl |
| III-206 | H | 3-OCH₃ | H | —NH-2R—(but-2-yl) |
| III-207 | H | 3-OCH₃ | H | —NH-2S—(but-2-yl) |
| III-208 | H | 3-OCH₃ | H | —NH—O—CH₃ |
| III-209 | H | 3-OCH₃ | H | —N(CH₃)(OCH₃) |
| III-210 | H | 3-OCH₃ | H | —N(—(CH₂)₃—O—) |
| III-211 | H | 3-OCH₃ | H | —N(CH₃)₂ |
| III-212 | H | 3-OCH₃ | H | —N(CH₂—C₆H₅)₂ |
| III-213 | H | 3-OCH₃ | H | —N(C₂H₅)₂ |
| III-214 | H | 3-OCH₃ | H | —N(isoC₃H₇)₂ |
| III-215 | H | 3-OCH₃ | H | —N(nC₃H₇)₂ |
| III-216 | H | 3-OCH₃ | H | —N(nC₄H₉)₂ |
| III-217 | H | 3-OCH₃ | H | —N(C₆H₅)₂ |

TABLE 4

A is Me₂Val, B is Val, D is MeVal, E is Pro and F is of Formula II_F, the substituent —(C=O)—G is in position 2 relative to the nitrogen. G is of Formula V_g, VI_g, VII_g, VIII_g or IX_g.

| No. | $R_F$ | $R^1F$ | $R^2F$ | —G |
|---|---|---|---|---|
| IV-1 | H | H | H | —CH₃ |
| IV-2 | H | H | H | —C₂H₅ |
| IV-3 | H | H | H | -nC₃H₇ |
| IV-4 | H | H | H | -isoC₃H₇ |
| IV-5 | H | H | H | -nC₄H₉ |
| IV-6 | H | H | H | -tertC₄H₉ |
| IV-7 | H | H | H | -cycloC₃H₅ |
| IV-8 | H | H | H | -cycloC₄H₇ |
| IV-9 | H | H | H | -cycloC₅H₉ |
| IV-10 | H | H | H | -cycloC₆H₁₁ |
| IV-11 | H | H | H | -cycloC₇H₁₂ |
| IV-12 | H | H | H | —CH₂—O—CH₃ |
| IV-13 | H | H | H | —CH₂—CH₂—O—CH₃ |
| IV-14 | H | H | H | —CH₂—C₆H₅ |
| IV-15 | H | H | H | —C₆H₅ |
| IV-16 | H | H | H | -(4-HO—C₆H₅) |
| IV-17 | H | H | H | -(2-CF₃—C₆H₄) |
| IV-18 | H | H | H | -(3-CF₃—C₆H₄) |
| IV-19 | H | H | H | -(4-CF₃—C₆H₄) |
| IV-20 | H | H | H | -(2-OCH₃—C₆H₄) |
| IV-21 | H | H | H | -(3-OCH₃—C₆H₄) |
| IV-22 | H | H | H | -(4-OCH₃—C₆H₄) |
| IV-23 | H | H | H | -(2-SCH₃—C₆H₄) |
| IV-24 | H | H | H | -(3-SCH₃—C₆H₄) |
| IV-25 | H | H | H | -(4-SCH₃—C₆H₄) |
| IV-26 | H | H | H | -(2-N(CH₃)₂—C₆H₄) |
| IV-27 | H | H | H | -(3-N(CH₃)₂—C₆H₄) |
| IV-28 | H | H | H | -(4-N(CH₃)₂—C₆H₄) |
| IV-29 | H | H | H | -(4-CN—C₆H₄) |
| IV-30 | H | H | H | -(4-Cl—C₆H₄) |
| IV-31 | H | H | H | -(4-Br—C₆H₄] |
| IV-32 | H | H | H | -(4-F—C₆H₄] |
| IV-33 | H | H | H | -(4-CH₃—C₆H₄) |
| IV-34 | H | H | H | -(2-NO₂—C₆H₄) |
| IV-35 | H | H | H | -(3-NO₂—C₆H₄) |
| IV-36 | H | H | H | -(4-NO₂—C₆H₄] |
| IV-37 | H | H | H | -(2,4-OCH₃—C₆H₃) |
| IV-38 | H | H | H | -(3,4-OCH₃—C₆H₃) |
| IV-39 | H | H | H | -(3,4,5-OCH₃—C₆H₂) |
| IV-40 | H | H | H | -(3,4-CH₂OCH₂—C₆H₃) |
| IV-41 | H | H | H | -(2,3-CH₂OCH₂—C₆H₃) |
| IV-42 | H | H | H | -2-pyridinyl |
| IV-43 | H | H | H | -2-furanyl |
| IV-44 | H | H | H | -2-thienyl |
| IV-45 | H | H | H | -3-pyridinyl |
| IV-46 | H | H | H | -3-furanyl |
| IV-47 | H | H | H | -3-thienyl |
| IV-48 | H | H | H | -4-pyridinyl |
| IV-49 | H | H | H | -2-thiazolyl |
| IV-50 | H | H | H | -2-oxazolyl |
| IV-51 | H | H | H | -3-isoxazolyl |
| IV-52 | H | H | H | -4-isoxazolyl |
| IV-53 | H | H | H | -5-isoxazoyl |
| IV-54 | H | H | H | —CF₃ |
| IV-55 | H | H | H | —C₂F₅ |
| IV-56 | H | H | H | —CH₃ |
| IV-57 | H | H | H | —C₂H₅ |
| IV-58 | H | H | H | -nC₃H₇ |
| IV-59 | H | H | H | -tertC₄H₉ |
| IV-60 | H | H | H | —CH₂—C₆H₅ |
| IV-61 | H | H | H | —C₆H₅ |
| IV-62 | H | H | H | —CH₂—COOCH₃ |
| IV-63 | H | H | H | —CH₂—COOC₂H₅ |
| IV-64 | H | H | H | —CF₂—COOCH₃ |
| IV-65 | H | H | H | —CF₂—COOC₂H₅ |
| IV-66 | H | H | H | —CH₂—CONH₂ |
| IV-67 | H | H | H | —CH₂—CONHCH₃ |
| IV-68 | H | H | H | —CH₂—CON(CH₃)₂ |
| IV-69 | H | H | H | —CH₂—CONH—CH₂—C₆H₅ |
| IV-70 | H | H | H | —CH₂—CONH—C₆H₅ |
| IV-71 | H | H | H | —CH₂—CONH(CH₂—C₆H₅)₂ |
| IV-72 | H | H | H | —CH₂—CON(—CH₂—CH₂—CH₂—CH₂—) |
| IV-73 | H | H | H | —CH₂—CON(—CH₂—CH₂—CH₂—CH₂—CH₂) |

TABLE 4-continued

A is Me$_2$Val, B is Val, D is MeVal, E is Pro and F is of
Formula II$_F$, the substituent —(C=O)—G is in position 2
relative to the nitrogen. G is of Formula V$_g$, VI$_g$, VII$_g$, VIII$_g$ or IX$_g$.

| No. | R$_F$ | R$^1$F | R$^2$F | —G |
|---|---|---|---|---|
| IV-74 | H | H | H | —CH$_2$—CH$_2$—COOCH$_3$ |
| IV-75 | H | H | H | —CH$_2$—CH$_2$—COOC$_2$H$_5$ |
| IV-76 | H | H | H | —CH$_2$—CH$_2$—CONH$_2$ |
| IV-77 | H | H | H | —CH$_2$—CH$_2$—CONHCH$_3$ |
| IV-78 | H | H | H | —CH$_2$—CH$_2$—CON(CH$_3$)$_2$ |
| IV-79 | H | H | H | —CH$_2$—CH$_2$—CONH—CH$_2$—C$_6$H$_5$ |
| IV-80 | H | H | H | —CH$_2$—CH$_2$—CONH—C$_6$H$_5$ |
| IV-81 | H | H | H | —CH$_2$—CH$_2$—CONH(CH$_2$—C$_6$H$_5$)$_2$ |
| IV-82 | H | H | H | —CH$_2$—CH$_2$—CON(—CH$_2$—CH$_2$—CH$_2$—CH$_2$—) |
| IV-83 | H | H | H | —CH$_2$—CH$_2$—CON(—CH$_2$—(CH$_2$)$_3$—CH$_2$) |
| IV-84 | H | H | H | —CH$_2$—COCH$_3$ |
| IV-85 | H | H | H | —CH$_2$—CH$_2$—COCH$_3$ |
| IV-86 | H | H | H | —CH$_2$—COC$_2$H$_5$ |
| IV-87 | H | H | H | —CH$_2$—CH$_2$—COC$_2$H$_5$ |
| IV-88 | H | H | H | —CH$_2$—CO—C$_6$H$_5$ |
| IV-89 | H | H | H | —CH$_2$—CH$_2$—CO—C$_6$H$_5$ |
| IV-90 | H | H | H | —CH$_2$—CO—CH$_2$—C$_6$H$_5$ |
| IV-91 | H | H | H | —CH$_2$—CH$_2$—CO—CH$_2$—C$_6$H$_5$ |
| IV-92 | H | H | H | —CH$_2$—SOC$_6$H$_5$ |
| IV-93 | H | H | H | —CH$_2$—SOCH$_3$ |
| IV-94 | H | H | H | —CH$_2$—SO(4-CH$_3$—C$_6$H$_4$) |
| IV-95 | H | H | H | —CH$_2$—SO$_2$C$_6$H$_5$ |
| IV-96 | H | H | H | —CH$_2$—SO$_2$CH$_3$ |
| IV-97 | H | H | H | —CH$_2$—SO$_2$(4-CH$_3$—C$_6$H$_4$) |
| IV-98 | H | H | H | —CH$_2$—CH$_2$—SOC$_6$H$_5$ |
| IV-99 | H | H | H | —CH$_2$—CH$_2$—SOCH$_3$ |
| IV-100 | H | H | H | —CH$_2$—CH$_2$—SO(4-CH$_3$—C$_6$H$_4$) |
| IV-101 | H | H | H | —CH$_2$—CH$_2$—SO$_2$C$_6$H$_5$ |
| IV-102 | H | H | H | —CH$_2$—CH$_2$—SO$_2$CH$_3$ |
| IV-103 | H | H | H | —CH$_2$—CH$_2$—SO$_2$(4-CH$_3$—C$_6$H$_4$) |
| IV-104 | CH$_3$ | H | H | —CH$_3$ |
| IV-105 | CH$_3$ | H | H | —C$_2$H$_5$ |
| IV-106 | CH$_3$ | H | H | -nC$_3$H$_7$ |
| IV-107 | CH$_3$ | H | H | -isoC$_3$H$_7$ |
| IV-108 | CH$_3$ | H | H | -nC$_4$H$_9$ |
| IV-109 | CH$_3$ | H | H | -tertC$_4$H$_9$ |
| IV-110 | CH$_3$ | H | H | -cycloC$_3$H$_5$ |
| IV-111 | CH$_3$ | H | H | -cycloC$_4$H$_7$ |
| IV-112 | CH$_3$ | H | H | -cycloC$_5$H$_9$ |
| IV-113 | CH$_3$ | H | H | -cycloC$_6$H$_{11}$ |
| IV-114 | CH$_3$ | H | H | -cycloC$_7$H$_{12}$ |
| IV-115 | CH$_3$ | H | H | —CH$_2$—O—CH$_3$ |
| IV-116 | CH$_3$ | H | H | —CH$_2$—CH$_2$—O—CH$_3$ |
| IV-117 | CH$_3$ | H | H | —CH$_2$—C$_6$H$_5$ |
| IV-118 | CH$_3$ | H | H | —C$_6$H$_5$ |
| IV-119 | CH$_3$ | H | H | -(4-HO—C$_6$H$_5$) |
| IV-120 | CH$_3$ | H | H | -(2-CF$_3$—C$_6$H$_4$) |
| IV-121 | CH$_3$ | H | H | -(3-CF$_3$—C$_6$H$_4$) |
| IV-122 | CH$_3$ | H | H | -(4-CF$_3$—C$_6$H$_4$) |
| IV-123 | CH$_3$ | H | H | -(2-OCH$_3$—C$_6$H$_4$) |
| IV-124 | CH$_3$ | H | H | -(3-OCH$_3$—C$_6$H$_4$) |
| IV-125 | CH$_3$ | H | H | -(4-OCH$_3$—C$_6$H$_4$) |
| IV-126 | CH$_3$ | H | H | -(2-SCH$_3$—C$_6$H$_4$) |
| IV-127 | CH$_3$ | H | H | -(3-SCH$_3$—C$_6$H$_4$) |
| IV-128 | CH$_3$ | H | H | -(4-SCH$_3$—C$_6$H$_4$) |
| IV-129 | CH$_3$ | H | H | -(2-N(CH$_3$)$_2$—C$_6$H$_4$) |
| IV-130 | CH$_3$ | H | H | -(3-N(CH$_3$)$_2$—C$_6$H$_4$) |
| IV-131 | CH$_3$ | H | H | -(4-N(CH$_3$)$_2$—C$_6$H$_4$) |
| IV-132 | CH$_3$ | H | H | -(4-CN—C$_6$H$_4$) |
| IV-133 | CH$_3$ | H | H | -(4-Cl—C$_6$H$_4$) |
| IV-134 | CH$_3$ | H | H | -(4-Br—C$_6$H$_4$] |
| IV-135 | CH$_3$ | H | H | -(4-F—C$_6$H$_4$] |
| IV-136 | CH$_3$ | H | H | -(4-CH$_3$—C$_6$H$_4$) |
| IV-137 | CH$_3$ | H | H | -(2-NO$_2$—C$_6$H$_4$) |
| IV-138 | CH$_3$ | H | H | -(3-NO$_2$—C$_6$H$_4$) |
| IV-139 | CH$_3$ | H | H | -(4-NO$_2$—C$_6$H$_4$] |
| IV-140 | CH$_3$ | H | H | -(2,4-OCH$_3$—C$_6$H$_3$) |
| IV-141 | CH$_3$ | H | H | -(3,4-OCH$_3$—C$_6$H$_3$) |
| IV-142 | CH$_3$ | H | H | -(3,4,5-OCH$_3$—C$_6$H$_2$) |
| IV-143 | CH$_3$ | H | H | -(3,4-CH$_2$OCH$_2$—C$_6$H$_3$) |
| IV-144 | CH$_3$ | H | H | -(2,3-CH$_2$OCH$_2$—C$_6$H$_3$) |
| IV-145 | CH$_3$ | H | H | -2-pyridinyl |
| IV-146 | CH$_3$ | H | H | -2-furanyl |

TABLE 4-continued

A is Me$_2$Val, B is Val, D is MeVal, E is Pro and F is of Formula II$_f$, the substituent —(C=O)—G is in position 2 relative to the nitrogen. G is of Formula V$_g$, VI$_g$, VII$_g$, VIII$_g$ or IX$_g$.

| No. | R$_F$ | R$^1$F | R$^2$F | —G |
|---|---|---|---|---|
| IV-147 | CH$_3$ | H | H | -2-thienyl |
| IV-148 | CH$_3$ | H | H | -3-pyridinyl |
| IV-149 | CH$_3$ | H | H | -3-furanyl |
| IV-150 | CH$_3$ | H | H | -3-thienyl |
| IV-151 | CH$_3$ | H | H | -4-pyridinyl |
| IV-152 | CH$_3$ | H | H | -2-thiazolyl |
| IV-153 | CH$_3$ | H | H | -2-oxazolyl |
| IV-154 | CH$_3$ | H | H | -3-isoxazolyl |
| IV-155 | CH$_3$ | H | H | -4-isoxazolyl |
| IV-156 | CH$_3$ | H | H | -5-isoxazoyl |
| IV-157 | CH$_3$ | H | H | —CF$_3$ |
| IV-158 | CH$_3$ | H | H | —C$_2$F$_5$ |
| IV-159 | CH$_3$ | H | H | —CH$_3$ |
| IV-160 | CH$_3$ | H | H | —C$_2$H$_5$ |
| IV-161 | CH$_3$ | H | H | -nC$_3$H$_7$ |
| IV-162 | CH$_3$ | H | H | -tertC$_4$H$_9$ |
| IV-163 | CH$_3$ | H | H | —CH$_2$—C$_6$H$_5$ |
| IV-164 | CH$_3$ | H | H | —C$_6$H$_5$ |
| IV-165 | CH$_3$ | H | H | —CH$_2$—COOCH$_3$ |
| IV-166 | CH$_3$ | H | H | —CH$_2$—COOC$_2$H$_5$ |
| IV-167 | CH$_3$ | H | H | —CF$_2$—COOCH$_3$ |
| IV-168 | CH$_3$ | H | H | —CF$_2$—COOC$_2$H$_5$ |
| IV-169 | CH$_3$ | H | H | —CH$_2$—CONH$_2$ |
| IV-170 | CH$_3$ | H | H | —CH$_2$—CONHCH$_3$ |
| IV-171 | CH$_3$ | H | H | —CH$_2$—CON(CH$_3$)$_2$ |
| IV-172 | CH$_3$ | H | H | —CH$_2$—CONH—CH$_2$—C$_6$H$_5$ |
| IV-173 | CH$_3$ | H | H | —CH$_2$—CONH—C$_6$H$_5$ |
| IV-174 | CH$_3$ | H | H | —CH$_2$—CONH(CH$_2$—C$_6$H$_5$)$_2$ |
| IV-175 | CH$_3$ | H | H | —CH$_2$—CON(—CH$_2$—CH$_2$—CH$_2$—CH$_2$—) |
| IV-176 | CH$_3$ | H | H | —CH$_2$—CON(—CH$_2$—CH$_2$—CH$_2$—CH$_2$—CH$_2$) |
| IV-177 | CH$_3$ | H | H | —CH$_2$—CH$_2$—COOCH$_3$ |
| IV-178 | CH$_3$ | H | H | —CH$_2$—CH$_2$—COOC$_2$H$_5$ |
| IV-179 | CH$_3$ | H | H | —CH$_2$—CH$_2$—CONH$_2$ |
| IV-180 | CH$_3$ | H | H | —CH$_2$—CH$_2$—CONHCH$_3$ |
| IV-181 | CH$_3$ | H | H | —CH$_2$—CH$_2$—CON(CH$_3$)$_2$ |
| IV-182 | CH$_3$ | H | H | —CH$_2$—CH$_2$—CONH—CH$_2$—C$_6$H$_5$ |
| IV-183 | CH$_3$ | H | H | —CH$_2$—CH$_2$—CONH—C$_6$H$_5$ |
| IV-184 | CH$_3$ | H | H | —CH$_2$—CH$_2$—CONH(CH$_2$—C$_6$H$_5$)$_2$ |
| IV-185 | CH$_3$ | H | H | —CH$_2$—CH$_2$—CON(—CH$_2$—CH$_2$—CH$_2$—CH$_2$—) |
| IV-186 | CH$_3$ | H | H | —CH$_2$—CH$_2$—CON(—CH$_2$—(CH$_2$)$_3$—CH$_2$) |
| IV-187 | CH$_3$ | H | H | —CH$_2$—COCH$_3$ |
| IV-188 | CH$_3$ | H | H | —CH$_2$—CH$_2$—COCH$_3$ |
| IV-189 | CH$_3$ | H | H | —CH$_2$—COC$_2$H$_5$ |
| IV-190 | CH$_3$ | H | H | —CH$_2$—CH$_2$—COC$_2$H$_5$ |
| IV-191 | CH$_3$ | H | H | —CH$_2$—CO—C$_6$H$_5$ |
| IV-192 | CH$_3$ | H | H | —CH$_2$—CH$_2$—CO—C$_6$H$_5$ |
| IV-193 | CH$_3$ | H | H | —CH$_2$—CO—CH$_2$—C$_6$H$_5$ |
| IV-194 | CH$_3$ | H | H | —CH$_2$—CH$_2$—CO—CH$_2$—C$_6$H$_5$ |
| IV-195 | CH$_3$ | H | H | —CH$_2$—SOC$_6$H$_5$ |
| IV-196 | CH$_3$ | H | H | —CH$_2$—SOCH$_3$ |
| IV-197 | CH$_3$ | H | H | —CH$_2$—SO(4-CH$_3$—C$_6$H$_4$) |
| IV-198 | CH$_3$ | H | H | —CH$_2$—SO$_2$C$_6$H$_5$ |
| IV-199 | CH$_3$ | H | H | —CH$_2$—SO$_2$CH$_3$ |
| IV-200 | CH$_3$ | H | H | —CH$_2$—SO$_2$(4-CH$_3$—C$_6$H$_4$) |
| IV-201 | CH$_3$ | H | H | —CH$_2$—CH$_2$—SOC$_6$H$_5$ |
| IV-202 | CH$_3$ | H | H | —CH$_2$—CH$_2$—SOCH$_3$ |
| IV-203 | CH$_3$ | H | H | —CH$_2$—CH$_2$—SO(4-CH$_3$—C$_6$H$_4$) |
| IV-204 | CH$_3$ | H | H | —CH$_2$—CH$_2$—SO$_2$C$_6$H$_5$ |
| IV-205 | CH$_3$ | H | H | —CH$_2$—CH$_2$—SO$_2$CH$_3$ |
| IV-206 | CH$_3$ | H | H | —CH$_2$—CH$_2$—SO$_2$(4-CH$_3$—C$_6$H$_4$) |

TABLE 5

A is Me₂Val, B is Val, D is MeVal, E is Pro and F is of Formula II_F, the substituent —(C=O)—G is in position 3 relative to the nitrogen. G is of Formula V_g, VI_g, VII_g, VIII_g or IX_g.

| No. | R_F | R¹F | R²F | —G |
|---|---|---|---|---|
| V-1 | H | H | H | —CH₃ |
| V-2 | H | H | H | —C₂H₅ |
| V-3 | H | H | H | -nC₃H₇ |
| V-4 | H | H | H | -isoC₃H₇ |
| V-5 | H | H | H | -nC₄H₉ |
| V-6 | H | H | H | -tertC₄H₉ |
| V-7 | H | H | H | -cycloC₃H₅ |
| V-8 | H | H | H | -cycloC₄H₇ |
| V-9 | H | H | H | -cycloC₅H₉ |
| V-10 | H | H | H | -cycloC₆H₁₁ |
| V-11 | H | H | H | -cycloC₇H₁₂ |
| V-12 | H | H | H | —CH₂—O—CH₃ |
| V-13 | H | H | H | —CH₂—CH₂—O—CH₃ |
| V-14 | H | H | H | —CH₂—C₆H₅ |
| V-15 | H | H | H | —C₆H₅ |
| V-16 | H | H | H | -(4-HO—C₆H₅) |
| V-17 | H | H | H | -(2-CF₃—C₆H₄) |
| V-18 | H | H | H | -(3-CF₃—C₆H₄) |
| V-19 | H | H | H | -(4-CF₃—C₆H₄) |
| V-20 | H | H | H | -(2-OCH₃—C₆H₄) |
| V-21 | H | H | H | -(3-OCH₃—C₆H₄) |
| V-22 | H | H | H | -(4-OCH₃—C₆H₄) |
| V-23 | H | H | H | -(2-SCH₃—C₆H₄) |
| V-24 | H | H | H | -(3-SCH₃—C₆H₄) |
| V-25 | H | H | H | -(4-SCH₃—C₆H₄) |
| V-26 | H | H | H | -(2-N(CH₃)₂—C₆H₄) |
| V-27 | H | H | H | -(3-N(CH₃)₂—C₆H₄) |
| V-28 | H | H | H | -(4-N(CH₃)₂—C₆H₄) |
| V-29 | H | H | H | -(4-CN—C₆H₄) |
| V-30 | H | H | H | -(4-Cl—C₆H₄) |
| V-31 | H | H | H | -(4-Br—C₆H₄] |
| V-32 | H | H | H | -(4-F—C₆H₄] |
| V-33 | H | H | H | -(4-CH₃—C₆H₄) |
| V-34 | H | H | H | -(2-NO₂—C₆H₄) |
| V-35 | H | H | H | -(3-NO₂—C₆H₄) |
| V-36 | H | H | H | -(4-NO₂—C₆H₄] |
| V-37 | H | H | H | -(2,4-OCH₃—C₆H₃) |
| V-38 | H | H | H | -(3,4-OCH₃—C₆H₃) |
| V-39 | H | H | H | -(3,4,5-OCH₃—C₆H₂) |
| V-40 | H | H | H | -(3,4-CH₂OCH₂—C₆H₃) |
| V-41 | H | H | H | -(2,3-CH₂OCH₂—C₆H₃) |
| V-42 | H | H | H | -2-pyridinyl |
| V-43 | H | H | H | -2-furanyl |
| V-44 | H | H | H | -2-thienyl |
| V-45 | H | H | H | -3-pyridinyl |
| V-46 | H | H | H | -3-furanyl |
| V-47 | H | H | H | -3-thienyl |
| V-48 | H | H | H | -4-pyridinyl |
| V-49 | H | H | H | -2-thiazolyl |
| V-50 | H | H | H | -2-oxazolyl |
| V-51 | H | H | H | -3-isoxazolyl |
| V-52 | H | H | H | -4-isoxazolyl |
| V-53 | H | H | H | -5-isoxazoyl |
| V-54 | H | H | H | —CF₃ |
| V-55 | H | H | H | —C₂F₅ |
| V-56 | H | H | H | —CH₃ |
| V-57 | H | H | H | —C₂H₅ |
| V-58 | H | H | H | -nC₃H₇ |
| V-59 | H | H | H | -tertC₄H₉ |
| V-60 | H | H | H | —CH₂—C₆H₅ |
| V-61 | H | H | H | —C₆H₅ |
| V-62 | H | H | H | —CH₂—COOCH₃ |
| V-63 | H | H | H | —CH₂—COOC₂H₅ |
| V-64 | H | H | H | —CF₂—COOCH₃ |
| V-65 | H | H | H | —CF₂—COOC₂H₅ |
| V-66 | H | H | H | —CH₂—CONH₂ |
| V-67 | H | H | H | —CH₂—CONHCH₃ |
| V-68 | H | H | H | —CH₂—CON(CH₃)₂ |
| V-69 | H | H | H | —CH₂—CONH—CH₂—C₆H₅ |
| V-70 | H | H | H | —CH₂—CONH—C₆H₅ |
| V-71 | H | H | H | —CH₂—CONH(CH₂—C₆H₅)₂ |
| V-72 | H | H | H | —CH₂—CON(—CH₂—CH₂—CH₂—CH₂—) |
| V-73 | H | H | H | —CH₂—CON(—CH₂—CH₂—CH₂—CH₂—CH₂) |

TABLE 5-continued

A is Me$_2$Val, B is Val, D is MeVal, E is Pro and F is of
Formula II$_F$, the substituent —(C=O)—G is in position 3
relative to the nitrogen. G is of Formula V$_g$, VI$_g$, VII$_g$, VIII$_g$ or IX$_g$.

| No. | R$_F$ | R$^1$F | R$^2$F | —G |
|---|---|---|---|---|
| V-74 | H | H | H | —CH$_2$—CH$_2$—COOCH$_3$ |
| V-75 | H | H | H | —CH$_2$—CH$_2$—COOC$_2$H$_5$ |
| V-76 | H | H | H | —CH$_2$—CH$_2$—CONH$_2$ |
| V-77 | H | H | H | —CH$_2$—CH$_2$—CONHCH$_3$ |
| V-78 | H | H | H | —CH$_2$—CH$_2$—CON(CH$_3$)$_2$ |
| V-79 | H | H | H | —CH$_2$—CH$_2$—CONH—CH$_2$—C$_6$H$_5$ |
| V-80 | H | H | H | —CH$_2$—CH$_2$—CONH—C$_6$H$_5$ |
| V-81 | H | H | H | —CH$_2$—CH$_2$—CONH(CH$_2$—C$_6$H$_5$)$_2$ |
| V-82 | H | H | H | —CH$_2$—CH$_2$—CON(—CH$_2$—CH$_2$—CH$_2$—CH$_2$—) |
| V-83 | H | H | H | —CH$_2$—CH$_2$—CON(—CH$_2$—(CH$_2$)$_3$—CH$_2$) |
| V-84 | H | H | H | —CH$_2$—COCH$_3$ |
| V-85 | H | H | H | —CH$_2$—CH$_2$—COCH$_3$ |
| V-86 | H | H | H | —CH$_2$—COC$_2$H$_5$ |
| V-87 | H | H | H | —CH$_2$—CH$_2$—COC$_2$H$_5$ |
| V-88 | H | H | H | —CH$_2$—CO—C$_6$H$_5$ |
| V-89 | H | H | H | —CH$_2$—CH$_2$—CO—C$_6$H$_5$ |
| V-90 | H | H | H | —CH$_2$—CO—CH$_2$—C$_6$H$_5$ |
| V-91 | H | H | H | —CH$_2$—CH$_2$—CO—CH$_2$—C$_6$H$_5$ |
| V-92 | H | H | H | —CH$_2$—SOC$_6$H$_5$ |
| V-93 | H | H | H | —CH$_2$—SOCH$_3$ |
| V-94 | H | H | H | —CH$_2$—SO(4-CH$_3$—C$_6$H$_4$) |
| V-95 | H | H | H | —CH$_2$—SO$_2$C$_6$H$_5$ |
| V-96 | H | H | H | —CH$_2$—SO$_2$CH$_3$ |
| V-97 | H | H | H | —CH$_2$—SO$_2$(4-CH$_3$—C$_6$H$_4$) |
| V-98 | H | H | H | —CH$_2$—CH$_2$—SOC$_6$H$_5$ |
| V-99 | H | H | H | —CH$_2$—CH$_2$—SOCH$_3$ |
| V-100 | H | H | H | —CH$_2$—CH$_2$—SO(4-CH$_3$—C$_6$H$_4$) |
| V-101 | H | H | H | —CH$_2$—CH$_2$—SO$_2$C$_6$H$_5$ |
| V-102 | H | H | H | —CH$_2$—CH$_2$—SO$_2$CH$_3$ |
| V-103 | H | H | H | —CH$_2$—CH$_2$—SO$_2$(4-CH$_3$—C$_6$H$_4$) |
| V-104 | CH$_3$ | H | H | —CH$_3$ |
| V-105 | CH$_3$ | H | H | —C$_2$H$_5$ |
| V-106 | CH$_3$ | H | H | -nC$_3$H$_7$ |
| V-107 | CH$_3$ | H | H | -isoC$_3$H$_7$ |
| V-108 | CH$_3$ | H | H | -nC$_4$H$_9$ |
| V-109 | CH$_3$ | H | H | -tertC$_4$H$_9$ |
| V-110 | CH$_3$ | H | H | -cycloC$_3$H$_5$ |
| V-111 | CH$_3$ | H | H | -cycloC$_4$H$_7$ |
| V-112 | CH$_3$ | H | H | -cycloC$_5$H$_9$ |
| V-113 | CH$_3$ | H | H | -cycloC$_6$H$_{11}$ |
| V-114 | CH$_3$ | H | H | -cycloC$_7$H$_{12}$ |
| V-115 | CH$_3$ | H | H | —CH$_2$—O—CH$_3$ |
| V-116 | CH$_3$ | H | H | —CH$_2$—CH$_2$—O—CH$_3$ |
| V-117 | CH$_3$ | H | H | —CH$_2$—C$_6$H$_5$ |
| V-118 | CH$_3$ | H | H | —C$_6$H$_5$ |
| V-119 | CH$_3$ | H | H | -(4-HO—C$_6$H$_5$) |
| V-120 | CH$_3$ | H | H | -(2-CF$_3$—C$_6$H$_4$) |
| V-121 | CH$_3$ | H | H | -(3-CF$_3$—C$_6$H$_4$) |
| V-122 | CH$_3$ | H | H | -(4-CF$_3$—C$_6$H$_4$) |
| V-123 | CH$_3$ | H | H | -(2-OCH$_3$—C$_6$H$_4$) |
| V-124 | CH$_3$ | H | H | -(3-OCH$_3$—C$_6$H$_4$) |
| V-125 | CH$_3$ | H | H | -(4-OCH$_3$—C$_6$H$_4$) |
| V-126 | CH$_3$ | H | H | -(2-SCH$_3$—C$_6$H$_4$) |
| V-127 | CH$_3$ | H | H | -(3-SCH$_3$—C$_6$H$_4$) |
| V-128 | CH$_3$ | H | H | -(4-SCH$_3$—C$_6$H$_4$) |
| V-129 | CH$_3$ | H | H | -(2-N(CH$_3$)$_2$—C$_6$H$_4$) |
| V-130 | CH$_3$ | H | H | -(3-N(CH$_3$)$_2$—C$_6$H$_4$) |
| V-131 | CH$_3$ | H | H | -(4-N(CH$_3$)$_2$—C$_6$H$_4$) |
| V-132 | CH$_3$ | H | H | -(4-CN—C$_6$H$_4$) |
| V-133 | CH$_3$ | H | H | -(4-Cl—C$_6$H$_4$) |
| V-134 | CH$_3$ | H | H | -(4-Br—C$_6$H$_4$] |
| V-135 | CH$_3$ | H | H | -(4-F—C$_6$H$_4$] |
| V-136 | CH$_3$ | H | H | -(4-CH$_3$—C$_6$H$_4$) |
| V-137 | CH$_3$ | H | H | -(2-NO$_2$—C$_6$H$_4$) |
| V-138 | CH$_3$ | H | H | -(3-NO$_2$—C$_6$H$_4$) |
| V-139 | CH$_3$ | H | H | -(4-NO$_2$—C$_6$H$_4$] |
| V-140 | CH$_3$ | H | H | -(2,4-OCH$_3$—C$_6$H$_3$) |
| V-141 | CH$_3$ | H | H | -(3,4-OCH$_3$—C$_6$H$_3$) |
| V-142 | CH$_3$ | H | H | -(3,4,5-OCH$_3$—C$_6$H$_2$) |
| V-143 | CH$_3$ | H | H | -(3,4-CH$_2$OCH$_2$—C$_6$H$_3$) |
| V-144 | CH$_3$ | H | H | -(2,3-CH$_2$OCH$_2$—C$_6$H$_3$) |
| V-145 | CH$_3$ | H | H | -2-pyridinyl |
| V-146 | CH$_3$ | H | H | -2-furanyl |

TABLE 5-continued

A is Me$_2$Val, B is Val, D is MeVal, E is Pro and F is of
Formula II$_f$, the substituent —(C=O)—G is in position 3
relative to the nitrogen. G is of Formula V$_g$, VI$_g$, VII$_g$, VIII$_g$ or IX$_g$.

| No. | R$_F$ | R$^1$F | R$^2$F | —G |
|---|---|---|---|---|
| V-147 | CH$_3$ | H | H | -2-thienyl |
| V-148 | CH$_3$ | H | H | -3-pyridinyl |
| V-149 | CH$_3$ | H | H | -3-furanyl |
| V-150 | CH$_3$ | H | H | -3-thienyl |
| V-151 | CH$_3$ | H | H | -4-pyridinyl |
| V-152 | CH$_3$ | H | H | -2-thiazolyl |
| V-153 | CH$_3$ | H | H | -2-oxazolyl |
| V-154 | CH$_3$ | H | H | -3-isoxazolyl |
| V-155 | CH$_3$ | H | H | -4-isoxazolyl |
| V-156 | CH$_3$ | H | H | -5-isoxazoyl |
| V-157 | CH$_3$ | H | H | —CF$_3$ |
| V-158 | CH$_3$ | H | H | —C$_2$F$_5$ |
| V-159 | CH$_3$ | H | H | —CH$_3$ |
| V-160 | CH$_3$ | H | H | —C$_2$H$_5$ |
| V-161 | CH$_3$ | H | H | -nC$_3$H$_7$ |
| V-162 | CH$_3$ | H | H | -tertC$_4$H$_9$ |
| V-163 | CH$_3$ | H | H | —CH$_2$—C$_6$H$_5$ |
| V-164 | CH$_3$ | H | H | —C$_6$H$_5$ |
| V-165 | CH$_3$ | H | H | —CH$_2$—COOCH$_3$ |
| V-166 | CH$_3$ | H | H | —CH$_2$—COOC$_2$H$_5$ |
| V-167 | CH$_3$ | H | H | —CF$_2$—COOCH$_3$ |
| V-168 | CH$_3$ | H | H | —CF$_2$—COOC$_2$H$_5$ |
| V-169 | CH$_3$ | H | H | —CH$_2$—CONH$_2$ |
| V-170 | CH$_3$ | H | H | —CH$_2$—CONHCH$_3$ |
| V-171 | CH$_3$ | H | H | —CH$_2$—CON(CH$_3$)$_2$ |
| V-172 | CH$_3$ | H | H | —CH$_2$—CONH—CH$_2$—C$_6$H$_5$ |
| V-173 | CH$_3$ | H | H | —CH$_2$—CONH—C$_6$H$_5$ |
| V-174 | CH$_3$ | H | H | —CH$_2$—CONH(CH$_2$—C$_6$H$_5$)$_2$ |
| V-175 | CH$_3$ | H | H | —CH$_2$—CON(—CH$_2$—CH$_2$—CH$_2$—CH$_2$—) |
| V-176 | CH$_3$ | H | H | —CH$_2$—CON(—CH$_2$—CH$_2$—CH$_2$—CH$_2$—CH$_2$) |
| V-177 | CH$_3$ | H | H | —CH$_2$—CH$_2$—COOCH$_3$ |
| V-178 | CH$_3$ | H | H | —CH$_2$—CH$_2$—COOC$_2$H$_5$ |
| V-179 | CH$_3$ | H | H | —CH$_2$—CH$_2$—CONH$_2$ |
| V-180 | CH$_3$ | H | H | —CH$_2$—CH$_2$—CONHCH$_3$ |
| V-181 | CH$_3$ | H | H | —CH$_2$—CH$_2$—CON(CH$_3$)$_2$ |
| V-182 | CH$_3$ | H | H | —CH$_2$—CH$_2$—CONH—CH$_2$—C$_6$H$_5$ |
| V-183 | CH$_3$ | H | H | —CH$_2$—CH$_2$—CONH—C$_6$H$_5$ |
| V-184 | CH$_3$ | H | H | —CH$_2$—CH$_2$—CONH(CH$_2$—C$_6$H$_5$)$_2$ |
| V-185 | CH$_3$ | H | H | —CH$_2$—CH$_2$—CON(—CH$_2$—CH$_2$—CH$_2$—CH$_2$—) |
| V-186 | CH$_3$ | H | H | —CH$_2$—CH$_2$—CON(—CH$_2$—(CH$_2$)$_3$—CH$_2$) |
| V-187 | CH$_3$ | H | H | —CH$_2$—COCH$_3$ |
| V-188 | CH$_3$ | H | H | —CH$_2$—CH$_2$—COCH$_3$ |
| V-189 | CH$_3$ | H | H | —CH$_2$—COC$_2$H$_5$ |
| V-190 | CH$_3$ | H | H | —CH$_2$—CH$_2$—COC$_2$H$_5$ |
| V-191 | CH$_3$ | H | H | —CH$_2$—CO—C$_6$H$_5$ |
| V-192 | CH$_3$ | H | H | —CH$_2$—CH$_2$—CO—C$_6$H$_5$ |
| V-193 | CH$_3$ | H | H | —CH$_2$—CO—CH$_2$—C$_6$H$_5$ |
| V-194 | CH$_3$ | H | H | —CH$_2$—CH$_2$—CO—CH$_2$—C$_6$H$_5$ |
| V-195 | CH$_3$ | H | H | —CH$_2$—SOC$_6$H$_5$ |
| V-196 | CH$_3$ | H | H | —CH$_2$—SOCH$_3$ |
| V-197 | CH$_3$ | H | H | —CH$_2$—SO(4-CH$_3$—C$_6$H$_4$) |
| V-198 | CH$_3$ | H | H | —CH$_2$—SO$_2$C$_6$H$_5$ |
| V-199 | CH$_3$ | H | H | —CH$_2$—SO$_2$CH$_3$ |
| V-200 | CH$_3$ | H | H | —CH$_2$—SO$_2$(4-CH$_3$—C$_6$H$_4$) |
| V-201 | CH$_3$ | H | H | —CH$_2$—CH$_2$—SOC$_6$H$_5$ |
| V-202 | CH$_3$ | H | H | —CH$_2$—CH$_2$—SOCH$_3$ |
| V-203 | CH$_3$ | H | H | —CH$_2$—CH$_2$—SO(4-CH$_3$—C$_6$H$_4$) |
| V-204 | CH$_3$ | H | H | —CH$_2$—CH$_2$—SO$_2$C$_6$H$_5$ |
| V-205 | CH$_3$ | H | H | —CH$_2$—CH$_2$—SO$_2$CH$_3$ |
| V-206 | CH$_3$ | H | H | —CH$_2$—CH$_2$—SO$_2$(4-CH$_3$—C$_6$H$_4$) |

TABLE 6

A is Me$_2$Val, B is Val, D is MeVal, E is Pro and F is of Formula II$_f$, the substituent -(C=C)-G is in position 4 relative to the nitrogen G is of Formula V$_g$, VI$_g$, VII$_g$, VIII$_g$ or IX$_g$.

| No. | RF | R$^1$F | R$^2$F | -G |
|---|---|---|---|---|
| VI-1 | H | H | H | —CH$_3$ |
| VI-2 | H | H | H | —C$_2$H$_5$ |
| VI-3 | H | H | H | -nC$_3$H$_7$ |
| VI-4 | H | H | H | -isoC$_3$H$_7$ |
| VI-5 | H | H | H | -nC$_4$H$_9$ |
| VI-6 | H | H | H | -tertC$_4$H$_9$ |
| VI-7 | H | H | H | -cycloC$_3$H$_9$ |
| VI-8 | H | H | H | -cycloC$_4$H$_7$ |
| VI-9 | H | H | H | -cycloC$_5$H$_9$ |
| VI-10 | H | H | H | -cycloC$_6$H$_{11}$ |
| VI-11 | H | H | H | -cycloC$_7$H$_{12}$ |
| VI-12 | H | H | H | —CH$_2$—O—CH$_3$ |
| VI-13 | H | H | H | —CH$_2$—CH$_2$—O—CH$_2$ |
| VI-14 | H | H | H | —CH$_2$—C$_6$H$_5$ |
| VI-15 | H | H | H | —C$_6$H$_5$ |
| VI-16 | H | H | H | -(4-HO—C$_6$H$_5$) |
| VI-17 | H | H | H | -(2-CF$_3$—C$_6$H$_4$) |
| VI-18 | H | H | H | -(3-CF$_3$—C$_6$H$_4$) |
| VI-19 | H | H | H | -(4-CF$_3$—C$_6$H$_4$) |
| VI-20 | H | H | H | -(2-OCH$_3$—C$_6$H$_4$) |
| VI-21 | H | H | H | -(3-OCH$_3$—C$_6$H$_4$) |
| VI-22 | H | H | H | -(4-OCH$_3$—C$_6$H$_4$) |
| VI-23 | H | H | H | -(2-SCH$_3$—C$_6$H$_4$) |
| VI-24 | H | H | H | -(3-SCH$_3$—C$_6$H$_4$) |
| VI-25 | H | H | H | -(4-SCH$_3$—C$_6$H$_4$) |
| VI-26 | H | H | H | -(2-N(CH$_3$)$_2$—C$_6$H$_4$) |
| VI-27 | H | H | H | -(3-N(CH$_3$)$_2$—C$_6$H$_4$) |
| VI-28 | H | H | H | -(4-N(CH$_3$)$_2$—C$_6$H$_4$) |
| VI-29 | H | H | H | -(4-CN—C$_6$H$_4$) |
| VI-30 | H | H | H | -(4-Cl—C$_6$H$_4$) |
| VI-31 | H | H | H | -(4-Br—C$_6$H$_4$] |
| VI-32 | H | H | H | -(4-F—C$_6$H$_4$] |
| VI-33 | H | H | H | -(4-CH$_3$—C$_6$H$_4$) |
| VI-34 | H | H | H | -(2-NO$_2$—C$_6$H$_4$) |
| VI-35 | H | H | H | -(3-NO$_2$—C$_6$H$_4$) |
| VI-36 | H | H | H | -(4-NO$_2$—C$_6$H$_4$] |
| VI-37 | H | H | H | -(2,4-OCH$_3$—C$_6$H$_3$) |
| VI-38 | H | H | H | -(3,4-OCH$_3$—C$_6$H$_3$) |
| VI-39 | H | H | H | -(3,4,5-OCH$_3$—C$_6$H$_2$) |
| VI-40 | H | H | H | -(3,4-CH$_2$OCH$_2$—C$_6$H$_3$) |
| VI-41 | H | H | H | -(2,3-CH$_2$OCH$_2$—C$_6$H$_3$) |
| VI-42 | H | H | H | -2-pyridinyl |
| VI-43 | H | H | H | -2-furanyl |
| VI-44 | H | H | H | -2-thienyl |
| VI-45 | H | H | H | -3-pyridinyl |
| VI-46 | H | H | H | -3-furanyl |
| VI-47 | H | H | H | -3-thienyl |
| VI-48 | H | H | H | -4-pyridinyl |
| VI-49 | H | H | H | -2-thiazolyl |
| VI-50 | H | H | H | -2-oxazolyl |
| VI-51 | H | H | H | -3-isoxazolyl |
| VI-52 | H | H | H | -4-isoxazolyl |
| VI-53 | H | H | H | -5-isoxazolyl |
| VI-54 | H | H | H | —CF$_3$ |
| VI-55 | H | H | H | —C$_2$F$_5$ |
| VI-56 | H | H | H | —CH$_3$ |
| VI-57 | H | H | H | —C$_2$H$_5$ |
| VI-58 | H | H | H | -nC$_3$H$_7$ |
| VI-59 | H | H | H | -tertC$_4$H$_9$ |
| VI-60 | H | H | H | —CH$_2$—C$_6$H$_5$ |
| VI-61 | H | H | H | —C$_6$H$_5$ |
| VI-62 | H | H | H | —CH$_2$—COOCH$_3$ |
| VI-63 | H | H | H | —CH$_2$—COOC$_2$H$_5$ |
| VI-64 | H | H | H | —CF$_2$—COOCH$_3$ |
| VI-65 | H | H | H | —CF$_2$—COOC$_2$H$_5$ |
| VI-66 | H | H | H | —CH$_2$—CONH$_2$ |
| VI-67 | H | H | H | —CH$_2$—CONHCH$_3$ |
| VI-68 | H | H | H | —CH$_2$—CON(CH$_3$)$_2$ |
| VI-69 | H | H | H | —CH$_2$—CONH—CH$_2$—C$_6$H$_5$ |
| VI-70 | H | H | H | —CH$_2$—CONH—C$_6$H$_5$ |
| VI-71 | H | H | H | —CH$_2$—CONH(CH$_2$—C$_6$H$_5$)$_2$ |
| VI-72 | H | H | H | —CH$_2$—CON(—CH$_2$—CH$_2$—CH$_2$—CH$_2$—) |

TABLE 6-continued

A is Me₂Val, B is Val, D is MeVal, E is Pro and F is of Formula II_f, the substituent -(C≡C)-G is in position 4 relative to the nitrogen G is of Formula V_g, VI_g, VII_g, VIII_g or IX_g.

| No. | RF | R¹F | R²F | -G |
|---|---|---|---|---|
| VI-73 | H | H | H | —CH₂—CON(—CH₂—CH₂—CH₂—CH₂—CH₂) |
| VI-74 | H | H | H | —CH₂—CH₂—COOCH₃ |
| VI-75 | H | H | H | —CH₂—CH₂—COOC₂H₅ |
| VI-76 | H | H | H | —CH₂—CH₂—CONH₂ |
| VI-77 | H | H | H | —CH₂—CH₂—CONHCH₃ |
| VI-78 | H | H | H | —CH₂—CH₂—CON(CH₃)₂ |
| VI-79 | H | H | H | —CH₂—CH₂—CONH—CH₂—C₆H₅ |
| VI-80 | H | H | H | —CH₂—CH₂—CONH—C₆H₅ |
| VI-81 | H | H | H | —CH₂—CH₂—CONH(CH₂—C₆H₅)₂ |
| VI-82 | H | H | H | —CH₂—CH₂—CON(—CH₂—CH₂—CH₂—CH₂—) |
| VI-83 | H | H | H | —CH₂—CH₂—CON(—CH₂—(CH₂)₃—CH₂) |
| VI-84 | H | H | H | —CH₂—COOH₃ |
| VI-85 | H | H | H | —CH₂—CH₂—COCH₃ |
| VI-86 | H | H | H | —CH₂—COC₂H₅ |
| VI-87 | H | H | H | —CH₂—CH₂—COC₂H₅ |
| VI-88 | H | H | H | —CH₂—CO—C₆H₅ |
| VI-89 | H | H | H | —CH₂—CH₂—CO—C₆H₅ |
| VI-90 | H | H | H | —CH₂—CO—CH₂—C₆H₅ |
| VI-91 | H | H | H | —CH₂—CH₂—CO—CH₂—C₆H₅ |
| VI-92 | H | H | H | —CH₂—SOC₆H₅ |
| VI-93 | H | H | H | —CH₂—SOCH₃ |
| VI-94 | H | H | H | —CH₂—SO(4-CH₃—C₆H₄) |
| VI-95 | H | H | H | —CH₂—SO₂OH₅ |
| VI-96 | H | H | H | —CH₂—SO₂CH₃ |
| VI-97 | H | H | H | —CH₂—SO(4-CH₃—C₆H₄) |
| VI-98 | H | H | H | —CH₂—CH₂—SOC₆H₅ |
| VI-99 | H | H | H | —CH₂—CH₂—SOCH₃ |
| VI-100 | H | H | H | —CH₂—CH₂—SO(4-CH₃—C₆H₄) |
| VI-101 | H | H | H | —CH₂—CH₂—SO₂C₆H₅ |
| VI-102 | H | H | H | —CH₂—CH₂—SO₂CH₃ |
| VI-103 | H | H | H | —CH₂—CH₂—SO₂(4-CH₃—C₆H₄) |
| VI-104 | CH₃ | H | H | —CH₃ |
| VI-105 | CH₃ | H | H | —C₂H₅ |
| VI-106 | CH₃ | H | H | -nC₃H₇ |
| VI-107 | CH₃ | H | H | -isoC₃H₇ |
| VI-108 | CH₃ | H | H | -nC₄H₉ |
| VI-109 | CH₃ | H | H | -tertC₄H₉ |
| VI-110 | CH₃ | H | H | -cycloC₃H₅ |
| VI-111 | CH₃ | H | H | -cycloC₄H₇ |
| VI-112 | CH₃ | H | H | -cycloC₅H₉ |
| VI-113 | CH₃ | H | H | -ayaloC₆H₁₁ |
| VI-114 | CH₃ | H | H | -cycloC₇H₁₂ |
| VI-115 | CH₃ | H | H | —CH₂—O—CH₃ |
| VI-116 | CH₃ | H | H | —CH₂—CH₂—O—CH₃ |
| VI-117 | CH₃ | H | H | —CH₂—C₆H₅ |
| VI-118 | CH₃ | H | H | —C₆H₅ |
| VI-119 | CH₃ | H | H | -(4-HO—C₆H₅) |
| VI-120 | CH₃ | H | H | -(2-CF₃—C₆H₄) |
| VI-121 | CH₃ | H | H | -(3-CF₃—C₆H₄) |
| VI-122 | CH₃ | H | H | -(4-CF₃—C₆H₄) |
| VI-123 | CH₃ | H | H | -(2-OCH₃—C₆H₄) |
| VI-124 | CH₃ | H | H | -(3-OCH₃—C₆H₄) |
| VI-125 | CH₃ | H | H | -(4-OCH₃—C₆H₄) |
| VI-126 | CH₃ | H | H | -(2-SCH₃—C₆H₄) |
| VI-127 | CH₃ | H | H | -(3-SCH₃—C₆H₄) |
| VI-128 | CH₃ | H | H | -(4-SCH₃—C₆H₄) |
| VI-129 | CH₃ | H | H | -(2-N(CH₃)₂—C₆H₄) |
| VI-130 | CH₃ | H | H | -(3-N(CH₃)₂—C₆H₄) |
| VI-131 | CH₃ | H | H | -(4-N(CH₃)₂—C₆H₄) |
| VI-132 | CH₃ | H | H | -(4-CN—C₆H₄) |
| VI-133 | CH₃ | H | H | -(4-Cl—C₆H₄) |
| VI-134 | CH₃ | H | H | -(4-Br—C₆H₄] |
| VI-135 | CH₃ | H | H | -(4-F—C₆H₄] |
| VI-136 | CH₃ | H | H | -(4-CH₃—C₆H₄) |
| VI-137 | CH₃ | H | H | -(2-NO₂—C₆H₄) |
| VI-138 | CH₃ | H | H | -(3-NO₂—C₆H₄) |
| VI-139 | CH₃ | H | H | -(4-NO₂—C₆H₄] |
| VI-140 | CH₃ | H | H | -(2,4-OCH₃—C₆H₃) |
| VI-141 | CH₃ | H | H | -(3,4-OCH₃—C₆H₃) |
| VI-142 | CH₃ | H | H | -(3,4,5-OCH₃—C₆H₂) |
| VI-143 | CH₃ | H | H | -(3,4-CH₂OCH₂—C₆H₃) |
| VI-144 | CH₃ | H | H | -(2,3-CH₂OCH₂—C₆H₃) |

TABLE 6-continued

A is Me$_2$Val, B is Val, D is MeVal, E is Pro and F is of Formula II$_f$, the substituent -(C≡C)-G is in position 4 relative to the nitrogen G is of Formula V$_g$, VI$_g$, VII$_g$, VIII$_g$ or IX$_g$.

| No. | RF | R$^1$F | R$^2$F | -G |
|---|---|---|---|---|
| VI-145 | CH$_3$ | H | H | -2-pyridinyl |
| VI-146 | CH$_3$ | H | H | -2-furanyl |
| VI-147 | CH$_3$ | H | H | -2-thienyl |
| VI-148 | CH$_3$ | H | H | -3-pyridinyl |
| VI-149 | CH$_3$ | H | H | -3-furanyl |
| VI-150 | CH$_3$ | H | H | -3-thienyl |
| VI-151 | CH$_3$ | H | H | -4-pyridinyl |
| VI-152 | CH$_3$ | H | H | -2-thiazolyl |
| VI-153 | CH$_3$ | H | H | -2-axazolyl |
| VI-154 | CH$_3$ | H | H | -3-isoxazolyl |
| VI-155 | CH$_3$ | H | H | -4-isoxazolyl |
| VI-156 | CH$_3$ | H | H | -5-isoxazolyl |
| VI-157 | CH$_3$ | H | H | —CF$_3$ |
| VI-158 | CH$_3$ | H | H | —C$_2$F$_5$ |
| VI-159 | CH$_3$ | H | H | —CH$_3$ |
| VI-160 | CH$_3$ | H | H | —C$_2$H$_5$ |
| VI-161 | CH$_3$ | H | H | -nC$_3$H$_7$ |
| VI-162 | CH$_3$ | H | H | -tertC$_4$H$_9$ |
| VI-163 | CH$_3$ | H | H | —CH$_2$—C$_6$H$_5$ |
| VI-164 | CH$_3$ | H | H | —C$_6$H$_5$ |
| VI-165 | CH$_3$ | H | H | —CH$_2$—COOCH$_3$ |
| VI-166 | CH$_3$ | H | H | —CH$_2$—COOC$_2$H$_5$ |
| VI-167 | CH$_3$ | H | H | —CF$_2$—COOCH$_3$ |
| VI-168 | CH$_3$ | H | H | —CF$_2$—COOC$_2$H$_5$ |
| VI-169 | CH$_3$ | H | H | —CH$_2$—CONH$_2$ |
| VI-170 | CH$_3$ | H | H | —CH$_2$—CONHCH$_3$ |
| VI-171 | CH$_3$ | H | H | —CH$_2$—CON(CH$_3$)$_2$ |
| VI-172 | CH$_3$ | H | H | —CH$_2$—CONH—CH$_2$—C$_6$H$_5$ |
| VI-173 | CH$_3$ | H | H | —CH$_2$—CONH—C$_6$H$_5$ |
| VI-174 | CH$_3$ | H | H | —CH$_2$—CONH(CH$_2$—C$_6$H$_3$)$_2$ |
| VI-175 | CH$_3$ | H | H | —CH$_2$—CON(—CH$_2$—CH$_2$—CH$_2$—CH$_2$—) |
| VI-176 | CH$_3$ | H | H | —CH$_2$—CON(—CH$_2$—CH$_2$—CH$_2$—CH$_2$—CH$_2$) |
| VI-177 | CH$_3$ | H | H | —CH$_2$—CH$_2$—COOCH$_3$ |
| VI-178 | CH$_3$ | H | H | —CH$_2$—CH$_2$—COOC$_2$H$_5$ |
| VI-179 | CH$_3$ | H | H | —CH$_2$—CH$_2$—CONH$_2$ |
| VI-180 | CH$_3$ | H | H | —CH$_2$—CH$_2$—CONHCH$_3$ |
| VI-181 | CH$_3$ | H | H | —CH$_2$—CH$_2$—CON(CH$_3$)$_2$ |
| VI-182 | CH$_3$ | H | H | —CH$_2$—CH$_2$—CONH—CH$_2$—C$_6$H$_5$ |
| VI-183 | CH$_3$ | H | H | —CH$_2$—CH$_2$—CONH—C$_6$H$_5$ |
| VI-184 | CH$_3$ | H | H | —CH$_2$—CH$_2$—CONH(CH$_2$—C$_6$H$_5$)$_2$ |
| VI-185 | CH$_3$ | H | H | —CH$_2$—CH$_2$—CON(—CH$_2$—CH$_2$—CH$_2$—CH$_2$—) |
| VI-186 | CH$_3$ | H | H | —CH$_2$—CH$_2$—CON(—CH$_2$—(CH$_2$)$_3$—CH$_2$) |
| VI-187 | CH$_3$ | H | H | —CH$_2$—COCH$_3$ |
| VI-188 | CH$_3$ | H | H | —CH$_2$—CH$_2$—COCH$_3$ |
| VI-189 | CH$_3$ | H | H | —CH$_2$—COC$_2$H$_5$ |
| VI-190 | CH$_3$ | H | H | —CH$_2$—CH$_2$—COC$_2$H$_5$ |
| VI-191 | CH$_3$ | H | H | —CH$_2$—CO—C$_6$H$_5$ |
| VI-192 | CH$_3$ | H | H | —CH$_2$—CH$_2$—CO—C$_6$H$_5$ |
| VI-193 | CH$_3$ | H | H | —CH$_2$—CO—CH$_2$—C$_6$H$_5$ |
| VI-194 | CH$_3$ | H | H | —CH$_2$—CH$_2$—CO—CH$_2$—C$_6$H$_5$ |
| VI-195 | CH$_3$ | H | H | —CH$_2$—SOC$_6$H$_5$ |
| VI-196 | CH$_3$ | H | H | —CH$_2$—SOCH$_3$ |
| VI-197 | CH$_3$ | H | H | —CH$_2$—SO(4-CH$_3$—C$_6$H$_4$) |
| VI-198 | CH$_2$ | H | H | —CH$_2$—SO$_2$C$_6$H$_5$ |
| VI-199 | CH$_3$ | H | H | —CH$_2$—SO$_2$CH$_3$ |
| VI-200 | CH$_3$ | H | H | —CH$_2$—SO$_2$(4-CH$_3$—C$_6$H$_4$) |
| VI-201 | CH$_3$ | H | H | —CH$_2$—CH$_2$—SOC$_6$H$_5$ |
| VI-202 | CH$_3$ | H | H | —CH$_2$—CH$_2$—SOCH$_3$ |
| VI-203 | CH$_3$ | H | H | —CH$_2$—CH$_2$—SO(4-CH$_3$—C$_6$H$_4$) |
| VI-204 | CH$_3$ | H | H | —CH$_2$—CH$_2$—SO$_2$C$_6$H$_5$ |
| VI-205 | CH$_3$ | H | H | —CH$_2$—CH$_2$—SO$_2$CH$_3$ |
| VI-206 | CH$_3$ | H | H | —CH$_2$—CH$_2$—SO$_2$(4-CH$_3$—C$_6$H$_4$) |

TABLE 7

A is Me₂Val, B is Val, D is MeVal, E is Pro and F is of Formula III$_f$, the substituent -(C=O)-G is in position 2 relative to the nitrogen and a$_f$ is 1 G is of Formula II$_g$ or III$_g$ The compounds are mixtures of diasteromers, configuration in F is R, S (cis) or S,R (cis)

| No. | Rf | -G |
|---|---|---|
| VII-1 | H | —NH—CH$_3$ |
| VII-2 | H | —NH—CH$_2$—C$_6$H$_5$ |
| VII-3 | H | —NH-isoC$_3$H$_7$ |
| VII-4 | H | —NH—C$_6$H$_5$ |
| VII-5 | H | 1,3-Thiazol-2-yl-amide |
| VII-6 | H | —NH—CH$_3$ |
| VII-7 | H | —NH—CH$_3$ |
| VII-8 | H | —NH—C$_2$H$_5$ |
| VII-9 | H | —NH-nC$_3$H$_7$ |
| VII-10 | H | —NH-nC$_4$H$_9$ |
| VII-11 | H | —NH-tertC$_4$H$_9$ |
| VII-12 | H | —NH-cycloC$_3$H$_5$ |
| VII-13 | H | —NH-cycloC$_4$H$_7$ |
| VII-14 | H | —NH-cycloC$_5$H$_9$ |
| VII-15 | H | —NH-cycloC$_6$H$_{11}$ |
| VII-16 | H | —NH-cycloC$_7$H$_{12}$ |
| VII-17 | H | —NH—CH$_2$—O—CH$_3$ |
| VII-18 | H | —NH—CH$_2$—CH$_2$—O—CH$_3$ |
| VII-19 | H | —NH-1-adamantyl |
| VII-20 | H | —NH—(4-HO—C$_6$H$_5$) |
| VII-21 | H | —NH—(2-CF$_3$—C$_6$H$_4$) |
| VII-22 | H | —NH—(3-CF$_3$—C$_6$H$_4$) |
| VII-23 | H | —NH—(4-CF$_3$—C$_6$H$_4$) |
| VII-24 | H | —NH—(2-OCH$_3$—C$_6$H$_4$) |
| VII-25 | H | —NH—(3-OCH$_3$—C$_6$H$_4$) |
| VII-26 | H | —NH—(4-OCH$_3$—C$_6$H$_4$) |
| VII-27 | H | —NH—(2-SCH$_3$—C$_6$H$_4$) |
| VII-28 | H | —NH—(3-SCH$_3$—C$_6$H$_4$) |
| VII-29 | H | —NH—(4-SCH$_3$—C$_6$H$_4$) |
| VII-30 | H | —NH—(2-N(CH$_3$)$_2$—C$_6$H$_4$) |
| VII-31 | H | —NH—(3-N(CH$_3$)$_2$—C$_6$H$_4$) |
| VII-32 | H | —NH—(4-N(CH$_3$)$_2$—C$_6$H$_4$) |
| VII-33 | H | —NH—(4-CN—C$_6$H$_4$) |
| VII-34 | H | —NH—(4-Cl—C$_6$H$_4$) |
| VII-35 | H | —NH—(4-Br—C$_6$H$_4$] |
| VII-36 | H | —NH—(4-F—C$_6$H$_4$] |
| VII-37 | H | —NH—(4-CH$_3$—C$_6$H$_4$) |
| VII-38 | H | —NH—(2-NO$_2$—C$_6$H$_4$) |
| VII-39 | H | —NH—(3-NO$_2$—C$_6$H$_4$) |
| VII-40 | H | —NH—(4-NO$_2$—C$_6$H$_4$] |
| VII-41 | H | —NH—(2,4-OCH$_3$—C$_6$H$_3$) |
| VII-42 | H | —NH—(3,4-OCH$_3$—C$_6$H$_3$) |
| VII-43 | H | —NH—(3,4,5-OCH$_3$—C$_6$H$_2$) |
| VII-44 | H | —NH—(3,4-CH$_2$OCH$_2$—C$_6$H$_3$) |
| VII-45 | H | —NH—(2,3-CH$_2$OCH$_2$—C$_6$H$_3$) |
| VII-46 | H | —NH-2-pyridinyl |
| VII-47 | H | —NH-2-furanyl |
| VII-48 | H | —NH-2-thienyl |
| VII-49 | H | —NH-3-pyridinyl |
| VII-50 | H | —NH-3-furanyl |
| VII-51 | H | —NH-3-thienyl |
| VII-52 | H | —NH-4-pyridinyl |
| VII-53 | H | —NH-2-oxazolyl |
| VII-54 | H | —NH-3-isoxazolyl |
| VII-55 | H | —NH-4-isoxazolyl |
| VII-56 | H | —NH-5-isoxazolyl |
| VII-57 | H | —NH-2R-(but-2-yl) |
| VII-58 | H | —NH-2S-(but-2-yl) |
| VII-59 | H | —NH—O—CH$_3$ |
| VII-60 | H | —N(CH$_3$)(OCH$_3$) |
| VII-61 | H | —N(-(CH$_2$)$_3$—O—) |
| VII-62 | H | —NH—O—CH$_2$—C$_6$H$_5$ |
| VII-63 | H | —N(CH$_3$)(O—CH$_2$—C$_6$H$_5$) |
| VII-64 | H | —N(-(CH$_2$)$_2$—CH(C$_6$H$_5$)—O—) |
| VII-65 | H | —NH—O—C$_2$H$_5$ |
| VII-66 | H | —N(C$_2$H$_5$)(OC$_2$H$_5$) |
| VII-67 | H | —N(CH$_3$)(OC$_2$H$_5$) |
| VII-68 | H | —NH—O-isoC$_3$H$_7$ |
| VII-69 | H | —N(CH$_3$)(O-isoC$_3$H$_7$) |
| VII-70 | H | —NH—O-nC$_3$H$_7$ |
| VII-71 | H | —N(CH$_3$)(O-nC$_3$H$_7$) |
| VII-72 | H | —NH—O-nC$_4$H$_9$ |
| VII-73 | H | —N(CH$_3$)(O-nC$_4$H$_9$) |
| VII-74 | H | —NH—O-tertC$_4$H$_9$ |
| VII-75 | H | —N(CH$_3$)(O-tertC$_4$H$_9$) |
| VII-76 | H | —NH—O—C$_6$H$_5$ |
| VII-77 | H | —N(CH$_3$)(O—C$_6$H$_5$) |
| VII-78 | H | —N(CH$_3$)$_2$ |
| VII-79 | H | —N(CH$_2$—C$_6$H$_5$)$_2$ |
| VII-80 | H | —N(C$_2$H$_5$)$_2$ |
| VII-81 | H | —N(isoC$_3$H$_7$)$_2$ |
| VII-82 | H | —N(nC$_3$H$_7$)$_2$ |
| VII-83 | H | —N(nC$_4$H$_9$)$_2$ |
| VII-84 | H | —N(C$_6$H$_5$)$_2$ |
| VII-85 | H | —NH—CH$_2$—CH$_2$—OH |
| VII-86 | H | —NH-(CH$_2$)$_3$—OH |
| VII-87 | H | —NH(-(CH$_2$)$_2$—CH(C$_6$H$_5$)—OH) |
| VII-88 | H | —NH-(CH$_2$)$_4$—OH |
| VII-89 | H | —NH(—CH(CH$_3$)—CH$_2$—OH) |
| VII-90 | H | —NH(—CH$_2$—CH(CH$_3$)—OH) |
| VII-91 | H | —NH(—CH(CH$_3$)—(CH$_2$)$_2$—OH) |
| VII-92 | H | —NH(-(CH$_2$)$_2$—CH(CH$_3$)—OH) |
| VII-93 | CH$_3$ | —NH—CH$_3$ |
| VII-94 | CH$_3$ | —NH—CH$_2$C$_6$H$_5$ |
| VII-95 | CH$_3$ | —NH-isoC$_3$H$_7$ |
| VII-96 | CH$_3$ | —NH—C$_6$H$_5$ |
| VII-97 | CH$_3$ | —NH—C$_2$H$_5$ |
| VII-98 | CH$_3$ | —NH-nC$_3$H$_7$ |
| VII-99 | CH$_3$ | —NH-nC$_4$H$_9$ |
| VII-100 | CH$_3$ | —NH-tertC$_4$H$_9$ |
| VII-101 | CH$_3$ | —NH-cycloC$_3$H$_5$ |
| VII-102 | CH$_3$ | —NH-cycloC$_4$H$_7$ |
| VII-103 | CH$_3$ | —NH-cycloC$_5$H$_9$ |
| VII-104 | CH$_3$ | —NH-cycloC$_6$H$_{11}$ |
| VII-105 | CH$_3$ | —NH-1-adamantyl |
| VII-106 | CH$_3$ | —NH-2R-(but-2-yl) |
| VII-107 | CH$_3$ | —NH-2S-(but-2-yl) |
| VII-108 | CH$_3$ | —NH—O—CH$_3$ |
| VII-109 | CH$_3$ | —N(CH$_3$)(OCH$_3$) |
| VII-110 | CH$_3$ | —N(-(CH$_2$)$_3$—O—) |
| VII-111 | CH$_3$ | —N(CH$_3$)$_2$ |
| VII-112 | CH$_3$ | —N(CH$_2$—C$_6$H$_5$)$_2$ |
| VII-113 | CH$_3$ | —N(C$_2$H$_5$)$_2$ |
| VII-114 | CH$_3$ | —N(isoC$_3$H$_7$)$_2$ |
| VII-115 | CH$_3$ | —N(nC$_3$H$_7$)$_2$ |
| VII-116 | CH$_3$ | —N(nC$_4$H$_9$)$_2$ |
| VII-117 | CH$_3$ | —N(C$_6$H$_5$)$_2$ |

TABLE 8

A is Me$_2$Val, B is Val, D is MeVal, E is Pro and F is of Formula III$_f$, the substituent -(C=O)-G is in position 2 relative to the nitrogen and a$_f$ is 1 G is of Formula II$_g$ or III$_g$ The compounds are mixtures of diasteromers, configuration in F is R, R (trans) or S,S (trans)

| No. | Rf | -G |
|---|---|---|
| VIII-1 | H | —NH—CH$_3$ |
| VIII-2 | H | —NH—CH$_2$—C$_6$H$_5$ |
| VIII-3 | H | —NH-isoC$_3$H$_7$ |
| VIII-4 | H | —NH—C$_6$H$_5$ |
| VIII-5 | H | 1,3-Thiazol-2-yl-amide |
| VIII-6 | H | —NH—CH$_3$ |
| VIII-7 | H | —NH—CH$_3$ |
| VIII-8 | H | —NH—C$_2$H$_5$ |
| VIII-9 | H | —NH-nC$_3$H$_7$ |
| VIII-10 | H | —NH-nC$_4$H$_5$ |
| VIII-11 | H | —NH-tertC$_4$H$_9$ |

TABLE 8-continued

A is Me$_2$Val, B is Val, D is MeVal, E is Pro and F is of Formula III$_f$, the substituent -(C=O)-G is in position 2 relative to the nitrogen and a$_f$ is 1 G is of Formula II$_g$ or III$_g$ The compounds are mixtures of diasteromers, configuration in F is R, R (trans) or S,S (trans)

| No. | Rf | -G |
|---|---|---|
| VIII-12 | H | —NH-cycloC$_3$H$_5$ |
| VIII-13 | H | —NH-cycloC$_4$H$_7$ |
| VIII-14 | H | —NH-cycloC$_5$H$_9$ |
| VIII-15 | H | —NH-cycloC$_6$H$_{11}$ |
| VIII-16 | H | —NH-cycloC$_7$H$_{12}$ |
| VIII-17 | H | —NH—CH$_2$—O—CH$_3$ |
| VIII-18 | H | —NH—CH$_2$—CH$_2$—O—CH$_3$ |
| VIII-19 | H | —NH-1-adamantyl |
| VIII-20 | H | —NH-(4-HO—C$_6$H$_5$) |
| VIII-21 | H | —NH-(2-CF$_3$—C$_6$H$_4$) |
| VIII-22 | H | —NH-(3-CF$_3$—C$_6$H$_4$) |
| VIII-23 | H | —NH-(4-CF$_3$—C$_6$H$_4$) |
| VIII-24 | H | —NH-(2-OCH$_3$—C$_6$H$_4$) |
| VIII-25 | H | —NH-(3-OCH$_3$—C$_6$H$_4$) |
| VIII-26 | H | —NH-(4-OCH$_3$—C$_6$H$_4$) |
| VIII-27 | H | —NH-(2-SCH$_3$—C$_6$H$_4$) |
| VIII-28 | H | —NH-(3-SCH$_3$—C$_6$H$_4$) |
| VIII-29 | H | —NH-(4-SCH$_3$—C$_6$H$_4$) |
| VIII-30 | H | —NH-(2-N(CH$_3$)$_2$—C$_6$H$_4$) |
| VIII-31 | H | —NH-(3-N(CH$_3$)$_2$—C$_6$H$_4$) |
| VIII-32 | H | —NH-(4-N(CH$_3$)$_2$—C$_6$H$_4$) |
| VIII-33 | H | —NH-(4-CN—C$_6$H$_4$) |
| VIII-34 | H | —NH-(4-Cl—C$_6$H$_4$) |
| VIII-35 | H | —NH-(4-Br—C$_6$H$_4$] |
| VIII-36 | H | —NH-(4-F—C$_6$H$_4$] |
| VIII-37 | H | —NH-(4-CH$_3$—C$_6$H$_4$) |
| VIII-38 | H | —NH-(2-NO$_2$—C$_6$H$_4$) |
| VIII-39 | H | —NH-(3-NO$_2$—C$_6$H$_4$) |
| VIII-40 | H | —NH-(4-NO$_2$—C$_6$H$_4$] |
| VIII-41 | H | —NH-(2,4-OCH$_3$—C$_6$H$_3$) |
| VIII-42 | H | —NH-(3,4-OCH$_3$—C$_6$H$_3$) |
| VIII-43 | H | —NH-(3,4,5-OCH$_3$—C$_6$H$_2$) |
| VIII-44 | H | —NH-(3,4-CH$_2$OCH$_2$—C$_6$H$_3$) |
| VIII-45 | H | —NH-(2,3-CH$_2$OCH$_2$—C$_6$H$_3$) |
| VIII-46 | H | —NH-2-pyridinyl |
| VIII-47 | H | —NH-2-furanyl |
| VIII-48 | H | —NH-2-thienyl |
| VIII-49 | H | —NH-3-pyridinyl |
| VIII-50 | H | —NH-3-furanyl |
| VIII-51 | H | —NH-3-thienyl |
| VIII-52 | H | —NH-4-pyridinyl |
| VIII-53 | H | —NH-2-oxazolyl |
| VIII-54 | H | —NH-3-isoxazolyl |
| VIII-55 | H | —NH-4-isoxazolyl |
| VIII-56 | H | —NH-5-isoxazolyl |
| VIII-57 | H | —NH-2R-(but-2-yl) |
| VIII-58 | H | —NH-2S-(but-2-yl) |
| VIII-59 | H | —NH—O—CH$_3$ |
| VIII-60 | H | —N(CH$_3$)(OCH$_3$) |
| VIII-61 | H | —N(-(CH$_2$)$_3$—O—) |
| VIII-62 | H | —NH—O—CH$_2$—C$_6$H$_5$ |
| VIII-63 | H | —N(CH$_3$)(O—CH$_2$—C$_6$H$_5$) |
| VIII-64 | H | —N(-(CH$_2$)$_2$—CH(C$_6$H$_5$)—O—) |
| VIII-65 | H | —NH—O—C$_2$H$_5$ |
| VIII-66 | H | —N(C$_2$H$_5$)(OC$_2$H$_5$) |
| VIII-67 | H | —N(CH$_3$)(OC$_2$H$_5$) |
| VIII-68 | H | —NH—O-isoC$_3$H$_7$ |
| VIII-69 | H | —N(CH$_3$)(O-isoC$_3$H$_7$) |
| VIII-70 | H | —NH—O-nC$_3$H$_7$ |
| VIII-71 | H | —N(CH$_3$)(O-nC$_3$H$_7$) |
| VIII-72 | H | —NH—O-nC$_4$H$_9$ |
| VIII-73 | H | —N(CH$_3$)(O-nC$_4$H$_9$) |
| VIII-74 | H | —NH—O-tertC$_4$H$_9$ |
| VIII-75 | H | —N(CH$_3$)(O-tertC$_4$H$_9$) |
| VIII-76 | H | —NH—O—C$_6$H$_5$ |
| VIII-77 | H | —N(CH$_3$)(O—C$_6$H$_5$) |
| VIII-78 | H | —N(CH$_3$)$_2$ |
| VIII-79 | H | —N(CH$_2$—C$_6$H$_5$)$_2$ |
| VIII-80 | H | —N(C$_2$H$_5$)$_2$ |
| VIII-81 | H | —N(isoC$_3$H$_7$)$_2$ |
| VIII-82 | H | —N(nC$_3$H$_7$)$_2$ |
| VIII-83 | H | —N(nC$_4$H$_9$)$_2$ |
| VIII-84 | H | —N(C$_6$H$_5$)$_2$ |
| VIII-85 | H | —NH—CH$_2$—CH$_2$—OH |
| VIII-86 | H | —NH-(CH$_2$)$_3$—OH |
| VIII-87 | H | —NH(-(CH$_2$)$_2$—CH(C$_6$H$_5$)—OH) |
| VIII-88 | H | —NH-(CH$_2$)$_4$—OH |
| VIII-89 | H | —NH(—CH(CH$_3$)—CH$_2$—OH) |
| VIII-90 | H | —NH(—CH$_2$—CH(CH$_3$)—OH) |
| VIII-91 | H | —NH(—CH(CH$_3$)-(CH$_2$)$_2$—OH) |
| VIII-92 | H | —NH(-(CH$_2$)$_2$—CH(CH$_3$)—OH) |
| VIII-93 | CH$_3$ | —NH—CH$_3$ |
| VIII-94 | CH$_3$ | —NH—CH$_2$—C$_6$H$_5$ |
| VIII-95 | CH$_3$ | —NH-isoC$_3$H$_7$ |
| VIII-96 | CH$_3$ | —NH—C$_6$H$_5$ |
| VIII-97 | CH$_3$ | —NH—C$_2$H$_5$ |
| VIII-98 | CH$_3$ | —NH-nC$_3$H$_7$ |
| VIII-99 | CH$_3$ | —NH-nC$_4$H$_9$ |
| VIII-100 | CH$_3$ | —NH-tertC$_4$H$_9$ |
| VIII-101 | CH$_3$ | —NH-cycloC$_3$H$_5$ |
| VIII-102 | CH$_3$ | —NH-cycloC$_4$H$_7$ |
| VIII-103 | CH$_3$ | —NH-cycloC$_5$H$_9$ |
| VIII-104 | CH$_3$ | —NH-cycloC$_6$H$_{11}$ |
| VIII-105 | CH$_3$ | —NH-1-adamantyl |
| VIII-106 | CH$_3$ | —NH-2R-(but-2-yl) |
| VIII-107 | CH$_3$ | —NH-2S-(but-2-yl) |
| VIII-108 | CH$_3$ | —NH—O—CH$_3$ |
| VIII-109 | CH$_3$ | —N(CH$_3$)(OCH$_3$) |
| VIII-110 | CH$_3$ | —N(-(CH$_2$)$_3$—O—) |
| VIII-111 | CH$_3$ | —N(CH$_3$)$_2$ |
| VIII-112 | CH$_3$ | —N(CH$_2$—C$_6$H$_5$)$_2$ |
| VIII-113 | CH$_3$ | —N(C$_2$H$_5$)$_2$ |
| VIII-114 | CH$_3$ | —N(isoC$_3$H$_7$)$_2$ |
| VIII-115 | CH$_3$ | —N(nC$_3$H$_7$)$_2$ |
| VIII-116 | CH$_3$ | —N(nC$_4$H$_9$)$_2$ |
| VIII-117 | CH$_3$ | —N(C$_6$H$_5$)$_2$ |

Mass spectrometry data of selected examples:

I-1   2-(Me$_2$Val-Val-MeVal-Pro-NH)—C$_6$H$_4$C(O)NHCH$_3$
      FAB-MS: 588 (M + H$^+$)
I-2   2-(Me$_2$Val-Val-MeVal-Pro-NH)—C$_6$H$_4$C(O)NHCH$_2$C$_6$H$_5$
      FAB-MS: 664 (M + H$^+$)
I-3   2-(Me$_2$Val-Val-MeVal-Pro-NH)—C$_6$H$_4$C(O)NHCH(CH$_3$)$_2$
      FAB-MS: 616 (M + H$^+$)
I-4   2-(Me$_2$Val-Val-MeVal-Pro-NH)—C$_6$H$_4$C(O)NHC$_6$H$_5$
      FAB-MS: 650 (M + H$^+$)
I-5   2-(Me$_2$Val-Val-MeVal-Pro-NH)—C$_6$H$_4$C(O)NH(thiazol-2-yl)
      FAB-MS: 657 (M + H$^+$)
I-6   2-Me$_2$Val-Val-MeVal-ProNH)-4,5-
      bis(methoxy)C$_6$H$_2$C(O)NHCH$_3$
      FAB-MS: 649 (M + H$^+$)
I-7   2-(Me$_2$ValVal-MeVal-ProNH)-3-cyclopentanyl-C$_6$H$_3$C(O)NHCH$_3$
      FAB-MS: 656 (M + H$^+$)
I-64  2-(Me$_2$Val-Val-MeVal-Pro-NH)—
      C$_6$H$_4$—CO—N(—(CH$_2$)$_2$—CH(C$_6$H$_5$)O—)
      (mix. of diastereomers) FAB-MS: 706 (M + H$^+$)
I-79  2-(Me$_2$Val-Val-MeVal-Pro-NH)—C$_6$H$_4$—CO—N(CH$_2$C$_6$H$_5$)$_2$
      FAB-MS: 754 (M + H$^+$)
I-86  2-(Me$_2$Val-Val-MeVal-Pro-NH)—C$_6$H$_4$—CO—NH(—(CH$_2$)$_3$—OH)
      FAB-MS: 632 (M + H$^+$)
I-87  2-(Me$_2$Val-Val-MeVal-Pro-NH)—
      C$_6$H$_4$C(O)NH((CH$_2$)$_2$CH(C$_6$H$_5$)OH)
      FAB-MS: 708 (M + H$^+$)
I-143 2-(Me$_2$Val-Val-MeVal-Pro-N(CH$_3$))—C$_6$H$_4$—CONHCH$_3$
      FAB-MS: 601 (M + H$^+$)
II-1  3-(Me$_2$Val-Val-MeVal-Pro-NH)—C$_6$H$_4$—CO—NHCH$_3$
      FAB-MS: 588 (M + H$^+$)

-continued

Mass spectrometry data of selected examples:

II-2  3-(Me$_2$Val-Val-MeVal-Pro-NH)—C$_6$H$_4$—CO—NH CH$_2$C$_6$H$_5$
      FAB-MS: 664 (M + H$^+$)
IV-1  2-(Me$_2$Val-Val-MeVal-Pro-NH)—C$_6$H$_4$—CO—CH$_3$
      FAB-MS: 609 (M + H$^+$)
IV-15 2-(Me$_2$Val-Val-MeVal-Pro-NH)—C$_6$H$_4$—CO—C$_6$H$_5$
      FAB-MS: 635 (M + H$^+$)

Evaluation of Biological Activity

In vitro methodology

Cytotoxicity was measured using a standard methodology for adherent cell lines, such as the microculture tetrazolium assay (MTT). Details of this assay have been published (Alley, M. C. et al., Cancer Research 48:589–601, 1988). Exponentially growing cultures of tumor cells such as the HT-29 colon carcinoma or LX-1 lung tumor were used to make microtiter plate cultures. Cells were seeded at 5000–20,000 cells per well in 96-well plates (in 150 mL of media), and grown overnight at 37° C. Test compounds were added, in 10-fold dilutions varying from $10^{-4}$M to $10^{-10}$M. Cells were then incubated for 48 hours. To determine the number of viable cells in each well, the MTT dye was added (50 mL of a 3 mg/mL solution of 3-(4,5-dimethylthiazol-2-yl)-2,5-diphenyltetrazolium bromide in saline). This mixture was incubated at 37° C. for 5 hours, and then 50 mL of 25% SDS, pH 2, was added to each well. After an overnight incubation, the absorbance of each well at 550 nm was read using an ELISA reader. The values for the mean ±SD of data from replicated wells were calculated, using the formula % T/C (% viable cells treated/control). The concentration of test compound which gives a T/C of 50% growth inhibition was designated as the IC$_{50}$.

| Compound No. | IC$_{50}$ (mol/l) |
|---|---|
| I-1 | $4 \times 10^{-7}$ |
| I-2 | $>10^{-6}$ |
| I-3 | $5 \times 10^{-7}$ |
| I-4 | $4 \times 10^{-7}$ |
| I-5 | $1.5 \times 10^{-7}$ |
| I-6 | $2 \times 10^{-7}$ |
| I-7 | $4 \times 10^{-7}$ |
| I-60 | $4 \times 10^{-7}$ |
| I-64 | $2.5 \times 10^{-7}$ |
| I-86 | $6 \times 10^{-7}$ |
| I-87 | $2 \times 10^{-7}$ |
| II-1 | $>10^{-6}$ |
| II-2 | $>10^{-6}$ |
| IV-1 | $>10^{-6}$ |
| IV-15 | $7 \times 10^{-8}$ |
| VII-2 | $>10^{-6}$ |

In vivo methodology

Compounds of this invention may be further tested in any of the various preclinical assays for in vivo activity which are indicative of clinical utility. Such assays are conducted with nude mice into which tumor tissue, preferably of human origin, has been transplanted ("xenografted"), as is well known in this field. Test compounds are evaluated for their anti-tumor efficacy following administration to the xenograft-bearing mice.

More specifically, human tumors which have been grown in athymic nude mice are transplanted into new recipient animals, using tumor fragments which are about 50 mg in size. The day of transplantation is designated as day 0. Six to ten days later, the mice are treated with the test compounds given as an intravenous or intraperitoneal injection, in groups of 5–10 mice at each dose. Compounds are given daily for 5 days, 10 days or 15 days, at doses from 10–100 mg/kg body weight. Tumor diameters and body weights are measured twice weekly. Tumor masses are calculated using the diameters measured with Vernier calipers, and the formula:

$$(\text{length} \times \text{width}^2)/2 = \text{mg of tumor weight}$$

Mean tumor weights are calculated for each treatment group, and T/C values determined for each group relative to the untreated control tumors.

The novel compounds of the present invention show good in vitro activity in the above-mentioned assay system.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A compound of the formula

or a salt thereof with a pharmaceutically acceptable acid, wherein

A is a proline derivative of Formula II$_a$,

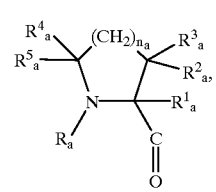

wherein n$_a$ is 0 to 3; R$_a$ is hydrogen, or unsubstituted or fluorine-substituted normal, branched or cyclic C$_1$–C$_3$-alkyl; R$^1_a$ is hydrogen, C$_1$–C$_3$-alkyl, phenyl, or substituted phenyl; or R$_a$ and R$^1_a$ together form a propylene bridge; and R$^2_a$, R$^3_a$, R$^4_a$ and R$^5_a$ are each, independently, hydrogen or alkyl; or an α-amino acid derivative of Formula III$_a$,

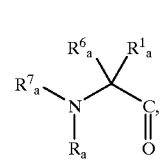

wherein R$_a$ is hydrogen or unsubstituted or fluorine-substituted C$_1$–C$_3$-alkyl; R$^1_a$ is hydrogen or C$_1$–C$_4$-alkyl; R$^6_a$ is alkyl, substituted alkyl, alkenyl, phenyl or substituted phenyl; or R$^1_a$ is an alkyl group and R$^6_a$ is C$_1$–C$_6$-alkyl, cycloalkylmethyl, benzyl or substituted benzyl; and R$^7_a$ is hydrogen or alkyl; or an α-amino acid derivative of Formula IV$_a$,

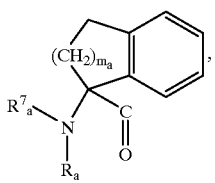

(IV$_a$)

wherein m$_a$ is 1 or 2; R$^7_a$ is hydrogen or alkyl; R$_a$ is hydrogen, or unsubstituted or fluorine-substituted alkyl; or an α-amino acid derivative of Formula V$_a$,

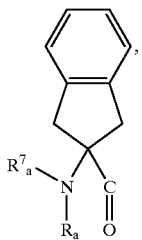

(V$_a$)

wherein R$^7_a$ is hydrogen or alkyl and R$_a$ is hydrogen, or unsubstituted or fluorine-substituted alkyl; or an α-amino acid of Formula VI$_a$,

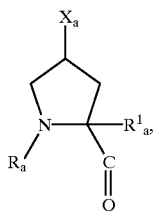

(VI$_a$)

wherein R$_a$ is hydrogen, or unsubstituted or fluorine-substituted alkyl; R$^1_a$ is hydrogen, alkyl, phenyl, or substituted phenyl; or R$_a$ and R$^1_a$ together form a propylene bridge; and X$_a$ is hydroxy, alkoxy or fluorine; or an α-amino acid of Formula VII$_a$,

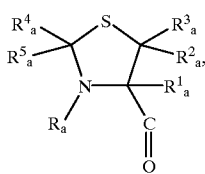

(VII$_a$)

wherein R$_a$ is hydrogen, or unsubstituted or fluorine-substituted alkyl; R$^1_a$ is hydrogen, alkyl, phenyl, or substituted phenyl; or R$_a$ and R$^1_a$ together form a propylene bridge; and R$^2_a$, R$^3_a$, R$^4_a$ and R$^5_a$ are each, independently, hydrogen or alkyl; or an α-amino acid residue of Formula VIII$_a$,

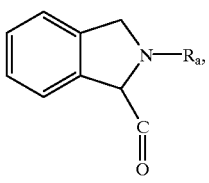

(VIII$_a$)

wherein R$_a$ is hydrogen, or unsubstituted or fluorine-substituted alkyl; or a 2-azabicyclo[2.2.1]heptane-3-carboxylic acid derivative of Formula IX$_a$,

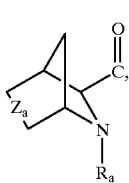

(IX$_a$)

wherein the 3-carbonyl moiety is in the endo or exo position, Z$_a$ is a single bond or a double bond, and R$_a$ is hydrogen or unsubstituted or fluorine-substituted alkyl; or an α-amino acid residue of Formula X$_a$,

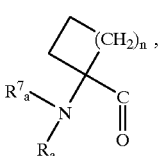

(X$_a$)

wherein n$_a$ is 1, 2 or 3, and R$^7_a$ is hydrogen or alkyl and R$_a$ is hydrogen, unsubstituted alkyl or fluorine-substituted alkyl;

B is a valyl, isoleucyl, allo-isoleucyl, norvalyl, 2-tert-butylglycyl or 2-ethylglycyl residue; or an α-amino acid residue of Formula II$_b$,

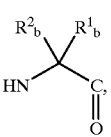

(II$_b$)

wherein R$^1_b$ is hydrogen, and R$^2_b$ is alkyl or alkenyl; or R$^1_b$ and R$^2_b$ together form an isopropylidene group;

D is an N-alkylvalyl, N-alkyl-2-ethylglycyl, N-alkyl-2-tert-butylglycyl, N-alkylnorleucyl, N-alkylisoleucyl, N-alkyl-allo-isoleucyl or N-alkylnorvalyl residue; or an α-amino acid residue of Formula II$_d$,

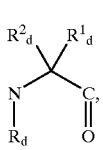
(II$_d$)

wherein R$_d$ is hydrogen, or unsubstituted or fluorine-substituted alkyl; R$^1{}_d$ is hydrogen; and R$^2$d is alkyl, substituted alkyl or alkenyl; or R$^1{}_d$ and R$^2{}_d$ together form an isopropylidene group; or an α-amino acid residue of Formula III$_d$,

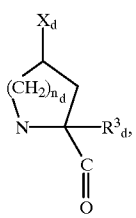
(III$_d$)

wherein n$_d$ is 1 or 2; R$^3{}_d$ is hydrogen, alkyl or fluorine-substituted alkyl; and X$_d$ is hydrogen; or n$_d$ is 1 and X$_d$ is fluorine, hydroxy, methoxy, or ethoxy;

E is a prolyl, thiazolidinyl-4-carbonyl, homoprolyl, or hydroxyprolyl residue; or an α-amino acid residue of Formula II$_e$,

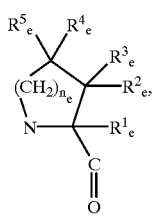
(II$_e$)

wherein n$_e$ is 0, 1 or 2, R$^1{}_e$ is hydrogen, or unsubstituted or fluorine-substituted alkyl; R$^2{}_e$ and R$^3{}_e$ are each, independently, hydrogen or alkyl; R$^4{}_e$ is hydrogen, hydroxy or alkoxy; and R$^5{}_e$ is hydrogen or fluorine; or n$_e$ is 1 and R$^3{}_e$ and R$^4{}_e$ together form a double bond; or n$_e$ is 1 and R$^4{}_e$ and R$^5{}_e$ together form a double-bonded oxygen diradical; or n$_e$ is 1 or 2 and R$^1{}_e$ and R$^2{}_e$ together form a double bond; or an aminocyclopentanecarboxylic acid residue of Formula III$_e$,

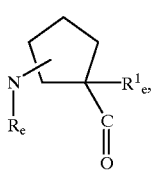
(III$_e$)

wherein R$_e$ is alkyl and R$^1{}_e$ is hydrogen, or unsubstituted or fluorine-substituted alkyl;

F is an aminobenzoyl derivative of Formula II$_f$,

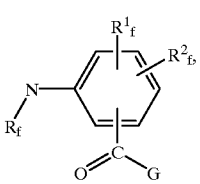
(II$_f$)

wherein R$_f$ is a hydrogen atom or an alkyl group; the carbonyl group is ortho, meta, or para to the nitrogen atom; R$^1{}_f$ and R$^2{}_f$ are each, independently, a hydrogen atom; a halogen atom; a C$_1$–C$_4$-alkyl group; a methoxy, ethoxy, trifluoromethyl, nitro, cyano, amino or dimethyalmino group; or R$^1{}_f$ and R$^2{}_f$ can together form a dioxymethylene group; or F is an aminocycloalkanecarboxylic acid residue of Formula III$_f$,

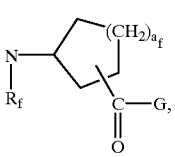
(III$_f$)

wherein R$_f$ is a hydrogen atom or an alkyl group; a$_f$ is 0, 1 or 2; and the carbonyl group is in position 2 or position 3 of the cycloalkane ring relative to the nitrogen atom; and G is a substituted or unsubstituted amino, hydrazido, aminoxy, oximato, arylalkyl, heteroarylalkyl, aryl, heteroaryl, alkoxycarbonylalkyl, aryloxycarbonylalkyl, alkoxycarbonyl, aryloxycarbonyl, aminocarbonylalkyl, aminocarbonyl, alkylcarbonylalkyl, alkylcarbonyl, arylcarbonylalkyl, arylcarbonyl, alkylsulfinylalkyl, alkylsulfinyl, arylsulfinylalkyl, arylsulfinyl, alkylsulfonylalkyl, alkylsulfonyl, arylsulfonylalkyl or arylsulfonyl group.

2. The compound of claim 1 wherein the pharmaceutically acceptable acid is hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid or acetylglycine.

3. The compound of claim 1 wherein G is a monovalent radical of Formula II$_g$,

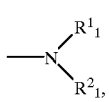
(II$_g$)

wherein
R$^1{}_l$ is a hydrogen atom, a normal or branched, saturated or unsaturated C$_1$–C$_{18}$-alkoxy group, a substituted or unsubstituted aryloxy group, a substituted or unsubstituted aryl-C$_1$–C$_6$-alkoxy group, a substituted or unsubstituted aryloxy-C$_1$–C$_6$-alkoxy group, wherein the aryl substituents comprise one or more halogen atoms or one or more C$_1$–C$_4$-alkyl, methoxy, ethoxy, trifluoromethyl, nitro or dioxymethylene groups; or a heteroaryl-$C_1$–$C_6$-alkoxy group, wherein the heteroaryl group is derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine; and $R^2_l$ is a hydrogen atom, a normal or branched $C_1$–$C_{18}$-alkyl group, a normal $C_1$–$C_{18}$ alkenyl group, a $C_3$–$C_{10}$-cycloalkyl group, an aryl group, or a substituted aryl group, wherein the aryl substituents comprise one or more halogen atoms, or one or more alkyl, alkoxy, dioxymethylene, trifluoromethyl or nitro groups; or a heteroaryl or substituted heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, isoindole, indazole, quinoline, pyridazine, pyrimidine, benzimidazole, benzopyran, benzothiazole, oxadiazole, thiadiazole or pyridine and the heteroaryl substituents comprise one or more $C_1$–$C_6$-alkyl, hydroxyl or phenyl groups; or a monovalent radical of Formula $II_l$,

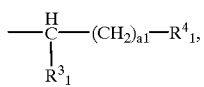

(II$_l$)

wherein $a_l$ is 0, 1, 2, 3, 4, or 5; $R^3_l$ is a methyl, ethyl, normal propyl or isopropyl group; $R^4_l$ is a saturated or partially unsaturated carbocyclic system which contains from 3 to 10 carbon atoms, an aryl group, or a substituted aryl group, wherein the aryl substituents comprise one or more halogen atoms or one or more alkoxy, dioxymethylene, trifluoromethyl, nitro, cyano, $C_1$–$C_7$-alkoxycarbonyl, $C_1$–$C_7$-alkylsulfonyl, amino, or $C_1$–$C_7$-dialkylamino groups; or a substituted or unsubstituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline, and the heteroaryl group substituents comprise one or more $C_1$–$C_6$-alkyl, hydroxyl or phenyl groups; or a monovalent radical of Formula $III_l$,

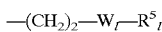

(III$_l$)

wherein $W_l$ is an $NR^6_l$ group, an oxygen atom or a sulfur atom, $R^5_l$ and $R^6_l$ are each, independently, a hydrogen atom or a $C_1$–$C_4$-alkyl, $C_3$–$C_7$-cycloalkyl, aryl, arylmethyl or substituted aryl or arylmethyl group, wherein the aryl substituents comprise one or more halogen atoms or one or more alkoxy, dioxymethylene, trifluoromethyl, nitro, cyano, $C_1$–$C_7$-alkoxycarbonyl, $C_1$–$C_7$-alkylsulfonyl, amino, or $C_1$–$C_7$-dialkylamino groups; or $R^6_l$ is a $C_1$–$C_{18}$-alkanoyl or benzoyl group; or a monovalent radical of Formula $IV_l$,

(IV$_l$), $b_l$ is 2, 3, or 4 and $Z_l$ is a formyl, aminocarbonyl, hydrazinocarbonyl, cyclic acetal, cyclic thioacetal, acyclic acetal or acyclic thioacetal group; or a monovalent radical of Formula $V_l$,

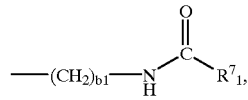

(V$_l$)

$b_l$ is 2, 3, or 4; $R^7_l$ is a polyglycol group of the formula —O—($CH_2$—$CH_2$—O)$_{d_l}$—$CH_3$; and $d_l$ is between about 2 and about 4, or between about 40 and about 90; or a monovalent radical of Formula $VI_l$,

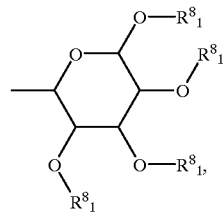

(VI$_l$)

wherein $R^8_l$ is a hydrogen atom, or a $C_1$–$C_4$ alkanoyl, $C_1$–$C_4$ alkyl, benzoyl, or benzyl group.

4. The compound of claim 1 wherein G is a β-hydroxy amino group of Formula $III_g$,

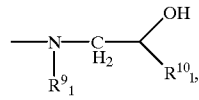

(III$_g$)

$R^9_l$ is a hydrogen atom, or a $C_1$–$C_6$-alkyl, aryl or substituted aryl group wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; and $R^{10}_l$ is a hydrogen atom, a methyl group or a phenyl group.

5. The compound of claim 1 wherein G is a hydrazido group of Formula $IV_g$,

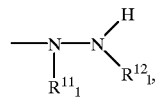

(IV$_g$)

wherein $R^{11}_l$ is a hydrogen atom and $R^{12}_l$ is a hydrogen atom, a normal or branched $C_1$–$C_8$-alkyl group, a $C_3$–$C_8$-cycloalkyl group, a $C_3$–$C_8$-cycloalkyl-$C_1$–$C_4$-alkyl group, an aryl-$C_1$–$C_4$-alkyl group, an aryl group, a substituted aryl group, wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl group, a heteroaryl-$C_1$–$C_4$-alkyl group or a substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups.

6. The compound of claim 1 wherein G is a monovalent radical of the formula —O—$R^{13}{}_l$, or of the formula —S—$R^{13}{}_l$, and $R^{13}{}_l$ is a $C_3$–$C_{10}$-cycloalkyl, straight-chain or branched $C_2$–$C_{16}$-alkenylmethyl, $C_1$–$C_{16}$-alkyl or halogen-substituted $C_1$–$C_{16}$-alkyl group; $R^{13}{}_l$ is a monovalent radical of the formula —$(CH_2)_{e_l}$—$R^{14}{}_l$, $e_l$ is 1, 2, or 3, and $R^{14}{}_l$ is a saturated or partially unsaturated $C_3$–$C_{10}$ carbocyclic group; $R^{13}{}_l$ is a monovalent radical of the formula —[$CH_2$—CH=C($CH_3$)—$CH_2$]$_{f_l}$—H, and $f_l$ is 1, 2, 3, or 4; $R^{13}{}_l$ is a monovalent radical of the formula —[$CH_2$—$CH_2$—O]$_{g_l}$—$CH_3$, and $g_l$ is between about 2 and about 4, or between about 40 and about 90; $R^{13}{}_l$ is a monovalent radical of the formula —$(CH_2)_{h_l}$—X, $h_l$ is 0, 1, 2, or 3; and X is an aryl or substituted aryl group wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups; $R^{13}{}_l$ is a monovalent radical of the formula —$(CH_2)_{b_l}$—$W_l$—$R^5{}_l$, $b_l$ is 2, 3, or 4, $W_l$ is an oxygen atom, a sulfur atom or an $NR^6{}_l$ group; $R^5{}_l$ is a saturated carbocyclic system which contains from about 3 to about 10 carbon atoms, a partially unsaturated carbocyclic system containing from about 3 to about 10 carbon atoms, an aryl or substituted aryl group wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups; and $R^6{}_l$ is a hydrogen atom, or a $C_1$–$C_4$ alkyl, $C_3$–$C_7$ cycloalkyl, $C_1$–$C_{18}$-alkanoyl, benzoyl, arylmethyl, aryl or substituted aryl or arylmethyl group, wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups.

7. The compound of claim 1 wherein G is an aminoxy group of the formula —O—N($R^{16}{}_l$)($R^{15}{}_l$), wherein $R^{15}{}_l$ and $R^{16}{}_l$ are each, independently, a hydrogen atom, a normal or branched $C_1$–$C_8$ alkyl group, a halogen-substituted normal or branched $C_1$–$C_8$-alkyl group, a $C_3$–$C_8$-cycloalkyl group, a $C_3$–$C_8$-cycloalkyl-$C_1$–$C_4$ alkyl group, an aryl-$C_1$–$C_4$-alkyl group, an aryl group or a substituted aryl-$C_1$–$C_4$-alkyl or aryl group, wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups; or $R^{15}{}_l$ and $R^{16}{}_l$ together with the nitrogen atom form a heterocyclic ring structure comprising 5, 6, or 7 atoms.

8. The compound of claim 1 wherein G is a oximato group of the formula —O—N=C($R^{15}{}_l$)($R^{16}{}_l$), wherein $R^{15}{}_l$ and $R^{16}{}_l$ are each, independently, a hydrogen atom, a normal or branched $C_1$–$C_8$ alkyl group, a halogen-substituted normal or branched $C_1$–$C_8$-alkyl group, a $C_3$–$C_8$-cycloalkyl group, a $C_3$–$C_8$-cycloalkyl-$C_1$–$C_4$ alkyl group, an aryl-$C_1$–$C_4$-alkyl group, an aryl group or a substituted aryl-$C_1$–$C_4$-alkyl or aryl group, wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups; or $R^{15}{}_l$ and $R^{16}{}_l$, together with the carbon atom, form a cyclic system, a cyclic system fused to an aromatic ring system or a cyclic system selected from the group consisting of:

(a)
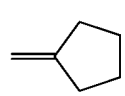

(b)
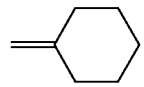

(c)
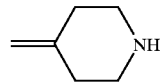

(d)
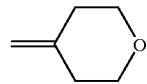

(e)
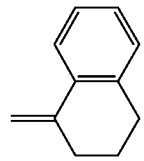

(f)
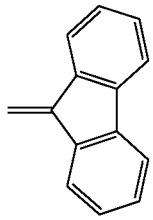

(g)
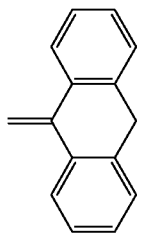

(h)
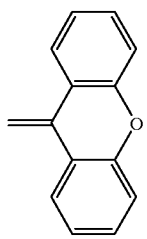

(i)
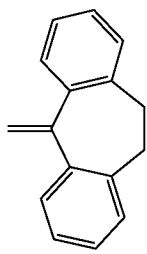

(j)
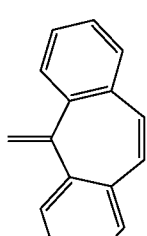

(k)
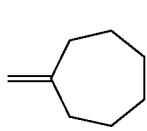

(l)
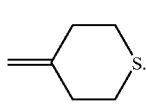

9. The compound of claim 1 wherein G is a hydrogen atom, a normal or branched $C_1$–$C_8$-alkyl group, a halogen-substituted normal or branched $C_1$–$C_8$-alkyl group, a $C_3$–$C_8$ cycloalkyl group, or a $C_3$–$C_8$-cycloalkyl-$C_1$–$C_4$-alkyl group.

10. The compound of claim 1 wherein G is a monovalent radical of Formula $V_g$, $$-(CH_2)_{a_g}-R^{17}{}_l \qquad (V_g)$$

$a_g$ is 0, 1, or 2, and $R^{17}{}_l$ is an aryl group or a substituted aryl group wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, imidazole or quinoline and the heteroaryl substituents comprise one or more $C_1$–$C_6$-alkyl, hydroxyl or phenyl groups.

11. The compound of claim 1 wherein G is a monovalent radical of Formula $VI_g$, $$-(CH_2)_{b_g}-(C=O)_{c_g}-OR^{18}{}_l \qquad (VI_g)$$

$b_g$ is 0, 1, 2, or 3; $e_g$ is 0 or 1; $R^{18}{}_l$ is a hydrogen atom, a normal or branched $C_1$–$C_8$-alkyl group, a halogen substituted normal or branched $C_1$–$C_8$-alkyl group, a $C_3$–$C_8$-cycloalkyl group, a $C_3$–$C_8$-cycloalkyl-$C_1$–$C_4$-alkyl group, an aryl group or a substituted aryl group wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups.

12. The compound of claim 1 wherein G is a monovalent radical of Formula $VII_g$, $$-(CH_2)_{d_g}-(C=O)_{e_g}-N\begin{matrix}R^{19}{}_l\\R^{20}{}_l,\end{matrix} \qquad (VII_g)$$

$d_g$ is 0, 1, 2, or 3; $e_g$ is 0 or 1; $R^{19}{}_l$ and $R^{20}{}_l$ are, independently, a hydrogen atom, a normal or branched $C_1$–$C_8$-alkyl group, a halogen-substituted $C_1$–$C_8$-alkyl group, a $C_3$–$C_8$-cycloalkyl group, a $C_3$–$C_8$-cycloalkyl-$C_1$–$C_4$-alkyl group, an aryl group or a substituted aryl group wherein the aryl substituents comprise one or more halogen atoms or one or more alkoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups; or $R^{19}{}_l$, $R^{20}{}_l$ and the nitrogen atom form a ring system comprising 6 or fewer carbon atoms.

13. The compound of claim 1 wherein G is an alkylene sulfoxide or an alkylene sulfone of Formula $VIII_g$, $-(CH_2)_{g_g}-S(O)_{h_g}-R^{21}{}_l$ (VIII$_g$), g$_g$ is 1 or 2, h$_g$ is 1 or 2, and R$^{21}{}_l$ is a methyl, trifluoromethyl, ethyl or phenyl group.

14. A compound of the formula

A—B—D—E—F—G wherein A is N,N-dimethylvalyl, B is tertiary-leucyl, D is N-methylvalyl, E is prolyl, F is an aminobenzoic acid residue or an aminocycloalkanecarboxylic acid residue and G is a monovalent radical.

15. A compound of the formula

A—B—D—E—F—G wherein A is N,N-dimethylvalyl, B is valyl, D is N-methyl-tertiaryleucyl, E is prolyl, F is an aminobenzoic acid residue or an aminocycloalkanecarboxylic acid residue and G is a monovalent radical.

16. A compound of the formula

A—B—D—E—F—G wherein A is N-methyl-d-prolyl, B is valyl, D is N-methylvalyl, E is prolyl, F is an aminobenzoic acid residue or an aminocycloalkanecarboxylic acid residue and G is a monovalent radical.

17. A compound of the formula

A—B—D—E—F—G wherein A is N-methylhomoprolyl, B is valyl, D is N-methylvalyl, E is prolyl, F is an aminobenzoic acid residue or an aminocycloalkanecarboxylic acid residue and G is a monovalent radical.

18. A compound of the formula Me$_2$Val-Val-MeVal-Pro-F-G, wherein F is of Formula II$_f$ and R$_f$ is a hydrogen atom or a methyl group, R$^1{}_f$ and R$^2{}_f$ are each a hydrogen atom, an alkyl group or an alkoxy group, and G is an amino group, an N-substituted amino group, a hydrazido, an alkyl, cycloalkyl, aryl, or alkylaryl, an alkylene ester, an alkylene amide, an alkylene sulfoxide or an alkylene sulfone group or a monovalent radical of the formula —O—R$^{13}{}_l$ or —S—R$^{13}{}_l$, and R$^{13}{}_l$ is an alkyl, aryl or alkylaryl group.

19. A compound of the formula Me$_2$Val-Val-MeVal-Pro-F-G, wherein F is of Formula III$_f$, R$_f$ is a hydrogen atom or a methyl group, a$_f$ is 1 or 2, and G is an amino group, an N-substituted amino group, a hydrazido, an alkyl, cycloalkyl, aryl, or alkylaryl, an alkylene ester, an alkylene amide, an alkylene sulfoxide or an alkylene sulfone group or a monovalent radical of the formula —O—R$^{13}{}_l$ or —S—R$^{13}{}_l$, and R$^{13}{}_l$ is an alkyl, aryl or alkylaryl group.

20. A method for treating cancer in a mammal, comprising administering to the mammal a therapeutically effective amount of a compound of claim 1.

21. The method of claim 20 wherein the mammal is a human.

* * * * *

UNITED STATES PATENT AND TRADEMARK OFFICE
CERTIFICATE OF CORRECTION

PATENT NO. : 5,985,837
DATED : November 16, 1999
INVENTOR(S) : Kurt Ritter, Bernd Janssen, Andreas Haupt, Andreas Kling, Teresa Barlozzari and Wilhelm Amberg It is certified that error appears in the above-identified patent and that said Letters Patent is hereby corrected as shown below:

Column 72,
Line 35, in Formula $X_a$ delete "$(CH_2)_n$" and substitute therefor -- $(CH_2)n_a$ --.

Column 73,
Line 12, delete "$R^2d$" and substitute therefor -- $R^2_d$ --.

Column 75,
Line 9, delete "a tom" and substitute therefor -- atom --.
Line 28, delete "$(CH_2)al$" and substitute therefor -- $(CH_2)a_1$ --.

Column 76,
Line 9, delete "$(CH_2)bl$" and substitute therefor -- $(CH_2)b_1$ --.

Column 80,
Lines 18 and 19, delete "imidazole" and substitute therefor -- indazole --.

Column 82,
Line 8, after "Formula $II_f$" insert 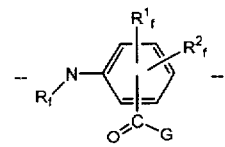

Line 17, after "Formula $III_f$" insert 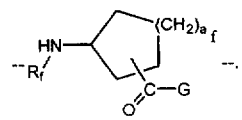

Signed and Sealed this

Sixteenth Day of April, 2002

JAMES E. ROGAN
Director of the United States Patent and Trademark Office